US007754687B2

(12) United States Patent
Mosoian et al.

(10) Patent No.: US 7,754,687 B2
(45) Date of Patent: Jul. 13, 2010

(54) METHODS OF INHIBITING VIRAL INFECTION

(75) Inventors: Arevik Mosoian, Jackson Heights, NY (US); Mary E. Klotman, New York, NY (US); Avelino Teixeira, Montclair, NJ (US)

(73) Assignee: Mount Sinai School of Medicine, New York, NY (US)

( * ) Notice: Subject to any disclaimer, the term of this patent is extended or adjusted under 35 U.S.C. 154(b) by 415 days.

(21) Appl. No.: 11/360,296

(22) Filed: Feb. 23, 2006

(65) Prior Publication Data

US 2006/0258565 A1 Nov. 16, 2006

Related U.S. Application Data

(60) Provisional application No. 60/655,924, filed on Feb. 24, 2005.

(51) Int. Cl.
*A61K 38/22* (2006.01)

(52) U.S. Cl. .......................................... 514/12; 514/21

(58) Field of Classification Search ....................... None
See application file for complete search history.

(56) References Cited

U.S. PATENT DOCUMENTS

| | | | | |
|---|---|---|---|---|
| 4,716,148 | A * | 12/1987 | Horecker | 514/12 |
| 6,200,952 | B1 * | 3/2001 | Horwitz | 514/12 |
| 2002/0086019 | A1 * | 7/2002 | Wolf et al. | 424/146.1 |
| 2002/0090692 | A1 * | 7/2002 | Prayaga et al. | 435/183 |
| 2003/0195150 | A1 * | 10/2003 | Reynolds et al. | 514/12 |

FOREIGN PATENT DOCUMENTS

| | | | |
|---|---|---|---|
| DE | 100 45 621 | A1 * | 4/2002 |
| WO | WO 03/035111 | A1 * | 5/2003 |

* cited by examiner

*Primary Examiner*—Jeffrey E Russel
(74) *Attorney, Agent, or Firm*—Klauber & Jackson LLC

(57) ABSTRACT

The present invention is directed to methods of preventing and/or treating infectious disease. In a particular aspect, the invention is directed to treating viral infections by administering an isolated Prothymosin alpha molecule (SEQ ID NO: 2) to a subject in a therapeutically effective amount that reduces the symptoms associated with the viral infection. In a more particular embodiment, the viral infection is caused by a retrovirus, a lentivirus, or a hepatitis virus. In a particular aspect, the viral infection is caused by human immunodeficiency virus-1.

10 Claims, 37 Drawing Sheets

FIG. 1A
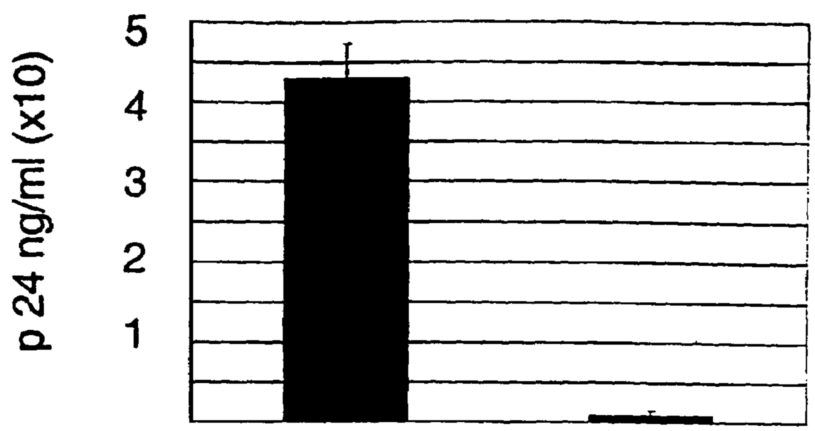
FIG. 1B
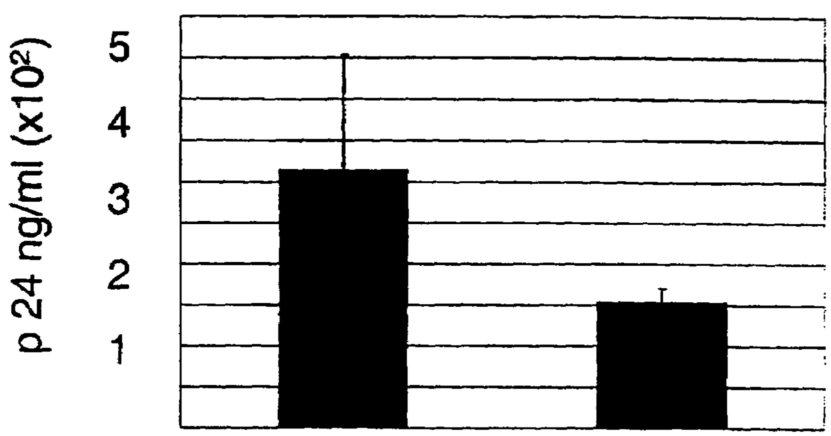
FIG. 1C
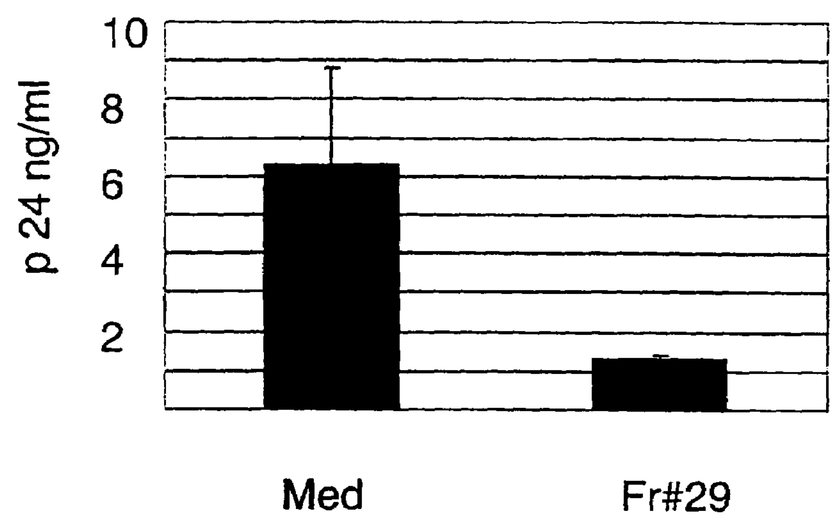
Med Fr#29
Figure 1

FIG. 2A
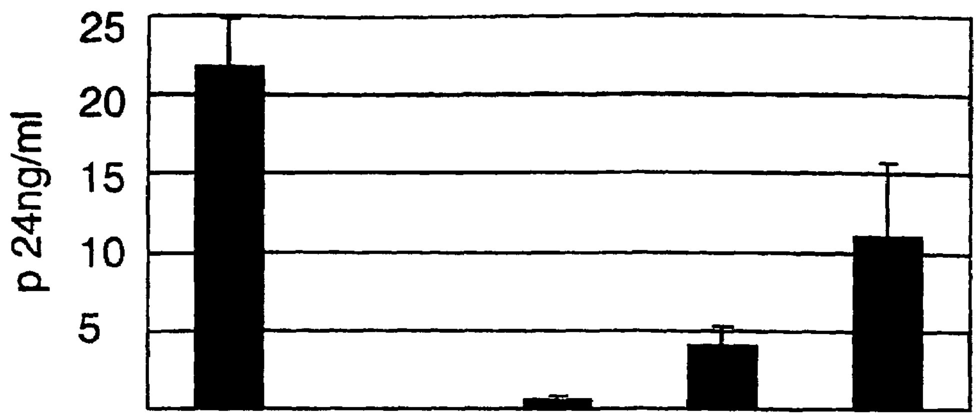
FIG. 2B
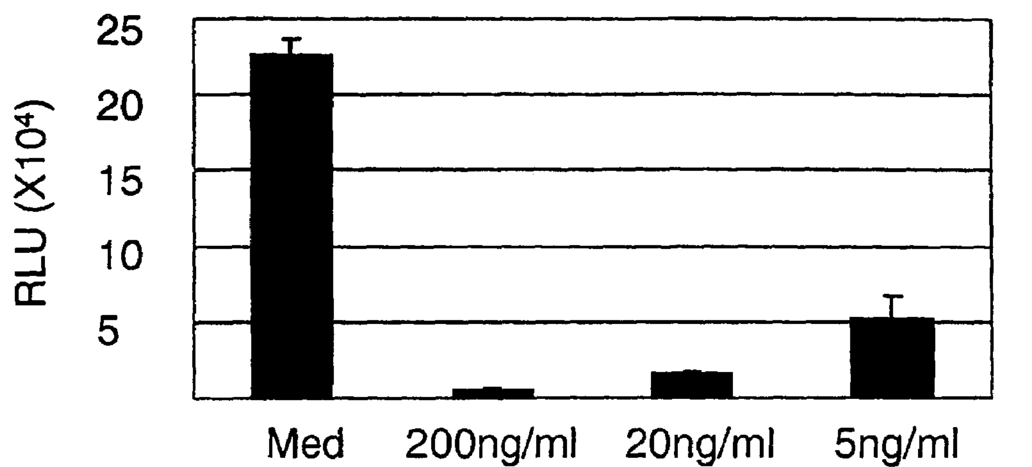
FIG. 2C
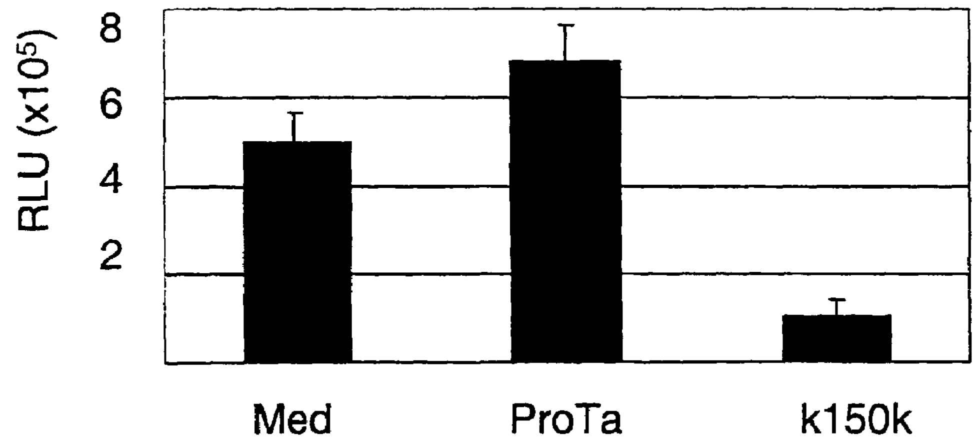
Figure 2

FIG. 7A
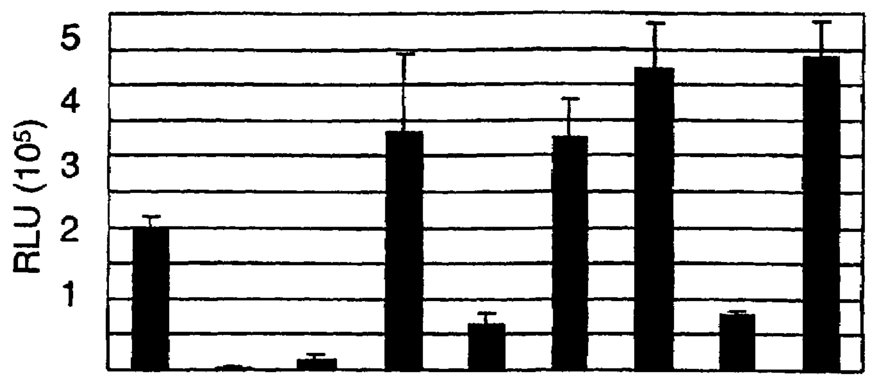
FIG. 7B
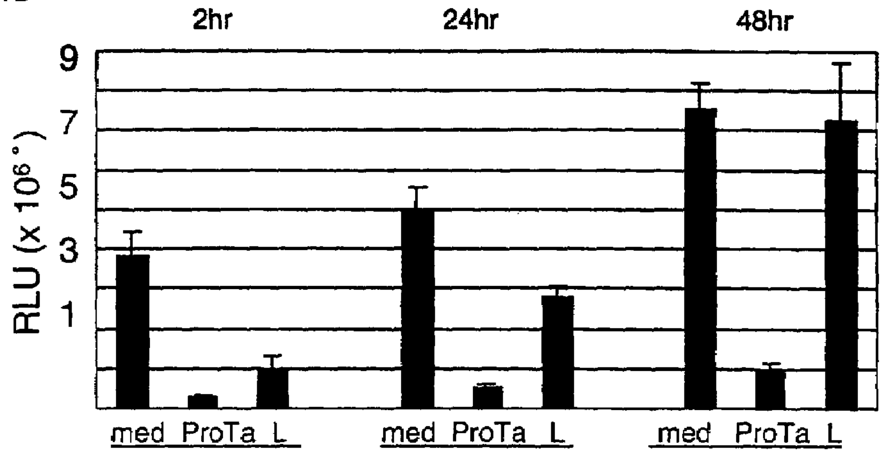
FIG. 7C
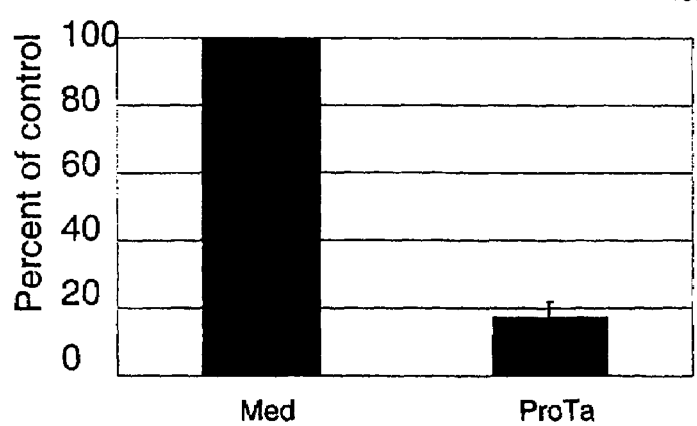
Figure 7

Macrophages

Med ProTα K150k

Hela-CD4

Med ProTα K150k

P-Stat 1

Stat 1

Figure 8

FIG. 9A
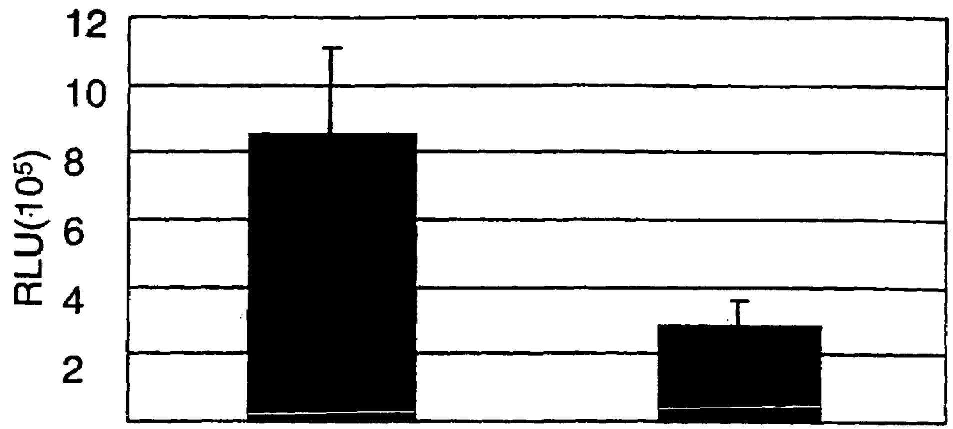
FIG. 9B
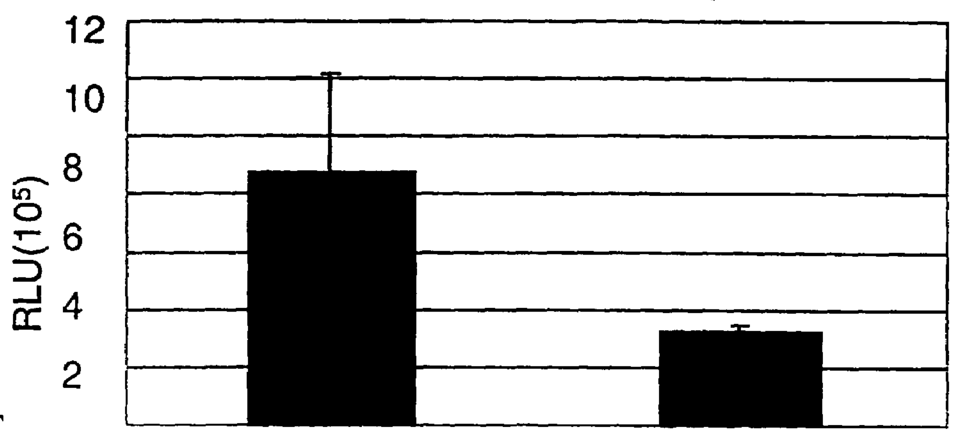
FIG. 9C
5
4
3
2
1
RLU($10^4$)
Figure 9

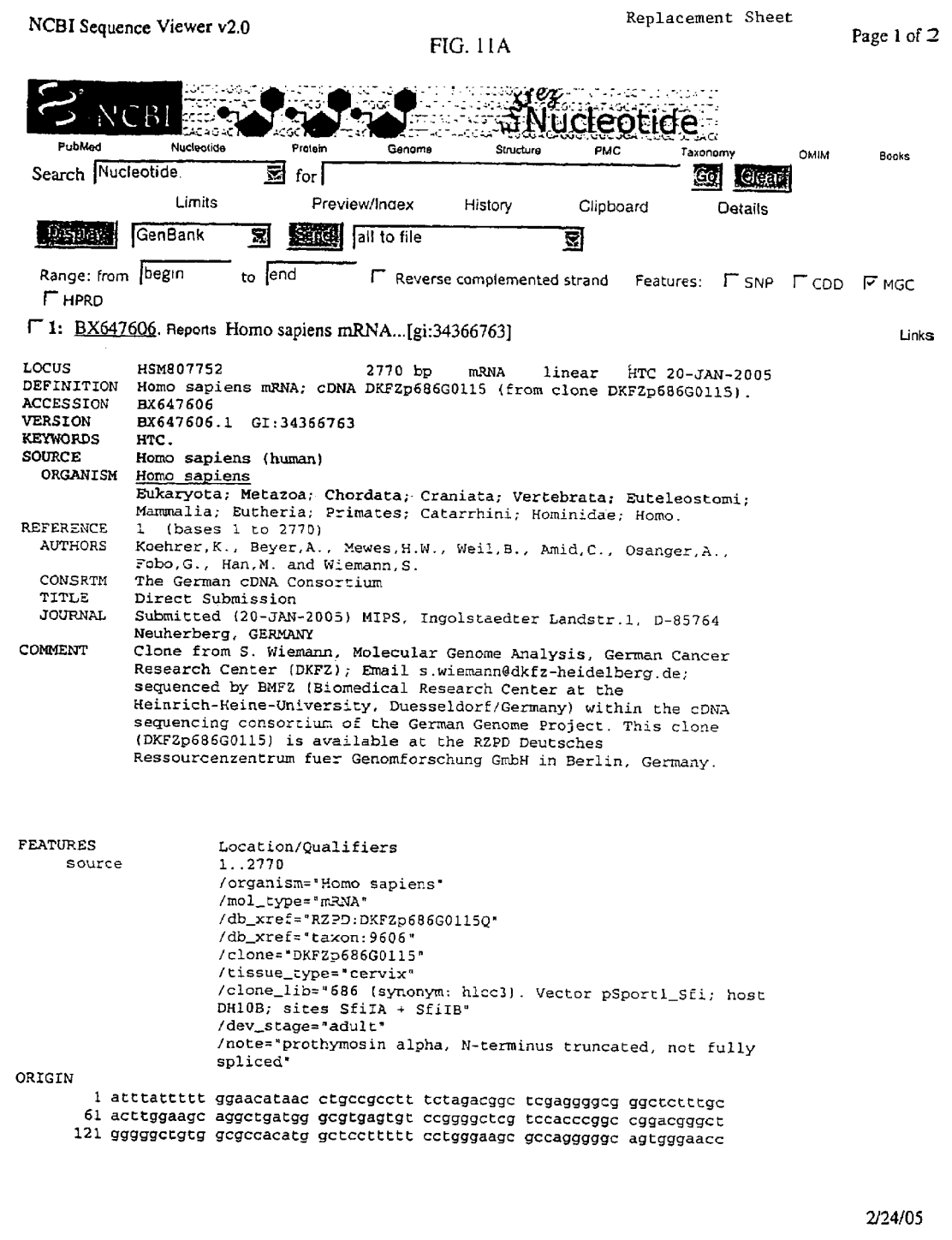

NCBI Sequence Viewer v2.0

Replacement Sheet

FIG. 11A

Page 1 of 2

NCBI Nucleotide

PubMed Nucleotide Protein Genome Structure PMC Taxonomy OMIM Books

Search Nucleotide for Go Clear

Limits Preview/Index History Clipboard Details

Display GenBank Send all to file

Range: from begin to end Reverse complemented strand Features: SNP CDD MGC HPRD

1: BX647606. Reports Homo sapiens mRNA...[gi:34366763]

Links

```
LOCUS       HSM807752              2770 bp    mRNA    linear   HTC 20-JAN-2005
DEFINITION  Homo sapiens mRNA; cDNA DKFZp686G0115 (from clone DKFZp686G0115).
ACCESSION   BX647606
VERSION     BX647606.1  GI:34366763
KEYWORDS    HTC.
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 2770)
  AUTHORS   Koehrer,K., Beyer,A., Mewes,H.W., Weil,B., Amid,C., Osanger,A.,
            Fobo,G., Han,M. and Wiemann,S.
  CONSRTM   The German cDNA Consortium
  TITLE     Direct Submission
  JOURNAL   Submitted (20-JAN-2005) MIPS, Ingolstaedter Landstr.1, D-85764
            Neuherberg, GERMANY
COMMENT     Clone from S. Wiemann, Molecular Genome Analysis, German Cancer
            Research Center (DKFZ); Email s.wiemann@dkfz-heidelberg.de;
            sequenced by BMFZ (Biomedical Research Center at the
            Heinrich-Heine-University, Duesseldorf/Germany) within the cDNA
            sequencing consortium of the German Genome Project. This clone
            (DKFZp686G0115) is available at the RZPD Deutsches
            Ressourcenzentrum fuer Genomforschung GmbH in Berlin, Germany.

FEATURES             Location/Qualifiers
     source          1..2770
                     /organism="Homo sapiens"
                     /mol_type="mRNA"
                     /db_xref="RZPD:DKFZp686G0115Q"
                     /db_xref="taxon:9606"
                     /clone="DKFZp686G0115"
                     /tissue_type="cervix"
                     /clone_lib="686 (synonym: hlcc3). Vector pSport1_Sfi; host
                     DH10B; sites SfiIA + SfiIB"
                     /dev_stage="adult"
                     /note="prothymosin alpha, N-terminus truncated, not fully
                     spliced"
ORIGIN
        1 atttattttt ggaacataac ctgccgcctt tctagacggc tcgaggggcg ggctctttgc
       61 acttggaagc aggctgatgg gcgtgagtgt ccggggctcg tccacccggc cggacgggct
      121 gggggctgtg gcgccacatg gctccttttt cctgggaagc gccagggggc agtgggaacc
```

FIG. 11A CONT'D 181 gccaccgggg ccgctgtagc gggccttaaa ggatgggaaa ccttgatcac agatgccccc
241 cgccggcctt ccttccacca gaccagtggg agagggaccg caggggcatc aggcctttct
301 caacatgcga ctcttaattt gggacggaca gaacagccgt acagaccagt agttctcagc
361 gcctttgctt accctgggtt gctcagaaga cttactggtt actggttcct tcttcccttt
421 tgaaggactt aaaggagaag aaggaagttg tggaagaggc agaaaatgga agagacgccc
481 ctgctaacgg gaatgctgtg agtgtctgct ttgctcctga gccctggcag ctaccgcccc
541 acaaaatttt tcctgttcta ctttaaacat acctatatat gtgtgtgtat gtgtatatgt
601 atagctttcc acagtggcag tatcgtagcc aatgagcttt acccgaggcg cgattattgc
661 tagttaaata tttataaaaa cctttcgagc agcgcctgaa caagaatagg ttcagaggag
721 actccggtag tctgagtttg ggcttggccc agggtgggga aaagcccttg tcctggggca
781 gttaatgtgc aggtttcacg atggagcctg gagggtgttg actggagaag ggtctctggg
841 gtgggcttgg cttggctggg ctgtagatgc agccgccagc ctctggtggg aggccgggca
901 tcaggagcaa cgctctgtcc agcctggggc caactggtaa tgacatggcc tgtttctgt
961 cgaggagaat gaggaaaatg gggagcagga ggctgacaat gaggtagacg aagaagagga
1021 agaaggtggg gaggaagagg aggaggaaga agaaggtgat ggtgagtagc cttgtctatc
1081 ttcccctttt caggtacttt ttcctggcct tgtctggcag aaggggaagg aaggaattgg
1141 ggctcctggg agtgggacaa tggtacttgg ggccagtgga ccacatggcc ctgggcaccc
1201 acctgtagag tcagggaagg tctccctgac atggagttgt gcccatgccc actcacactc
1261 actcgcacac ctgaaagttt ctttcgtgca gctctgaaag ccactgatct attgggctgg
1321 ccttttgggg tgcagctgct tgggcctctc tcctctggag agtcccacct gtgtagtggg
1381 cgtgggtgcc ctgattgggc ccagttgcag gcagtagagg cagggcaggg accttgcagt
1441 ccactacatg ttcctcggga tttccccagg agccacagta ggagggaagt gtggtttacc
1501 tggcctttga ttctctccag gtgaggaaga ggatggagat gaagatgagg aagctgagtc
1561 agctacgggc aagcgggcag ctgaagatga tgaggtgggt tctggcttga gaagaagggg
1621 ggtttggcat ctgggtctcc ccacctgcct ttagctgagg tgctcaagct gcggagggac
1681 tgtttctgac tttgtaggtg gccactgtgt ggtcctgaat cttaagaaca ggaaggaaac
1741 agggctgggc tcaacttccc agaggccttg ggctgtggag ctgggggtcc ctggttcttg
1801 ctctgccagc aggagctgag gcagtgggct ggatagggct cctggggttg gaggggcctt
1861 tgacagtctt tctctgctta ggatgacgat gtcgatacca agaagcagaa gaccgacgag
1921 gatgactaga cagcaaaaaa ggaaaagtta aactaaaaaa aaaaaggccg ccgtgaccca
1981 ttcaccctcc acttcccgtc tcagaatcta aacgtggtca ccttcgagta gagaggcccg
2041 cccgcccacc gtgggcagtg ccacccgcag atgacacgcg ctctccacca cccaacccaa
2101 accatgagaa tttgcaacag gggaggaaaa aagaaccaaa acttccaagg ccctgctttt
2161 tttcttaaaa gtactttaaa aaggaaattt gtttgtattt tttatttaca ttttatattt
2221 ttgtacatat tgttagggtc agccattttt aatgatctcg gatgaccaaa ccagccttcg
2281 gagcgttctc tgtcctactt cttgactttac ttgtggtgtg accatgttca ttataatctc
2341 aaaggagaaa aaaaaccttg taaaaaaagc aaaaatgaca acagaaaaac aatcttattc
2401 cgagcattcc agtaactttt ttgtgtatgt acttagctgt actataagta gttggtttgt
2461 atgagatggt taaaaaggcc aaagataaaa ggtttctttt tttttccttt tttgtctatg
2521 aagttgctgt ttattttttt tggcctgttt gatgtatgtg tgaaacaatg ttgtccaaca
2581 ataaacagga attttatttt gctgagttgt tctacaaaaa aaaaaaaaaa aaaaaaaaaa
2641 aaaaaaaaaa aaaaaaaaaa aaaaaaaaaa aaaaaaaaaa aaaaaaaaaa aaaaaaaaaa
2701 aaaaaaaaaa aaaaaaaaaa aaaaaaaaaa aaaaaaaaaa aaaaaaaaaa agaaaaaaaa
2761 aaaaaaaaaa Disclaimer | Write to the Help Desk
NCBI | NLM | NIH

FIG. 11B

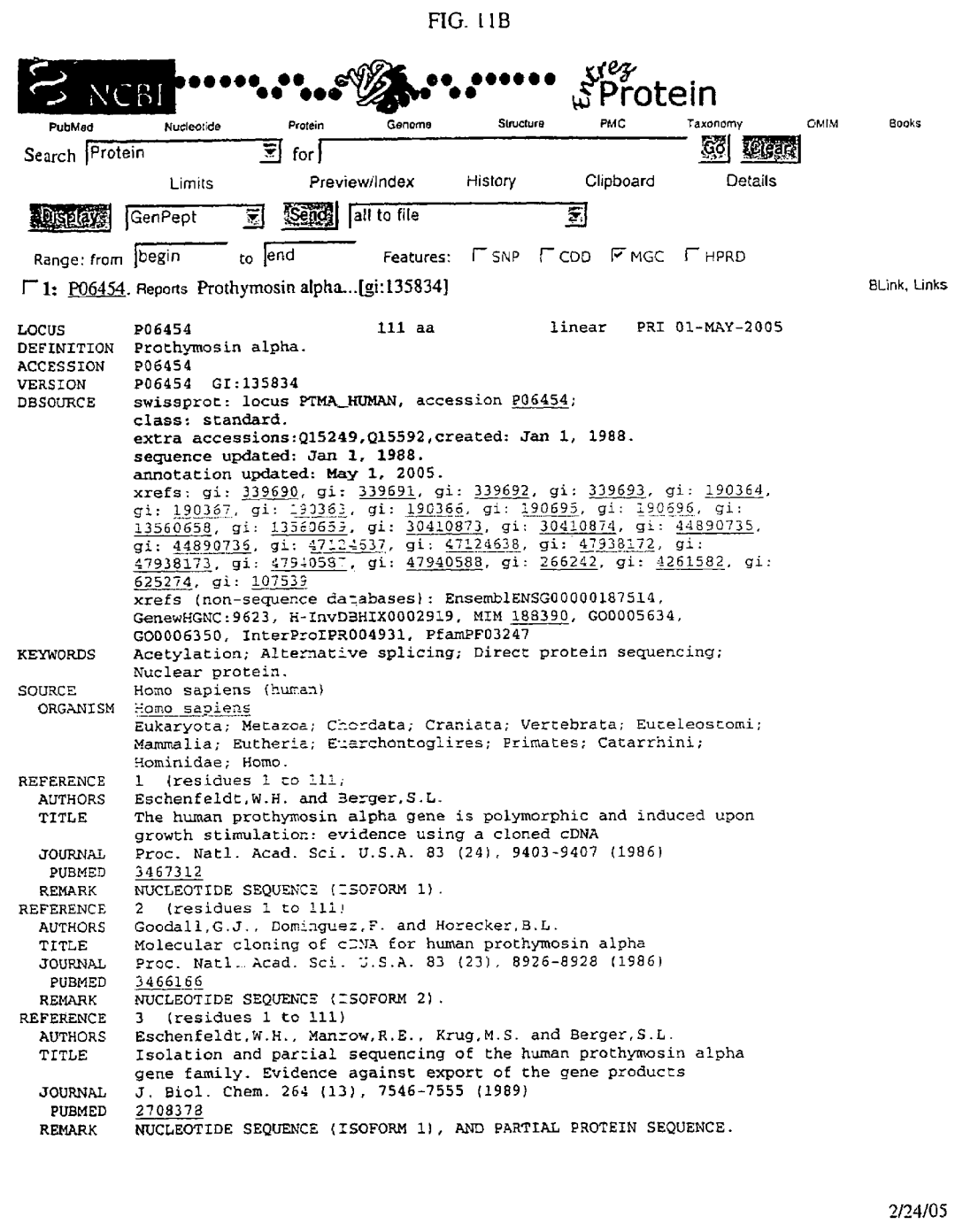

NCBI Entrez Protein

PubMed Nucleotide Protein Genome Structure PMC Taxonomy OMIM Books

Search Protein for Go Clear

Limits Preview/Index History Clipboard Details

Display GenPept Send all to file

Range: from begin to end Features: SNP CDD MGC HPRD

1: P06454. Reports Prothymosin alpha...[gi:135834] BLink, Links

```
LOCUS       P06454                  111 aa            linear   PRI 01-MAY-2005
DEFINITION  Prothymosin alpha.
ACCESSION   P06454
VERSION     P06454  GI:135834
DBSOURCE    swissprot: locus PTMA_HUMAN, accession P06454;
            class: standard.
            extra accessions:Q15249,Q15592,created: Jan 1, 1988.
            sequence updated: Jan 1, 1988.
            annotation updated: May 1, 2005.
            xrefs: gi: 339690, gi: 339691, gi: 339692, gi: 339693, gi: 190364,
            gi: 190367, gi: 190363, gi: 190366, gi: 190695, gi: 190696, gi:
            13560658, gi: 13560659, gi: 30410873, gi: 30410874, gi: 44890735,
            gi: 44890736, gi: 47124637, gi: 47124638, gi: 47938172, gi:
            47938173, gi: 47940587, gi: 47940588, gi: 266242, gi: 4261582, gi:
            625274, gi: 107539
            xrefs (non-sequence databases): EnsemblENSG00000187514,
            GenewHGNC:9623, H-InvDBHIX0002919, MIM 188390, GO0005634,
            GO0006350, InterProIPR004931, PfamPF03247
KEYWORDS    Acetylation; Alternative splicing; Direct protein sequencing;
            Nuclear protein.
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Catarrhini;
            Hominidae; Homo.
REFERENCE   1  (residues 1 to 111)
  AUTHORS   Eschenfeldt,W.H. and Berger,S.L.
  TITLE     The human prothymosin alpha gene is polymorphic and induced upon
            growth stimulation: evidence using a cloned cDNA
  JOURNAL   Proc. Natl. Acad. Sci. U.S.A. 83 (24), 9403-9407 (1986)
   PUBMED   3467312
  REMARK    NUCLEOTIDE SEQUENCE (ISOFORM 1).
REFERENCE   2  (residues 1 to 111)
  AUTHORS   Goodall,G.J., Dominguez,F. and Horecker,B.L.
  TITLE     Molecular cloning of cDNA for human prothymosin alpha
  JOURNAL   Proc. Natl. Acad. Sci. U.S.A. 83 (23), 8926-8928 (1986)
   PUBMED   3466166
  REMARK    NUCLEOTIDE SEQUENCE (ISOFORM 2).
REFERENCE   3  (residues 1 to 111)
  AUTHORS   Eschenfeldt,W.H., Manrow,R.E., Krug,M.S. and Berger,S.L.
  TITLE     Isolation and partial sequencing of the human prothymosin alpha
            gene family. Evidence against export of the gene products
  JOURNAL   J. Biol. Chem. 264 (13), 7546-7555 (1989)
   PUBMED   2708378
  REMARK    NUCLEOTIDE SEQUENCE (ISOFORM 1), AND PARTIAL PROTEIN SEQUENCE.
```

```
REFERENCE   4  (residues 1 to 111)
  AUTHORS   Gomez-Marquez,J., Segade,F., Dosil,M., Pichel,J.G., Bustelo,X.R.
            and Freire,M.
  TITLE     The expression of prothymosin alpha gene in T lymphocytes and
            leukemic lymphoid cells is tied to lymphocyte proliferation
  JOURNAL   J. Biol. Chem. 264 (15), 8451-8454 (1989)
   PUBMED   2785990
  REMARK    NUCLEOTIDE SEQUENCE (ISOFORM 2).
REFERENCE   5  (residues 1 to 111)
  AUTHORS   Li,Z., Fan,Q., Huang,W. and An,L.
  TITLE     Direct Submission
  JOURNAL   Submitted (??-FEB-2001)
  REMARK    NUCLEOTIDE SEQUENCE (ISOFORM 2).
            TISSUE=Fetal thymus
REFERENCE   6  (residues 1 to 111)
  AUTHORS   Strausberg,R.L., Feingold,E.A., Grouse,L.H., Derge,J.G.,
            Klausner,R.D., Collins,F.S., Wagner,L., Shenmen,C.M., Schuler,G.D.,
            Altschul,S.F., Zeeberg,B., Buetow,K.H., Schaefer,C.F., Bhat,N.K.,
            Hopkins,R.F., Jordan,H., Moore,T., Max,S.I., Wang,J., Hsieh,F.,
            Diatchenko,L., Marusina,K., Farmer,A.A., Rubin,G.M., Hong,L.,
            Stapleton,M., Soares,M.B., Bonaldo,M.F., Casavant,T.L.,
            Scheetz,T.E., Brownstein,M.J., Usdin,T.B., Toshiyuki,S.,
            Carninci,P., Prange,C., Raha,S.S., Loquellano,N.A., Peters,G.J.,
            Abramson,R.D., Mullahy,S.J., Bosak,S.A., McEwan,P.J.,
            McKernan,K.J., Malek,J.A., Gunaratne,P.H., Richards,S.,
            Worley,K.C., Hale,S., Garcia,A.M., Gay,L.J., Hulyk,S.W.,
            Villalon,D.K., Muzny,D.M., Sodergren,E.J., Lu,X., Gibbs,R.A.,
            Fahey,J., Helton,E., Ketteman,M., Madan,A., Rodrigues,S.,
            Sanchez,A., Whiting,M., Madan,A., Young,A.C., Shevchenko,Y.,
            Bouffard,G.G., Blakesley,R.W., Touchman,J.W., Green,E.D.,
            Dickson,M.C., Rodriguez,A.C., Grimwood,J., Schmutz,J., Myers,R.M.,
            Butterfield,Y.S., Krzywinski,M.I., Skalska,U., Smailus,D.E.,
            Schnerch,A., Schein,J.E., Jones,S.J. and Marra,M.A.
  TITLE     Generation and initial analysis of more than 15,000 full-length
            human and mouse cDNA sequences
  JOURNAL   Proc. Natl. Acad. Sci. U.S.A. 99 (26), 16899-16903 (2002)
   PUBMED   12477932
  REMARK    NUCLEOTIDE SEQUENCE (ISOFORM 2).
            TISSUE=Cervix, Lung, PNS, Skin, and Testis
REFERENCE   7  (residues 1 to 111)
  AUTHORS   Szabo,P., Panneerselvam,C., Clinton,M., Frangou-Lazaridis,M.,
            Weksler,D., Whittington,E., Macera,M.J., Grzeschik,K.H.,
            Selvakumar,A. and Horecker,B.L.
  TITLE     Prothymosin alpha gene in humans: organization of its promoter
            region and localization to chromosome 2
  JOURNAL   Hum. Genet. 90 (6), 629-634 (1993)
   PUBMED   7916742
  REMARK    NUCLEOTIDE SEQUENCE OF 1-14.
REFERENCE   8  (residues 1 to 111)
  AUTHORS   Pan,L.X., Haritos,A.A., Wideman,J., Komiyama,T., Chang,M.,
            Stein,S., Salvin,S.B. and Horecker,B.L.
  TITLE     Human prothymosin alpha: amino acid sequence and immunologic
            properties
  JOURNAL   Arch. Biochem. Biophys. 250 (1), 197-201 (1986)
   PUBMED   3532956
  REMARK    PARTIAL PROTEIN SEQUENCE.
COMMENT     [FUNCTION] Prothymosin alpha may mediate immune function by
            conferring resistance to certain opportunistic infections.
            [SUBCELLULAR LOCATION] Nuclear.
            [ALTERNATIVE PRODUCTS] Event=Alternative splicing; Named
```

FIG. 11B CONT'D

```
          isoforms=2; Name=1; IsoId=P06454-1; Sequence=Displayed; Name=2;
          IsoId=P06454-2; Sequence=VSP_011508.
          [PTM] Covalently linked to a small RNA of about 20 nucleotides (By
          similarity).
          [SIMILARITY] Belongs to the pro/parathymosin family.
          -----------------------------------------------------------------
          -------This Swiss-Prot entry is copyright. It is produced through a
          collaboration between  the Swiss Institute of Bioinformatics  and
          the  EMBL outstation -the European Bioinformatics Institute.  There
          are no  restrictions on  its use as long as its content is in no
          way modified and this statement is not removed.
          -----------------------------------------------------------------
          -------.
FEATURES             Location/Qualifiers
     source          1..111
                     /organism="Homo sapiens"
                     /db_xref="taxon:9606"
     gene            1..111
                     /gene="PTMA"
                     /note="synonym: TMSA"
     Protein         1..111
                     /gene="PTMA"
                     /product="Prothymosin alpha"
     Region          2..29
                     /gene="PTMA"
                     /region_name="Processed active peptide"
                     /note="Thymosin alpha-1."
                     /evidence=experimental
     Site            2
                     /gene="PTMA"
                     /site_type="modified"
                     /note="N-acetylserine (Probable)."
                     /evidence=experimental
     Region          40
                     /gene="PTMA"
                     /region_name="Splicing variant"
                     /note="Missing (in isoform 2). /FTId=VSP_011508."
                     /evidence=experimental
     Region          42..101
                     /gene="PTMA"
                     /region_name="Domain"
                     /note="Asp/Glu-rich (acidic)."
                     /evidence=experimental
ORIGIN
        1 msdaavdtss eittkdlkek kevveeaeng rdapangnae neengeqead nevdeeeeeg
       61 geeeeeeeeg dgeeedgded eeaesatgkr aaeddedddv dtkkqktded d
```

FIG. 12

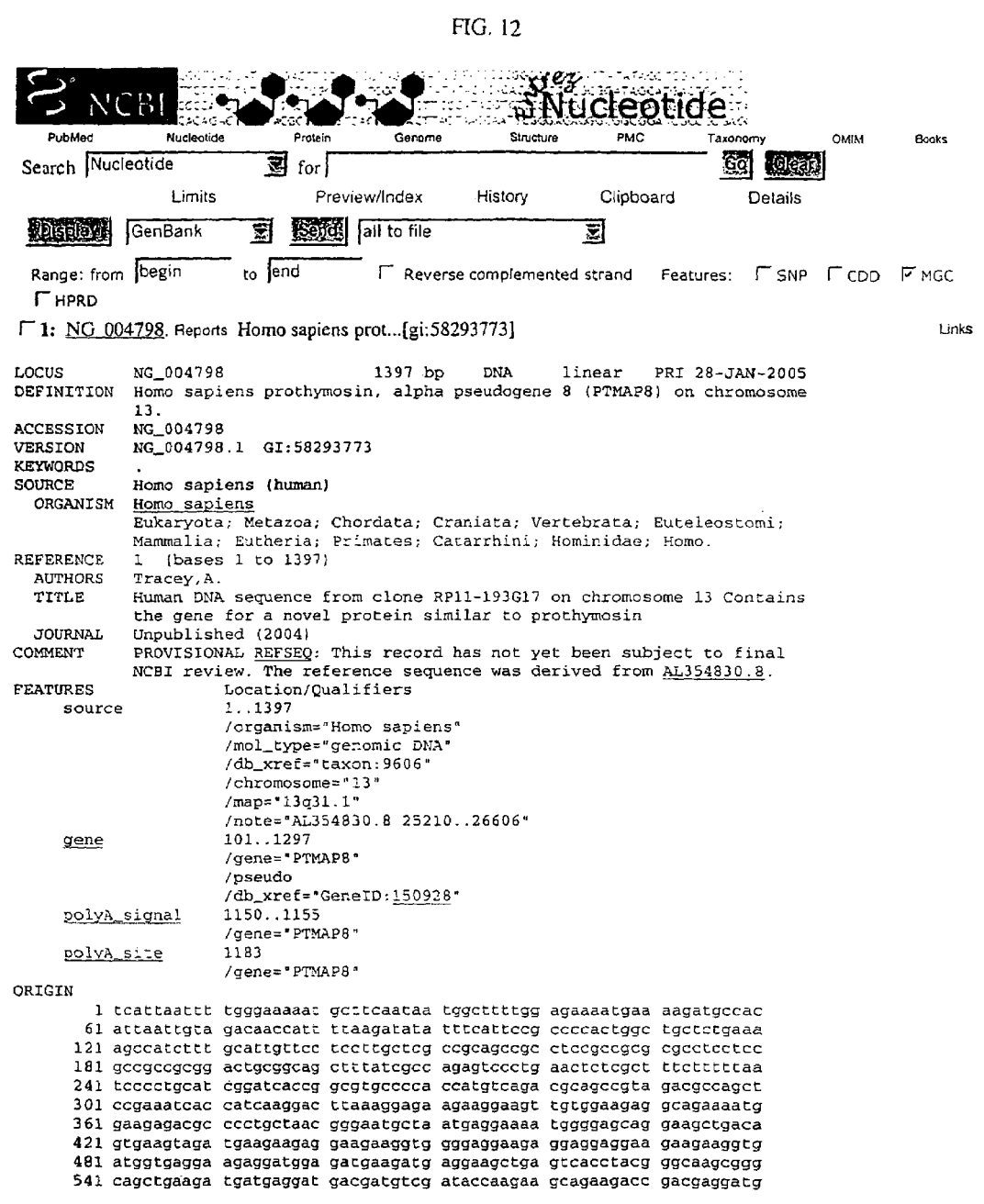

NCBI Nucleotide

PubMed Nucleotide Protein Genome Structure PMC Taxonomy OMIM Books

Search Nucleotide for Go Clear

Limits Preview/Index History Clipboard Details

Display GenBank Send all to file

Range: from begin to end Reverse complemented strand Features: SNP CDD MGC HPRD

1: NG_004798. Reports Homo sapiens prot...[gi:58293773] Links

```
LOCUS       NG_004798              1397 bp    DNA     linear   PRI 28-JAN-2005
DEFINITION  Homo sapiens prothymosin, alpha pseudogene 8 (PTMAP8) on chromosome
            13.
ACCESSION   NG_004798
VERSION     NG_004798.1  GI:58293773
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 1397)
  AUTHORS   Tracey,A.
  TITLE     Human DNA sequence from clone RP11-193G17 on chromosome 13 Contains
            the gene for a novel protein similar to prothymosin
  JOURNAL   Unpublished (2004)
COMMENT     PROVISIONAL REFSEQ: This record has not yet been subject to final
            NCBI review. The reference sequence was derived from AL354830.8.
FEATURES             Location/Qualifiers
     source          1..1397
                     /organism="Homo sapiens"
                     /mol_type="genomic DNA"
                     /db_xref="taxon:9606"
                     /chromosome="13"
                     /map="13q31.1"
                     /note="AL354830.8 25210..26606"
     gene            101..1297
                     /gene="PTMAP8"
                     /pseudo
                     /db_xref="GeneID:150928"
     polyA_signal    1150..1155
                     /gene="PTMAP8"
     polyA_site      1183
                     /gene="PTMAP8"
ORIGIN
        1 tcattaattt tgggaaaaat gcttcaataa tggcttttgg agaaaatgaa aagatgccac
       61 attaattgta gacaaccatt ttaagatata tttcattccg ccccactggc tgctctgaaa
      121 agccatcttt gcattgttcc tccttgctcg ccgcagccgc ctccgccgcg cgcctcctcc
      181 gccgccgcgg actgcggcag ctttatcgcc agagtccctg aactctcgct ttctttttaa
      241 tcccctgcat cggatcaccg gcgtgcccca ccatgtcaga cgcagccgta gacgccagct
      301 ccgaaatcac catcaaggac ttaaaggaga agaaggaagt tgtggaagag gcagaaaatg
      361 gaagagacgc ccctgctaac gggaatgcta atgaggaaaa tggggagcag gaagctgaca
      421 gtgaagtaga tgaagaagag gaagaaggtg gggaggaaga ggaggaggaa gaagaaggtg
      481 atggtgagga agaggatgga gatgaagatg aggaagctga gtcacctacg ggcaagcggg
      541 cagctgaaga tgatgaggat gacgatgtcg ataccaagaa gcagaagacc gacgaggatg
```

FIG. 12 CONT'D

```
 601 actagacagc aaaaaaggaa aagttaaact aaaaaaaaag gccgccgtga cctattcacc
 661 ctccacttcc cgtctcagaa tctaaacgtg gtcaccttca agtagagagg cccgcctgcc
 721 caccgtgggc agtgccaccc acagatgata cgcgctctcc accacccaac ccaaaccatg
 781 agaatttgca acaggggagg aaaaaagaac caaaacttcc aaggccatgc tttttttctt
 841 aaaagtactt taaaaaggaa atttgtttgt atttttatt tacattttat atttttatac
 901 atattgttag ggtcagccat ttttaatgat ctcggatgac caaaccagcc ttgggagcgt
 961 tctgtcctac ttctgacttt acttgtggtg tgaccatgtt cattataatc tcaaaggaga
1021 aaaaaacctt gtaaaaaaag caaaaatgac aacagaaaaa caatcttatt ctgagcattc
1081 cagtaacttt tttgtgtatg tacttagctg tactataagg agttggtttg tatgagatgg
1141 ttaaaaaggc caaagataaa aggtttattt tttttccttt tttgtctatg aagttgctgt
1201 ttattttttt tggcctgttt gatgtatgtg tgaaacaatg ttgtccaaca ataaacagga
1261 attttatttt gctgagttgt tctaaaaaaa aaaaaaagat gtatttcatt ccaactacaa
1321 agacattaca agtgtttgag atggtaaaca aactgattat cataatttga tcaatatgca
1381 atgtacacat gtactga
```

Disclaimer | Write to the Help Desk
NCBI | NLM | NIH

FIG. 13A

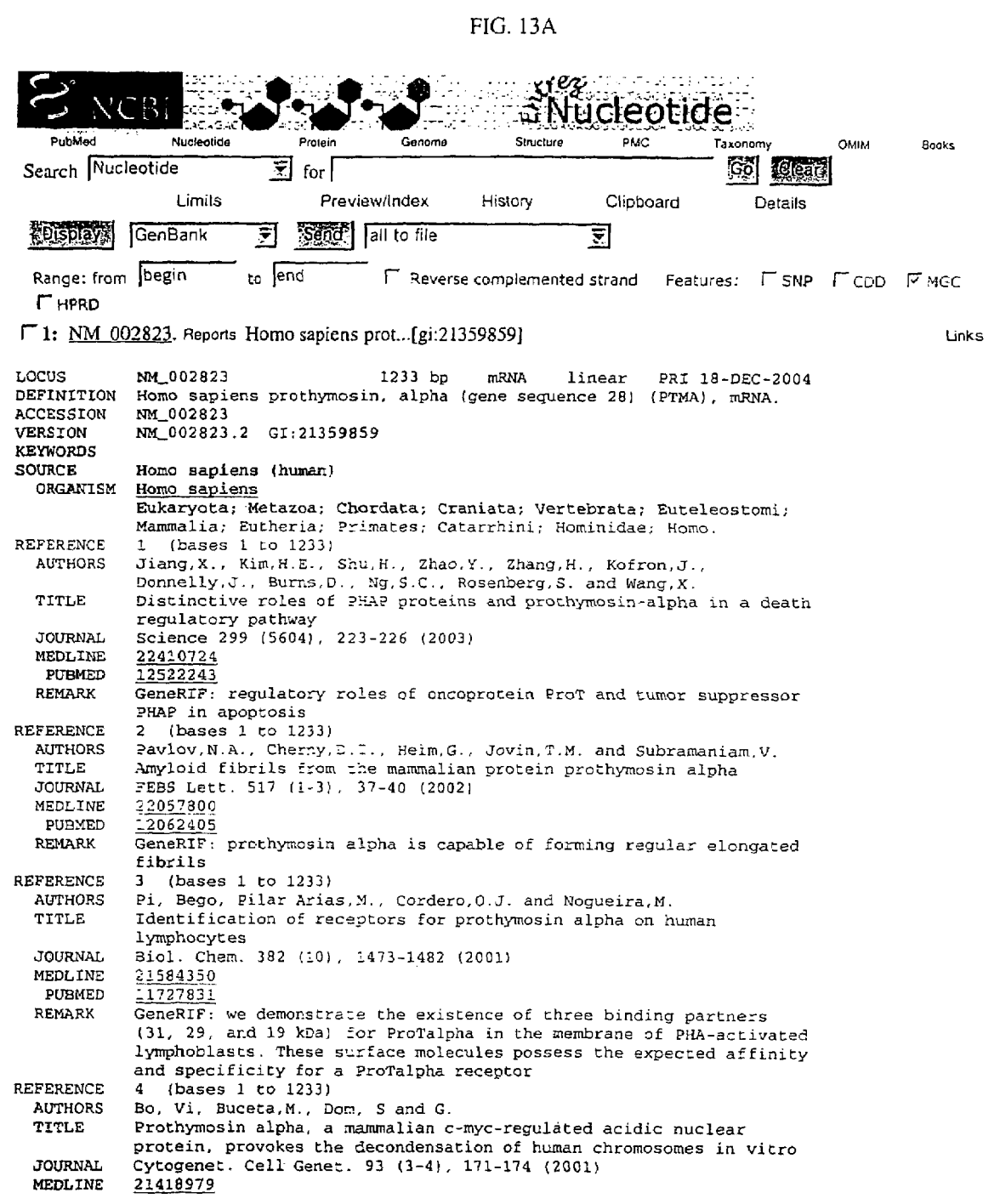

NCBI Nucleotide

PubMed Nucleotide Protein Genome Structure PMC Taxonomy OMIM Books

Search Nucleotide for Go Clear

Limits Preview/Index History Clipboard Details

Display GenBank Send all to file

Range: from begin to end Reverse complemented strand Features: SNP CDD MGC HPRD

1: NM_002823. Reports Homo sapiens prot...[gi:21359859] Links

```
LOCUS       NM_002823               1233 bp    mRNA    linear   PRI 18-DEC-2004
DEFINITION  Homo sapiens prothymosin, alpha (gene sequence 28) (PTMA), mRNA.
ACCESSION   NM_002823
VERSION     NM_002823.2  GI:21359859
KEYWORDS
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 1233)
  AUTHORS   Jiang,X., Kim,H.E., Shu,H., Zhao,Y., Zhang,H., Kofron,J.,
            Donnelly,J., Burns,D., Ng,S.C., Rosenberg,S. and Wang,X.
  TITLE     Distinctive roles of PHAP proteins and prothymosin-alpha in a death
            regulatory pathway
  JOURNAL   Science 299 (5604), 223-226 (2003)
  MEDLINE   22410724
   PUBMED   12522243
  REMARK    GeneRIF: regulatory roles of oncoprotein ProT and tumor suppressor
            PHAP in apoptosis
REFERENCE   2  (bases 1 to 1233)
  AUTHORS   Pavlov,N.A., Cherny,D.I., Heim,G., Jovin,T.M. and Subramaniam,V.
  TITLE     Amyloid fibrils from the mammalian protein prothymosin alpha
  JOURNAL   FEBS Lett. 517 (1-3), 37-40 (2002)
  MEDLINE   22057800
   PUBMED   12062405
  REMARK    GeneRIF: prothymosin alpha is capable of forming regular elongated
            fibrils
REFERENCE   3  (bases 1 to 1233)
  AUTHORS   Pi, Bego, Pilar Arias,M., Cordero,O.J. and Nogueira,M.
  TITLE     Identification of receptors for prothymosin alpha on human
            lymphocytes
  JOURNAL   Biol. Chem. 382 (10), 1473-1482 (2001)
  MEDLINE   21584350
   PUBMED   11727831
  REMARK    GeneRIF: we demonstrate the existence of three binding partners
            (31, 29, and 19 kDa) for ProTalpha in the membrane of PHA-activated
            lymphoblasts. These surface molecules possess the expected affinity
            and specificity for a ProTalpha receptor
REFERENCE   4  (bases 1 to 1233)
  AUTHORS   Bo, Vi, Buceta,M., Dom, S and G.
  TITLE     Prothymosin alpha, a mammalian c-myc-regulated acidic nuclear
            protein, provokes the decondensation of human chromosomes in vitro
  JOURNAL   Cytogenet. Cell Genet. 93 (3-4), 171-174 (2001)
  MEDLINE   21418979
```

FIG.13A CONT'D

```
  PUBMED    11528108
  REMARK    GeneRIF: induces unravelling of metaphase chromosomes in vitro
REFERENCE   5  (bases 1 to 1233)
  AUTHORS   Cotter,M.A. II and Robertson,E.S.
  TITLE     Modulation of histone acetyltransferase activity through
            interaction of epstein-barr nuclear antigen 3C with prothymosin
            alpha
  JOURNAL   Mol. Cell. Biol. 20 (15), 5722-5735 (2000)
  MEDLINE   20351605
   PUBMED   10891508
REFERENCE   6  (bases 1 to 1233)
  AUTHORS   Vareli,K., Frangou-Lazaridis,M., van der Kraan,I., Tsolas,O. and
            van Driel,R.
  TITLE     Nuclear distribution of prothymosin alpha and parathymosin:
            evidence that prothymosin alpha is associated with RNA synthesis
            processing and parathymosin with early DNA replication
  JOURNAL   Exp. Cell Res. 257 (1), 152-161 (2000)
  MEDLINE   20311124
   PUBMED   10854063
REFERENCE   7  (bases 1 to 1233)
  AUTHORS   Rubtsov,Iu.P. and Vartapetian,A.B.
  TITLE     New intronless members of human prothymosin alpha genes
  JOURNAL   Mol. Biol. (Mosk.) 29 (6), 1320-1325 (1995)
  MEDLINE   96139886
   PUBMED   8592501
REFERENCE   8  (bases 1 to 1233)
  AUTHORS   Kubota,S., Adachi,Y., Copeland,T.D. and Oroszlan,S.
  TITLE     Binding of human prothymosin alpha to the leucine-motif/activation
            domains of HTLV-I Rex and HIV-1 Rev
  JOURNAL   Eur. J. Biochem. 233 (1), 48-54 (1995)
  MEDLINE   96061931
   PUBMED   7588773
REFERENCE   9  (bases 1 to 1233)
  AUTHORS   Szabo,P., Panneerselvam,C., Clinton,M., Frangou-Lazaridis,M.,
            Weksler,D., Whittington,E., Macera,M.J., Grzeschik,K.H.,
            Selvakumar,A. and Horecker,B.L.
  TITLE     Prothymosin alpha gene in humans: organization of its promoter
            region and localization to chromosome 2
  JOURNAL   Hum. Genet. 90 (6), 629-634 (1993)
  MEDLINE   93186133
   PUBMED   7916742
REFERENCE   10 (bases 1 to 1233)
  AUTHORS   Manrow,R.E., Leone,A., Krug,M.S., Eschenfeldt,W.H. and Berger,S.L.
  TITLE     The human prothymosin alpha gene family contains several processed
            pseudogenes lacking deleterious lesions
  JOURNAL   Genomics 13 (2), 319-331 (1992)
  MEDLINE   92307664
   PUBMED   1612591
REFERENCE   11 (bases 1 to 1233)
  AUTHORS   G, Segade,F., Dosil,M., Pichel,J.G., Bustelo,X.R. and Freire,M.
  TITLE     The expression of prothymosin alpha gene in T lymphocytes and
            leukemic lymphoid cells is tied to lymphocyte proliferation
  JOURNAL   J. Biol  Chem. 264 (15), 8451-8454 (1989)
  MEDLINE   89255289
   PUBMED   2785990
REFERENCE   12 (bases 1 to 1233)
  AUTHORS   Eschenfeldt,W.H., Manrow,R.E., Krug,M.S. and Berger,S.L.
  TITLE     Isolation and partial sequencing of the human prothymosin alpha
            gene family. Evidence against export of the gene products
  JOURNAL   J. Biol. Chem. 264 (13), 7546-7555 (1989)
```

FIG. 13A CONT'D

```
  MEDLINE   89214202
   PUBMED   2708378
REFERENCE   13 (bases 1 to 1233)
  AUTHORS   Eschenfeldt,W.H. and Berger,S.L.
  TITLE     The human prothymosin alpha gene is polymorphic and induced upon
            growth stimulation: evidence using a cloned cDNA
  JOURNAL   Proc. Natl. Acad. Sci. U.S.A. 83 (24), 9403-9407 (1986)
  MEDLINE   87092260
   PUBMED   3467312
REFERENCE   14 (bases 1 to 1233)
  AUTHORS   Goodall,G.J., Dominguez,F. and Horecker,B.L.
  TITLE     Molecular cloning of cDNA for human prothymosin alpha
  JOURNAL   Proc. Natl. Acad. Sci. U.S.A. 83 (23), 8926-8928 (1986)
  MEDLINE   87067426
   PUBMED   3466166
COMMENT     PROVISIONAL REFSEQ: This record has not yet been subject to final
            NCBI review. The reference sequence was derived from BC022433.1.
            On Jun 9, 2002 this sequence version replaced gi:4506276.
FEATURES             Location/Qualifiers
     source          1..1233
                     /organism="Homo sapiens"
                     /mol_type="mRNA"
                     /db_xref="taxon:9606"
                     /chromosome="2"
                     /map="2q35-q36"
     gene            1..1233
                     /gene="PTMA"
                     /note="synonym: TMSA"
                     /db_xref="GeneID:5757"
                     /db_xref="MIM:188390"
     CDS             182..514
                     /gene="PTMA"
                     /note="prothymosin alpha; prothymosin alpha protein;
                     go_component: nucleus [goid 0005634] [evidence TAS] [pmid
                     10854063];
                     go_process: development [goid 0007275] [evidence NR];
                     go_process: transcription [goid 0006350] [evidence TAS]
                     [pmid 10854063];
                     go_process: regulation of cell cycle [goid 0000074]
                     [evidence NR]"
                     /codon_start=1
                     /product="prothymosin, alpha (gene sequence 28)"
                     /protein_id="NP_002814.2"
                     /db_xref="GI:21359860"
                     /db_xref="GeneID:5757"
                     /db_xref="MIM:188390"
                     /translation="MSDAAVDTSSEITTKDLKEKKEVVEEAENGRDAPANGNANEENG
                     EQEADNEVDEEEEEGGEEEEEEEEGDGEEEGGDEDEEAESATGKRAAEDDEDDDVDTK
                     KQKTDEDD"
ORIGIN
        1 ccccactggc tgctctgaaa agccatcttt gcattgttcc tcatccgcct ccttgctcgc
       61 cgcagccgcc tccgccgcgc gcctcctccg ccgccgcgga ctccggcagc tttatcgcca
      121 gagtccctga actctcgctt tctttttaat cccctgcatc ggatcaccgg cgtgccccac
      181 catgtcagac gcagccgtag acaccagctc cgaaatcacc accaaggact taaaggagaa
      241 gaaggaagtt gtggaagagg cagaaaatgg aagagacgcc cctgctaacg ggaatgctaa
      301 tgaggaaaat ggggagcagg aggctgacaa tgaggtagac gaagaagagg aagaaggtgg
      361 ggaggaagag gaggaggaag aagaaggtga tggtgaggag gagggtggag atgaagatga
      421 ggaagctgag tcagctacgg gcaagcgggc agctgaagat gatgaggatg acgatgtcga
      481 taccaagaag cagaagaccg acgaggatga ctagacagca aaaaaggaaa agttaaacta
      541 aaaaaaaaaa ggccgccgtg acctattcac cctccacttc ccgtctcaga atctaaacgt
```

FIG. 13A CONT'D

```
601 ggtcaccttc gagtagagag gcccgcccgc ccaccgtggg cagtgccacc cgcagatgac
661 acgcgctctc caccacccaa cccaaaccat gagaatttgc aacaggggag gaaaaagaa
721 ccaaaacttc caaggccctg cttttttct taaaagtact ttaaaagga aatttgtttg
781 tatttttat ttacatttta tattttgta catattgtta gggtcagcca tttttaatga
841 tctcggatga ccaaaccagc cttcggagcg ttctctgtcc tacttctgac tttacttgtg
901 gtgtgaccat gttcattata atctcaaagg agaaaaaaa ccttgtaaaa aaagcaaaaa
961 tgacaacaga aaaacaatct tattccgagc attccagtaa cttttttgtg tatgtactta
1021 gctgtactat aagtagttgg tttgtatgag atggttaaaa aggccaaaga taaaaggttt
1081 cttttttttt cctttttgt ctatgaagtt gctgtttatt ttttttggcc tgtttgatgt
1141 atgtgtgaaa caatgttgtc caacaataaa caggaatttt attttgctga gttgttctaa
1201 cagaaaaaa aaaaaaaaaa aaaaaaaaa aaa
```

Disclaimer | Write to the Help Desk
NCBI | NLM | NIH

FIG.13B

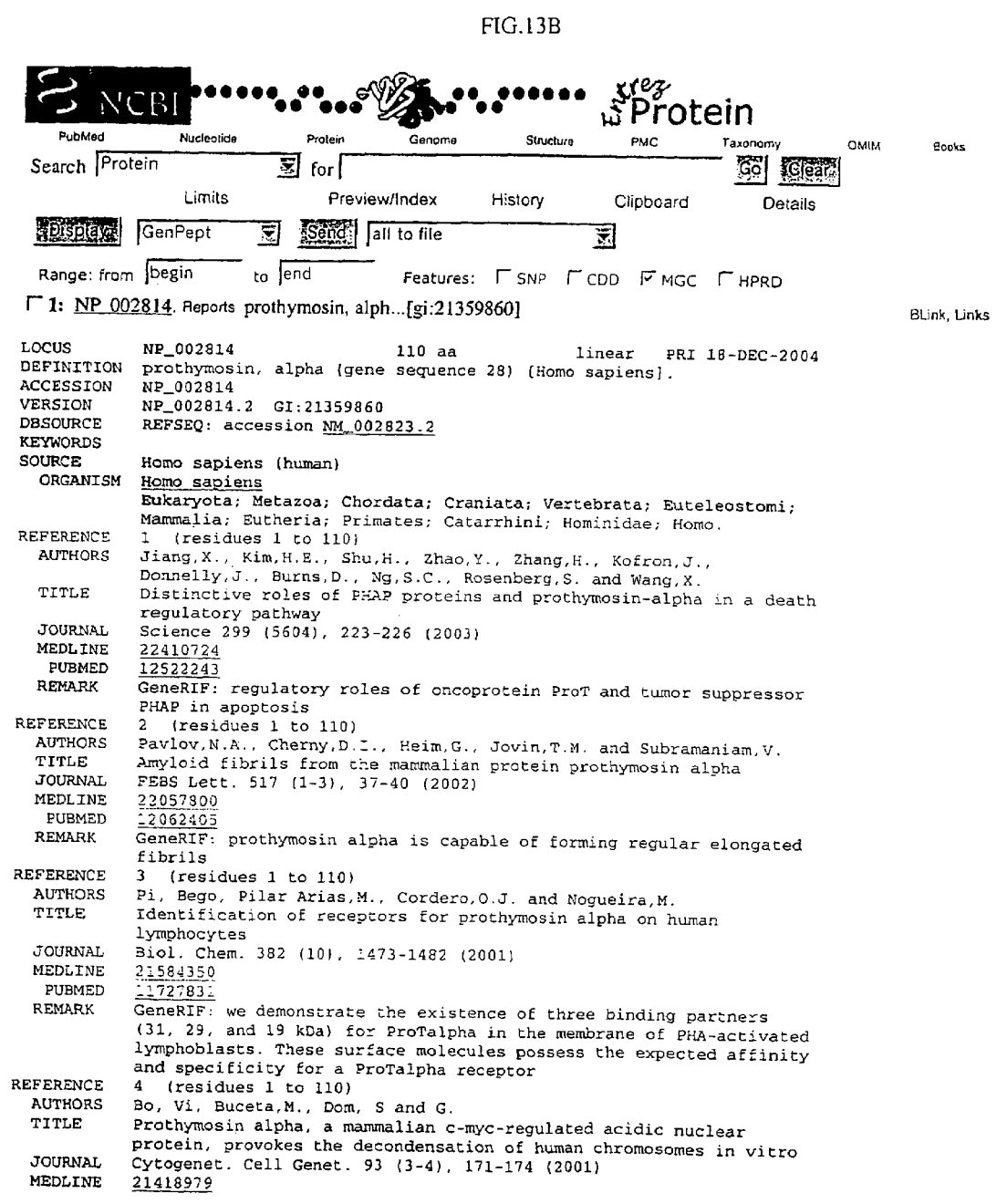

1: NP 002814. Reports prothymosin, alph...[gi:21359860] BLink, Links

```
LOCUS       NP_002814                 110 aa            linear   PRI 18-DEC-2004
DEFINITION  prothymosin, alpha (gene sequence 28) (Homo sapiens).
ACCESSION   NP_002814
VERSION     NP_002814.2  GI:21359860
DBSOURCE    REFSEQ: accession NM_002823.2
KEYWORDS
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (residues 1 to 110)
  AUTHORS   Jiang,X., Kim,H.E., Shu,H., Zhao,Y., Zhang,H., Kofron,J.,
            Donnelly,J., Burns,D., Ng,S.C., Rosenberg,S. and Wang,X.
  TITLE     Distinctive roles of PHAP proteins and prothymosin-alpha in a death
            regulatory pathway
  JOURNAL   Science 299 (5604), 223-226 (2003)
  MEDLINE   22410724
   PUBMED   12522243
  REMARK    GeneRIF: regulatory roles of oncoprotein ProT and tumor suppressor
            PHAP in apoptosis
REFERENCE   2  (residues 1 to 110)
  AUTHORS   Pavlov,N.A., Cherny,D.I., Heim,G., Jovin,T.M. and Subramaniam,V.
  TITLE     Amyloid fibrils from the mammalian protein prothymosin alpha
  JOURNAL   FEBS Lett. 517 (1-3), 37-40 (2002)
  MEDLINE   22057800
   PUBMED   12062405
  REMARK    GeneRIF: prothymosin alpha is capable of forming regular elongated
            fibrils
REFERENCE   3  (residues 1 to 110)
  AUTHORS   Pi, Bego, Pilar Arias,M., Cordero,O.J. and Nogueira,M.
  TITLE     Identification of receptors for prothymosin alpha on human
            lymphocytes
  JOURNAL   Biol. Chem. 382 (10), 1473-1482 (2001)
  MEDLINE   21584350
   PUBMED   11727831
  REMARK    GeneRIF: we demonstrate the existence of three binding partners
            (31, 29, and 19 kDa) for ProTalpha in the membrane of PHA-activated
            lymphoblasts. These surface molecules possess the expected affinity
            and specificity for a ProTalpha receptor
REFERENCE   4  (residues 1 to 110)
  AUTHORS   Bo, Vi, Buceta,M., Dom, S and G.
  TITLE     Prothymosin alpha, a mammalian c-myc-regulated acidic nuclear
            protein, provokes the decondensation of human chromosomes in vitro
  JOURNAL   Cytogenet. Cell Genet. 93 (3-4), 171-174 (2001)
  MEDLINE   21418979
```

FIG. 13B CONT'D

```
  PUBMED   11528108
  REMARK   GeneRIF: induces unravelling of metaphase chromosomes in vitro
REFERENCE  5  (residues 1 to 110)
  AUTHORS  Cotter,M.A. II and Robertson,E.S.
  TITLE    Modulation of histone acetyltransferase activity through
           interaction of epstein-barr nuclear antigen 3C with prothymosin
           alpha
  JOURNAL  Mol. Cell. Biol. 20 (15), 5722-5735 (2000)
  MEDLINE  20351605
  PUBMED   10891508
REFERENCE  6  (residues 1 to 110)
  AUTHORS  Vareli,K., Frangou-Lazaridis,M., van der Kraan,I., Tsolas,O. and
           van Driel,R.
  TITLE    Nuclear distribution of prothymosin alpha and parathymosin:
           evidence that prothymosin alpha is associated with RNA synthesis
           processing and parathymosin with early DNA replication
  JOURNAL  Exp. Cell Res. 257 (1), 152-161 (2000)
  MEDLINE  20311124
  PUBMED   10854063
REFERENCE  7  (residues 1 to 110)
  AUTHORS  Rubtsov,Iu.P. and Vartapetian,A.B.
  TITLE    New intronless members of human prothymosin alpha genes
  JOURNAL  Mol. Biol. (Mosk.) 29 (6), 1320-1325 (1995)
  MEDLINE  96139886
  PUBMED   8592501
REFERENCE  8  (residues 1 to 110)
  AUTHORS  Kubota,S., Adachi,Y., Copeland,T.D. and Oroszlan,S.
  TITLE    Binding of human prothymosin alpha to the leucine-motif/activation
           domains of HTLV-I Rex and HIV-1 Rev
  JOURNAL  Eur. J. Biochem. 233 (1), 48-54 (1995)
  MEDLINE  96061931
  PUBMED   7588773
REFERENCE  9  (residues 1 to 110)
  AUTHORS  Szabo,P., Panneerselvam,C., Clinton,M., Frangou-Lazaridis,M.,
           Weksler,D., Whittington,E., Macera,M.J., Grzeschik,K.H.,
           Selvakumar,A. and Horecker,B.L.
  TITLE    Prothymosin alpha gene in humans: organization of its promoter
           region and localization to chromosome 2
  JOURNAL  Hum. Genet. 90 (6), 629-634 (1993)
  MEDLINE  93186133
  PUBMED   7916742
REFERENCE  10 (residues 1 to 110)
  AUTHORS  Manrow,R.E., Leone,A., Krug,M.S., Eschenfeldt,W.H. and Berger,S.L.
  TITLE    The human prothymosin alpha gene family contains several processed
           pseudogenes lacking deleterious lesions
  JOURNAL  Genomics 13 (2), 319-331 (1992)
  MEDLINE  92307664
  PUBMED   1612591
REFERENCE  11 (residues 1 to 110)
  AUTHORS  G, Segade,F., Dosil,M., Pichel,J.G., Bustelo,X.R. and Freire,M.
  TITLE    The expression of prothymosin alpha gene in T lymphocytes and
           leukemic lymphoid cells is tied to lymphocyte proliferation
  JOURNAL  J. Biol. Chem. 264 (15), 8451-8454 (1989)
  MEDLINE  89255289
  PUBMED   2785990
REFERENCE  12 (residues 1 to 110)
  AUTHORS  Eschenfeldt,W.H., Manrow,R.E., Krug,M.S. and Berger,S.L.
  TITLE    Isolation and partial sequencing of the human prothymosin alpha
           gene family. Evidence against export of the gene products
  JOURNAL  J. Biol. Chem. 264 (13), 7546-7555 (1989)
```

FIG. 13B CONT'D

```
  MEDLINE   89214202
   PUBMED   2708378
REFERENCE   13 (residues 1 to 110)
  AUTHORS   Eschenfeldt,W.H. and Berger,S.L.
  TITLE     The human prothymosin alpha gene is polymorphic and induced upon
            growth stimulation: evidence using a cloned cDNA
  JOURNAL   Proc. Natl. Acad. Sci. U.S.A. 83 (24), 9403-9407 (1986)
  MEDLINE   87092260
   PUBMED   3457312
REFERENCE   14 (residues 1 to 110)
  AUTHORS   Goodall,G.J., Dominguez,F. and Horecker,B.L.
  TITLE     Molecular cloning of cDNA for human prothymosin alpha
  JOURNAL   Proc. Natl. Acad. Sci. U.S.A. 83 (23), 8926-8928 (1986)
  MEDLINE   87067426
   PUBMED   3466166
COMMENT     PROVISIONAL REFSEQ: This record has not yet been subject to final
            NCBI review. The reference sequence was derived from BC022433.1.
            On Jun 9, 2002 this sequence version replaced gi:4506277.
FEATURES             Location/Qualifiers
     source          1..110
                     /organism="Homo sapiens"
                     /db_xref="taxon:9606"
                     /chromosome="2"
                     /map="2q35-q36"
     Protein         1..110
                     /product="prothymosin, alpha (gene sequence 28)"
                     /note="prothymosin alpha; prothymosin alpha protein"
     CDS             1..110
                     /gene="PTMA"
                     /coded_by="NM_002823.2:182..514"
                     /note="go_component: nucleus [goid 0005634] [evidence TAS]
                     [pmid 10854063];
                     go_process: development [goid 0007275] [evidence NR];
                     go_process: transcription [goid 0006350] [evidence TAS]
                     [pmid 10854063];
                     go_process: regulation of cell cycle [goid 0000074]
                     [evidence NR]"
                     /db_xref="GeneID:5757"
                     /db_xref="MIM:188390"
ORIGIN
        1 msdaavdtss eittkdlkek kevveeaeng rdapangnan eengeqeadn evdeeeeegg
       61 eeeeeeeegd geeeggdede eaesatgkra aeddeddvd tkkqktdedd
```

Disclaimer | Write to the Help Desk
NCBI | NLM | NIH

FIG. 14

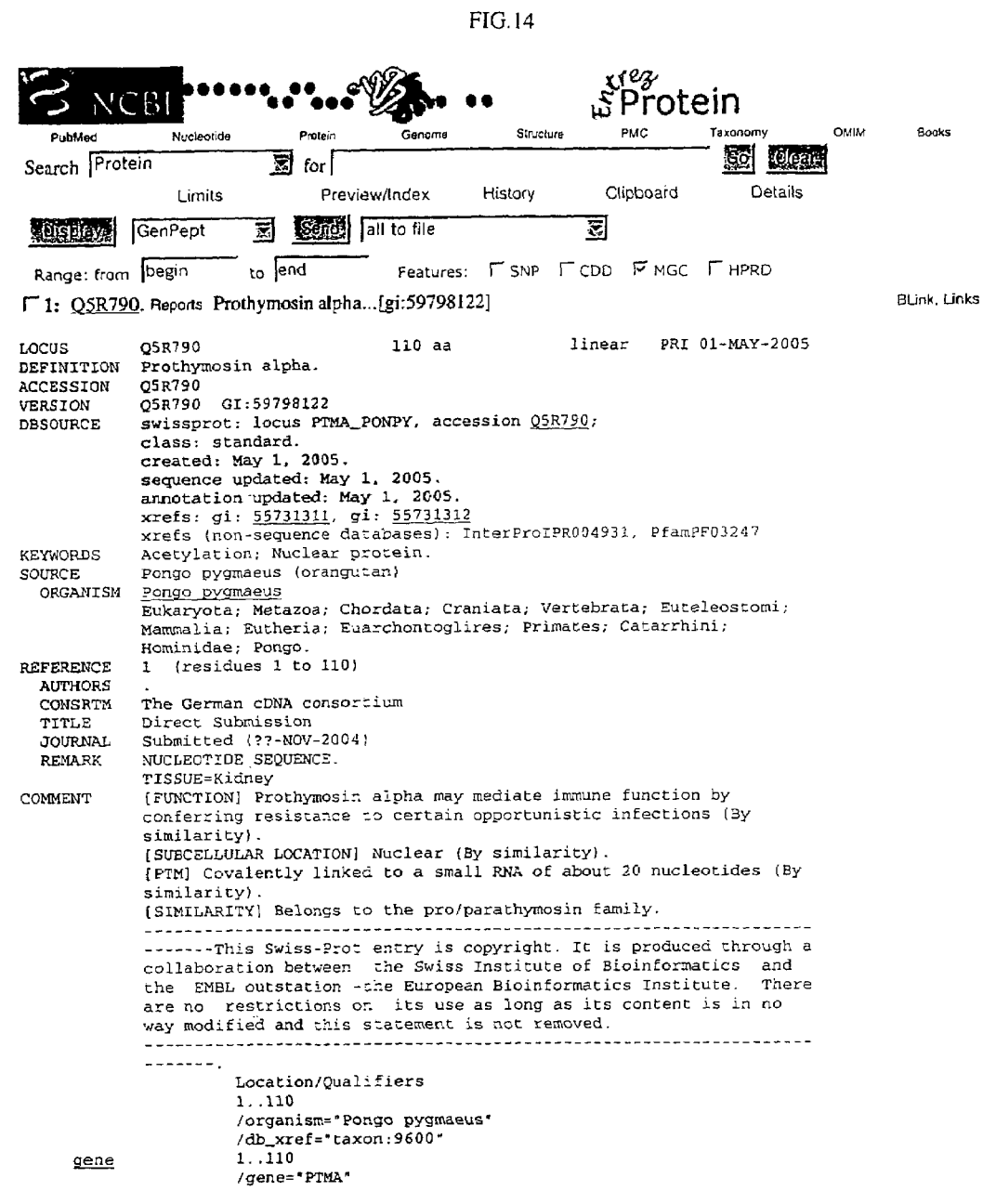

NCBI Entrez Protein

PubMed Nucleotide Protein Genome Structure PMC Taxonomy OMIM Books

Search Protein for Go Clear

Limits Preview/Index History Clipboard Details

Display GenPept Send all to file

Range: from begin to end Features: SNP CDD MGC HPRD

1: Q5R790. Reports Prothymosin alpha...[gi:59798122] BLink, Links

```
LOCUS       Q5R790                110 aa            linear   PRI 01-MAY-2005
DEFINITION  Prothymosin alpha.
ACCESSION   Q5R790
VERSION     Q5R790  GI:59798122
DBSOURCE    swissprot: locus PTMA_PONPY, accession Q5R790;
            class: standard.
            created: May 1, 2005.
            sequence updated: May 1, 2005.
            annotation updated: May 1, 2005.
            xrefs: gi: 55731311, gi: 55731312
            xrefs (non-sequence databases): InterProIPR004931, PfamPF03247
KEYWORDS    Acetylation; Nuclear protein.
SOURCE      Pongo pygmaeus (orangutan)
  ORGANISM  Pongo pygmaeus
            Eukaryota; Metazoa; Chordata; Craniata; Vertebrata; Euteleostomi;
            Mammalia; Eutheria; Euarchontoglires; Primates; Catarrhini;
            Hominidae; Pongo.
REFERENCE   1  (residues 1 to 110)
  AUTHORS   .
  CONSRTM   The German cDNA consortium
  TITLE     Direct Submission
  JOURNAL   Submitted (??-NOV-2004)
  REMARK    NUCLEOTIDE SEQUENCE.
            TISSUE=Kidney
COMMENT     [FUNCTION] Prothymosin alpha may mediate immune function by
            conferring resistance to certain opportunistic infections (By
            similarity).
            [SUBCELLULAR LOCATION] Nuclear (By similarity).
            [PTM] Covalently linked to a small RNA of about 20 nucleotides (By
            similarity).
            [SIMILARITY] Belongs to the pro/parathymosin family.
            ------------------------------------------------------------
            -------This Swiss-Prot entry is copyright. It is produced through a
            collaboration between  the Swiss Institute of Bioinformatics  and
            the  EMBL outstation -the European Bioinformatics Institute.  There
            are no  restrictions on  its use as long as its content is in no
            way modified and this statement is not removed.
            ------------------------------------------------------------
            -------.
                     Location/Qualifiers
                     1..110
                     /organism="Pongo pygmaeus"
                     /db_xref="taxon:9600"
     gene            1..110
                     /gene="PTMA"
```

FIG.14 CONT'D

```
     Protein         1..110
                     /gene="PTMA"
                     /product="Prothymosin alpha"
     Site            2
                     /gene="PTMA"
                     /site_type="modified"
                     /note="N-acetylserine (By similarity).
                     /evidence=experimental
ORIGIN
        1 msdaavdtss eittkdlkek kevveeaeng rdvpangnan eengeqeadn evdeeeeegg
       61 eeeeeeeegd geeedgdede eaesatgkra aeddedddvd tkkqktdedd
```

Disclaimer | Write to the Help Desk
NCBI | NLM | NIH

FIG. 15

NCBI Entrez Protein

PubMed Nucleotide Protein Genome Structure PMC Taxonomy OMIM Books

Search Protein for Go Clear

Limits Preview/Index History Clipboard Details

Display GenPept Send all to file

Range: from begin to end Features: SNP CDD MGC HPRD

1: P26350. Reports Prothymosin alpha...[gi:135835] BLink, Links

```
LOCUS       P26350                  111 aa            linear   ROD 01-MAY-2005
DEFINITION  Prothymosin alpha.
ACCESSION   P26350
VERSION     P26350   GI:135835
DBSOURCE    swissprot: locus PTMA_MOUSE, accession P26350;
            class: standard.
            created: May 1, 1992.
            sequence updated: May 1, 1992.
            annotation updated: May 1, 2005.
            xrefs: gi: 54796, gi: 54797, gi: 26332365, gi: 26332366, gi:
            26351008, gi: 26351009, gi: 51859030, gi: 51859031, gi: 52789487,
            gi: 52789488, gi: 110897
            xrefs (non-sequence databases): EnsemblENSMUSG00000055659,
            MGI97803, InterProIPR004931, PfamPF03247
KEYWORDS    Acetylation; Direct protein sequencing; Nuclear protein.
SOURCE      Mus musculus (house mouse)
  ORGANISM  Mus musculus
            Eukaryota; Metazoa; Chordata; Craniata; Vertebrata; Euteleostomi;
            Mammalia; Eutheria; Euarchontoglires; Glires; Rodentia;
            Sciurognathi; Muridae; Murinae; Mus.
REFERENCE   1  (residues 1 to 111)
  AUTHORS   Low,T.L., Pan,T.L. and Lin,Y.S.
  TITLE     Depression of prothymosin alpha production in murine thymus
            correlates with staphylococcal enterotoxin-B-induced
            immunosuppression [corrected]
  JOURNAL   FEBS Lett. 273 (1-2), 1-5 (1990)
   PUBMED   2226839
  REMARK    PROTEIN SEQUENCE.
REFERENCE   2  (residues 1 to 111)
  AUTHORS   Schmidt,G. and Werner,D.
  TITLE     Nucleotide sequence of the murine prothymosin alpha cDNA and its
            deduced primary and secondary protein structure
  JOURNAL   Biochim. Biophys. Acta 1088 (3), 442-444 (1991)
   PUBMED   2015308
  REMARK    NUCLEOTIDE SEQUENCE.
REFERENCE   3  (residues 1 to 111)
  AUTHORS   Okazaki,Y., Furuno,M., Kasukawa,T., Adachi,J., Bono,H., Kondo,S.,
            Nikaido,I., Osato,N., Saito,R., Suzuki,H., Yamanaka,I.,
            Kiyosawa,H., Yagi,K., Tomaru,Y., Hasegawa,Y., Nogami,A.,
            Schonbach,C., Gojobori,T., Baldarelli,R., Hill,D.P., Bult,C.,
            Hume,D.A., Quackenbush,J., Schriml,L.M., Kanapin,A., Matsuda,H.,
            Batalov,S., Beisel,K.W., Blake,J.A., Bradt,D., Brusic,V.,
            Chothia,C., Corbani,L.E., Cousins,S., Dalla,E., Dragani,T.A.,
            Fletcher,C.F., Forrest,A., Frazer,K.S., Gaasterland,T.,
            Gariboldi,M., Gissi,C., Godzik,A., Gough,J., Grimmond,S.,
```

NCBI Sequence Viewer v2.0

FIG. 15 CONT'D

```
            Gustincich,S., Hirokawa,N., Jackson,I.J., Jarvis,E.D., Kanai,A.,
            Kawaji,H., Kawasawa,Y., Kedzierski,R.M., King,B.L., Konagaya,A.,
            Kurochkin,I.V., Lee,Y., Lenhard,B., Lyons,P.A., Maglott,D.R.,
            Maltais,L., Marchionni,L., McKenzie,L., Miki,H., Nagashima,T.,
            Numata,K., Okido,T., Pavan,W.J., Pertea,G., Pesole,G.,
            Petrovsky,N., Pillai,R., Pontius,J.U., Qi,D., Ramachandran,S.,
            Ravasi,T., Reed,J.C., Reed,D.J., Reid,J., Ring,B.Z., Ringwald,M.,
            Sandelin,A., Schneider,C., Semple,C.A., Setou,M., Shimada,K.,
            Sultana,R., Takenaka,Y., Taylor,M.S., Teasdale,R.D., Tomita,M.,
            Verardo,R., Wagner,L., Wahlestedt,C., Wang,Y., Watanabe,Y.,
            Wells,C., Wilming,L.G., Wynshaw-Boris,A., Yanagisawa,M., Yang,I.,
            Yang,L., Yuan,Z., Zavolan,M., Zhu,Y., Zimmer,A., Carninci,P.,
            Hayatsu,N., Hirozane-Kishikawa,T., Konno,H., Nakamura,M.,
            Sakazume,N., Sato,K., Shiraki,T., Waki,K., Kawai,J., Aizawa,K.,
            Arakawa,T., Fukuda,S., Hara,A., Hashizume,W., Imotani,K., Ishii,Y.,
            Itoh,M., Kagawa,I., Miyazaki,A., Sakai,K., Sasaki,D., Shibata,K.,
            Shinagawa,A., Yasunishi,A., Yoshino,M., Waterston,R., Lander,E.S.,
            Rogers,J., Birney,E. and Hayashizaki,Y.
  TITLE     Analysis of the mouse transcriptome based on functional annotation
            of 60,770 full-length cDNAs
  JOURNAL   Nature 420 (6915), 563-573 (2002)
   PUBMED   12466851
  REMARK    NUCLEOTIDE SEQUENCE.
            STRAIN=C57BL/6J; TISSUE=Eye, and Thymus
REFERENCE   4 (residues 1 to 111)
  AUTHORS   Strausberg,R.L., Feingold,E.A., Grouse,L.H., Derge,J.G.,
            Klausner,R.D., Collins,F.S., Wagner,L., Shenmen,C.M., Schuler,G.D.,
            Altschul,S.F., Zeeberg,B., Buetow,K.H., Schaefer,C.F., Bhat,N.K.,
            Hopkins,R.F., Jordan,H., Moore,T., Max,S.I., Wang,J., Hsieh,F.,
            Diatchenko,L., Marusina,K., Farmer,A.A., Rubin,G.M., Hong,L.,
            Stapleton,M., Soares,M.B., Bonaldo,M.F., Casavant,T.L.,
            Scheetz,T.E., Brownstein,M.J., Usdin,T.B., Toshiyuki,S.,
            Carninci,P., Prange,C., Raha,S.S., Loquellano,N.A., Peters,G.J.,
            Abramson,R.D., Mullahy,S.J., Bosak,S.A., McEwan,P.J.,
            McKernan,K.J., Malek,J.A., Gunaratne,P.H., Richards,S.,
            Worley,K.C., Hale,S., Garcia,A.M., Gay,L.J., Hulyk,S.W.,
            Villalon,D.K., Muzny,D.M., Sodergren,E.J., Lu,X., Gibbs,R.A.,
            Fahey,J., Helton,E., Ketteman,M., Madan,A., Rodrigues,S.,
            Sanchez,A., Whiting,M., Madan,A., Young,A.C., Shevchenko,Y.,
            Bouffard,G.G., Blakesley,R.W., Touchman,J.W., Green,E.D.,
            Dickson,M.C., Rodriguez,A.C., Grimwood,J., Schmutz,J., Myers,R.M.,
            Butterfield,Y.S., Krzywinski,M.I., Skalska,U., Smailus,D.E.,
            Schnerch,A., Schein,J.E., Jones,S.J. and Marra,M.A.
  TITLE     Generation and initial analysis of more than 15,000 full-length
            human and mouse cDNA sequences
  JOURNAL   Proc. Natl. Acad. Sci. U.S.A. 99 (26), 16899-16903 (2002)
   PUBMED   12477932
  REMARK    NUCLEOTIDE SEQUENCE [LARGE SCALE MRNA].
            STRAIN=C57BL/6; TISSUE=Brain, and Limb
REFERENCE   5 (residues 1 to 111)
  AUTHORS   Makarova,T., Grebenshikov,N., Egorov,C., Vartapetian,A. and
            Bogdanov,A.
  TITLE     Prothymosin alpha is an evolutionary conserved protein covalently
            linked to a small RNA
  JOURNAL   FEBS Lett. 257 (2), 247-250 (1989)
   PUBMED   2479575
  REMARK    PROTEIN SEQUENCE OF 14-17; 21-67 AND 90-102.
COMMENT     [FUNCTION] Prothymosin alpha may mediate immune function by
            conferring resistance to certain opportunistic infections.
            [SUBCELLULAR LOCATION] Nuclear.
```

FIG. 15 CONT'D

```
          [PTM] Covalently linked to a small RNA of about 20 nucleotides.
          [SIMILARITY] Belongs to the pro/parathymosin family.
          -----------------------------------------------------------------
          -------This Swiss-Prot entry is copyright. It is produced through a
          collaboration between  the Swiss Institute of Bioinformatics  and
          the  EMBL outstation -the European Bioinformatics Institute.  There
          are no  restrictions on  its use as long as its content is in no
          way modified and this statement is not removed.
          -----------------------------------------------------------------
          -------.
FEATURES             Location/Qualifiers
     source          1..111
                     /organism="Mus musculus"
                     /db_xref="taxon:10090"
     gene            1..111
                     /gene="Ptma"
     Protein         1..111
                     /gene="Ptma"
                     /product="Prothymosin alpha"
     Region          2..29
                     /gene="Ptma"
                     /region_name="Processed active peptide"
                     /note="Thymosin alpha."
                     /evidence=experimental
     Site            2
                     /gene="Ptma"
                     /site_type="modified"
                     /note="N-acetylserine (By similarity).
                     /evidence=experimental
     Region          42..101
                     /gene="Ptma"
                     /region_name="Domain"
                     /note="Asp/Glu-rich (acidic)."
                     /evidence=experimental
     Region          106
                     /gene="Ptma"
                     /region_name="Conflict"
                     /note="K -> KK (in Ref. 1)."
                     /evidence=experimental
ORIGIN
        1 msdaavdtss eittkdlkek kevveeaeng rdapangnaq neengeqead nevdeeeeeg
       61 geeeeeeeeg dgeeedgded eeaeaptgkr vaeddedddv dtkkqkteed d
```

FIG. 16

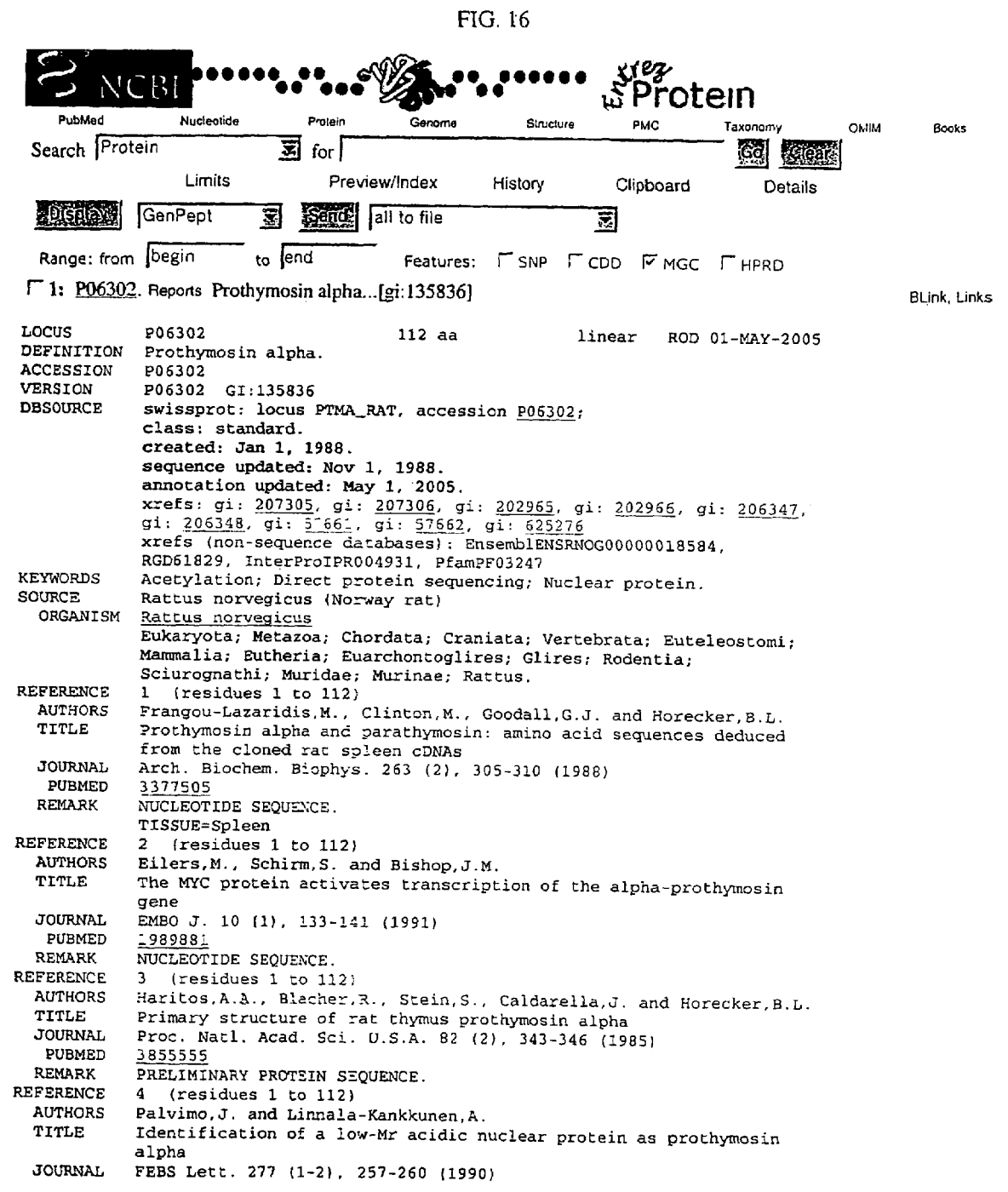

NCBI Entrez Protein

PubMed Nucleotide Protein Genome Structure PMC Taxonomy OMIM Books

Search Protein for Go Clear

Limits Preview/Index History Clipboard Details

Display GenPept Send all to file

Range: from begin to end Features: SNP CDD MGC HPRD

1: P06302. Reports Prothymosin alpha...[gi:135836] BLink, Links

```
LOCUS       P06302                  112 aa            linear   ROD 01-MAY-2005
DEFINITION  Prothymosin alpha.
ACCESSION   P06302
VERSION     P06302  GI:135836
DBSOURCE    swissprot: locus PTMA_RAT, accession P06302;
            class: standard.
            created: Jan 1, 1988.
            sequence updated: Nov 1, 1988.
            annotation updated: May 1, 2005.
            xrefs: gi: 207305, gi: 207306, gi: 202965, gi: 202966, gi: 206347,
            gi: 206348, gi: 57661, gi: 57662, gi: 625276
            xrefs (non-sequence databases): EnsemblENSRNOG00000018584,
            RGD61829, InterProIPR004931, PfamPF03247
KEYWORDS    Acetylation; Direct protein sequencing; Nuclear protein.
SOURCE      Rattus norvegicus (Norway rat)
  ORGANISM  Rattus norvegicus
            Eukaryota; Metazoa; Chordata; Craniata; Vertebrata; Euteleostomi;
            Mammalia; Eutheria; Euarchontoglires; Glires; Rodentia;
            Sciurognathi; Muridae; Murinae; Rattus.
REFERENCE   1  (residues 1 to 112)
  AUTHORS   Frangou-Lazaridis,M., Clinton,M., Goodall,G.J. and Horecker,B.L.
  TITLE     Prothymosin alpha and parathymosin: amino acid sequences deduced
            from the cloned rat spleen cDNAs
  JOURNAL   Arch. Biochem. Biophys. 263 (2), 305-310 (1988)
   PUBMED   3377505
  REMARK    NUCLEOTIDE SEQUENCE.
            TISSUE=Spleen
REFERENCE   2  (residues 1 to 112)
  AUTHORS   Eilers,M., Schirm,S. and Bishop,J.M.
  TITLE     The MYC protein activates transcription of the alpha-prothymosin
            gene
  JOURNAL   EMBO J. 10 (1), 133-141 (1991)
   PUBMED   1989881
  REMARK    NUCLEOTIDE SEQUENCE.
REFERENCE   3  (residues 1 to 112)
  AUTHORS   Haritos,A.A., Blacher,R., Stein,S., Caldarella,J. and Horecker,B.L.
  TITLE     Primary structure of rat thymus prothymosin alpha
  JOURNAL   Proc. Natl. Acad. Sci. U.S.A. 82 (2), 343-346 (1985)
   PUBMED   3855555
  REMARK    PRELIMINARY PROTEIN SEQUENCE.
REFERENCE   4  (residues 1 to 112)
  AUTHORS   Palvimo,J. and Linnala-Kankkunen,A.
  TITLE     Identification of a low-Mr acidic nuclear protein as prothymosin
            alpha
  JOURNAL   FEBS Lett. 277 (1-2), 257-260 (1990)
```

FIG. 16 CONT'D

```
  PUBMED    2269362
  REMARK    PARTIAL PROTEIN SEQUENCE.
 COMMENT    [FUNCTION] Prothymosin alpha may mediate immune function by
            conferring resistance to certain opportunistic infections.
            [SUBCELLULAR LOCATION] Nuclear.
            [PTM] Covalently linked to a small RNA of about 20 nucleotides (By
            similarity).
            [SIMILARITY] Belongs to the pro/parathymosin family.
            --------------------------------------------------------------
            -------This Swiss-Prot entry is copyright. It is produced through a
            collaboration between the Swiss Institute of Bioinformatics and
            the EMBL outstation -the European Bioinformatics Institute. There
            are no restrictions on its use as long as its content is in no
            way modified and this statement is not removed.
            --------------------------------------------------------------
            -------.
FEATURES             Location/Qualifiers
     source          1..112
                     /organism="Rattus norvegicus"
                     /db_xref="taxon:10116"
     gene            1..112
                     /gene="Ptma"
     Protein         1..112
                     /gene="Ptma"
                     /product="Prothymosin alpha"
     Region          2..29
                     /gene="Ptma"
                     /region_name="Processed active peptide"
                     /note="Thymosin alpha."
                     /evidence=experimental
     Site            2
                     /gene="Ptma"
                     /site_type="modified"
                     /note="N-acetylserine."
                     /evidence=experimental
     Region          42..101
                     /gene="Ptma"
                     /region_name="Domain"
                     /note="Asp/Glu-rich (acidic)."
                     /evidence=experimental
ORIGIN
        1 msdaavdtss eittkdlkek kevveeaeng rdapangnaq neengeqead nevdeeeeeg
       61 geeeeeeeeg dgeeedgded eeaeaptgkr vaeddedddv etkkqkktde dd
```

FIG. 17

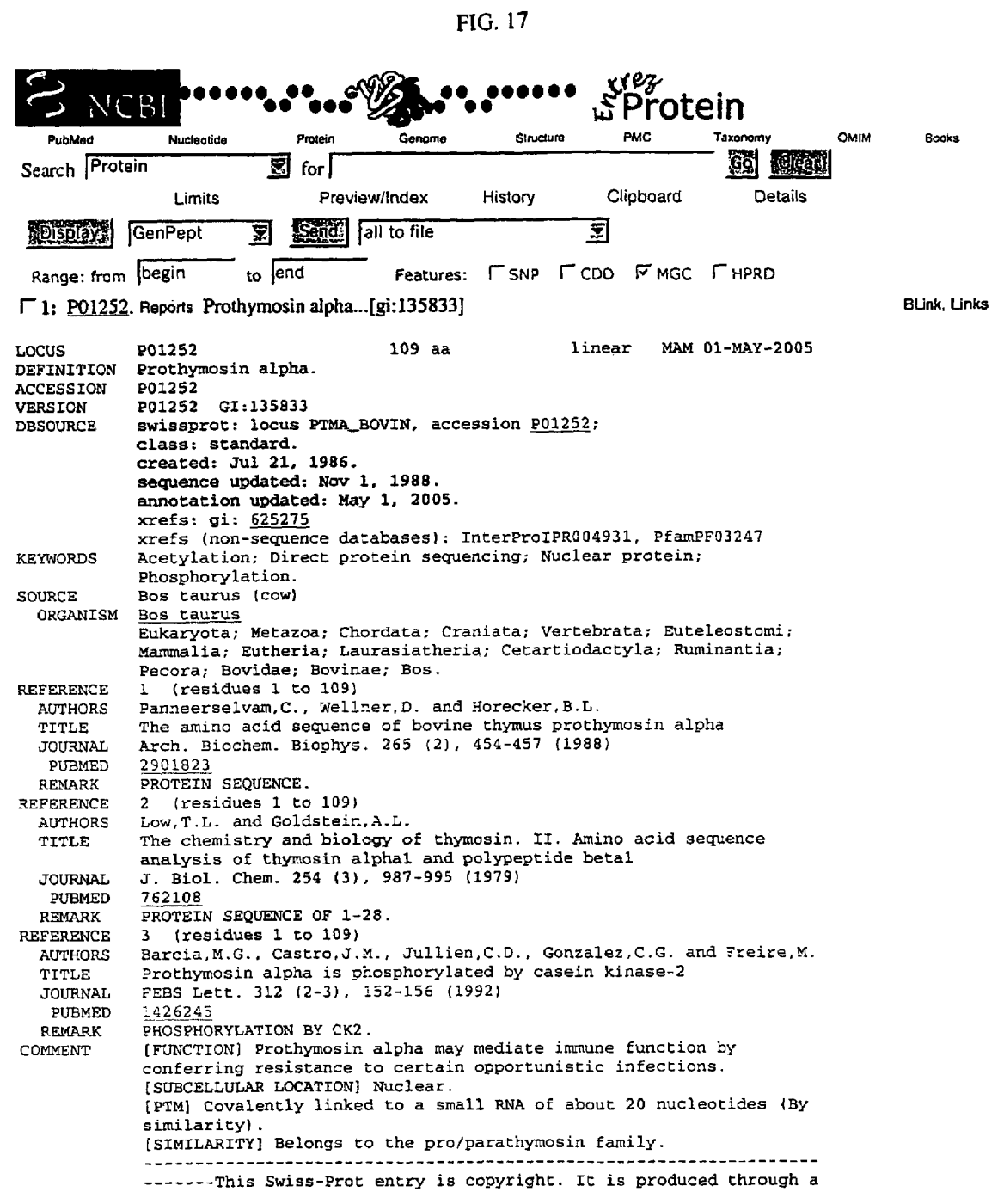

NCBI Protein

PubMed Nucleotide Protein Genome Structure PMC Taxonomy OMIM Books

Search Protein for Go Clear

Limits Preview/Index History Clipboard Details

Display GenPept Send all to file

Range: from begin to end Features: SNP CDD MGC HPRD

1: P01252. Reports Prothymosin alpha...[gi:135833] BLink, Links

```
LOCUS       P01252                  109 aa            linear   MAM 01-MAY-2005
DEFINITION  Prothymosin alpha.
ACCESSION   P01252
VERSION     P01252  GI:135833
DBSOURCE    swissprot: locus PTMA_BOVIN, accession P01252;
            class: standard.
            created: Jul 21, 1986.
            sequence updated: Nov 1, 1988.
            annotation updated: May 1, 2005.
            xrefs: gi: 625275
            xrefs (non-sequence databases): InterProIPR004931, PfamPF03247
KEYWORDS    Acetylation; Direct protein sequencing; Nuclear protein;
            Phosphorylation.
SOURCE      Bos taurus (cow)
  ORGANISM  Bos taurus
            Eukaryota; Metazoa; Chordata; Craniata; Vertebrata; Euteleostomi;
            Mammalia; Eutheria; Laurasiatheria; Cetartiodactyla; Ruminantia;
            Pecora; Bovidae; Bovinae; Bos.
REFERENCE   1  (residues 1 to 109)
  AUTHORS   Panneerselvam,C., Wellner,D. and Horecker,B.L.
  TITLE     The amino acid sequence of bovine thymus prothymosin alpha
  JOURNAL   Arch. Biochem. Biophys. 265 (2), 454-457 (1988)
   PUBMED   2901823
  REMARK    PROTEIN SEQUENCE.
REFERENCE   2  (residues 1 to 109)
  AUTHORS   Low,T.L. and Goldstein,A.L.
  TITLE     The chemistry and biology of thymosin. II. Amino acid sequence
            analysis of thymosin alpha1 and polypeptide beta1
  JOURNAL   J. Biol. Chem. 254 (3), 987-995 (1979)
   PUBMED   762108
  REMARK    PROTEIN SEQUENCE OF 1-28.
REFERENCE   3  (residues 1 to 109)
  AUTHORS   Barcia,M.G., Castro,J.M., Jullien,C.D., Gonzalez,C.G. and Freire,M.
  TITLE     Prothymosin alpha is phosphorylated by casein kinase-2
  JOURNAL   FEBS Lett. 312 (2-3), 152-156 (1992)
   PUBMED   1426245
  REMARK    PHOSPHORYLATION BY CK2.
COMMENT     [FUNCTION] Prothymosin alpha may mediate immune function by
            conferring resistance to certain opportunistic infections.
            [SUBCELLULAR LOCATION] Nuclear.
            [PTM] Covalently linked to a small RNA of about 20 nucleotides (By
            similarity).
            [SIMILARITY] Belongs to the pro/parathymosin family.
            ------------------------------------------------------------------
            -------This Swiss-Prot entry is copyright. It is produced through a
```

FIG. 17 CONT'D

```
          collaboration between  the Swiss Institute of Bioinformatics  and
          the  EMBL outstation -the European Bioinformatics Institute.  There
          are no  restrictions on  its use as long as its content is in no
          way modified and this statement is not removed.
          -------------------------------------------------------------------
          -------.
FEATURES             Location/Qualifiers
     source          1..109
                     /organism="Bos taurus"
                     /db_xref="taxon:9913"
     gene            1..109
                     /gene="PTMA"
     Protein         1..109
                     /gene="PTMA"
                     /product="Prothymosin alpha"
     Region          1..28
                     /gene="PTMA"
                     /region_name="Processed active peptide"
                     /note="Thymosin alpha-1."
                     /evidence=experimental
     Site            1
                     /gene="PTMA"
                     /site_type="modified"
                     /note="N-acetylserine."
                     /evidence=experimental
     Site            7
                     /gene="PTMA"
                     /site_type="modified"
                     /note="Phosphothreonine (by CK2)."
                     /evidence=experimental
     Site            12
                     /gene="PTMA"
                     /site_type="modified"
                     /note="Phosphothreonine (by CK2)."
                     /evidence=experimental
     Site            13
                     /gene="PTMA"
                     /site_type="modified"
                     /note="Phosphothreonine (by CK2)."
                     /evidence=experimental
     Region          40..99
                     /gene="PTMA"
                     /region_name="Domain
                     /note="Asp/Glu-rich (acidic).
                     /evidence=experimental
ORIGIN
        1 sdaavdtsse ittkdlkekk evveeaengr eapangnane engeqeadne vdeeeeegge
       61 eeeeeeegdg eeedgdedee aeaatgkraa eddedddvdt kkqktdedd
```

FIG. 18

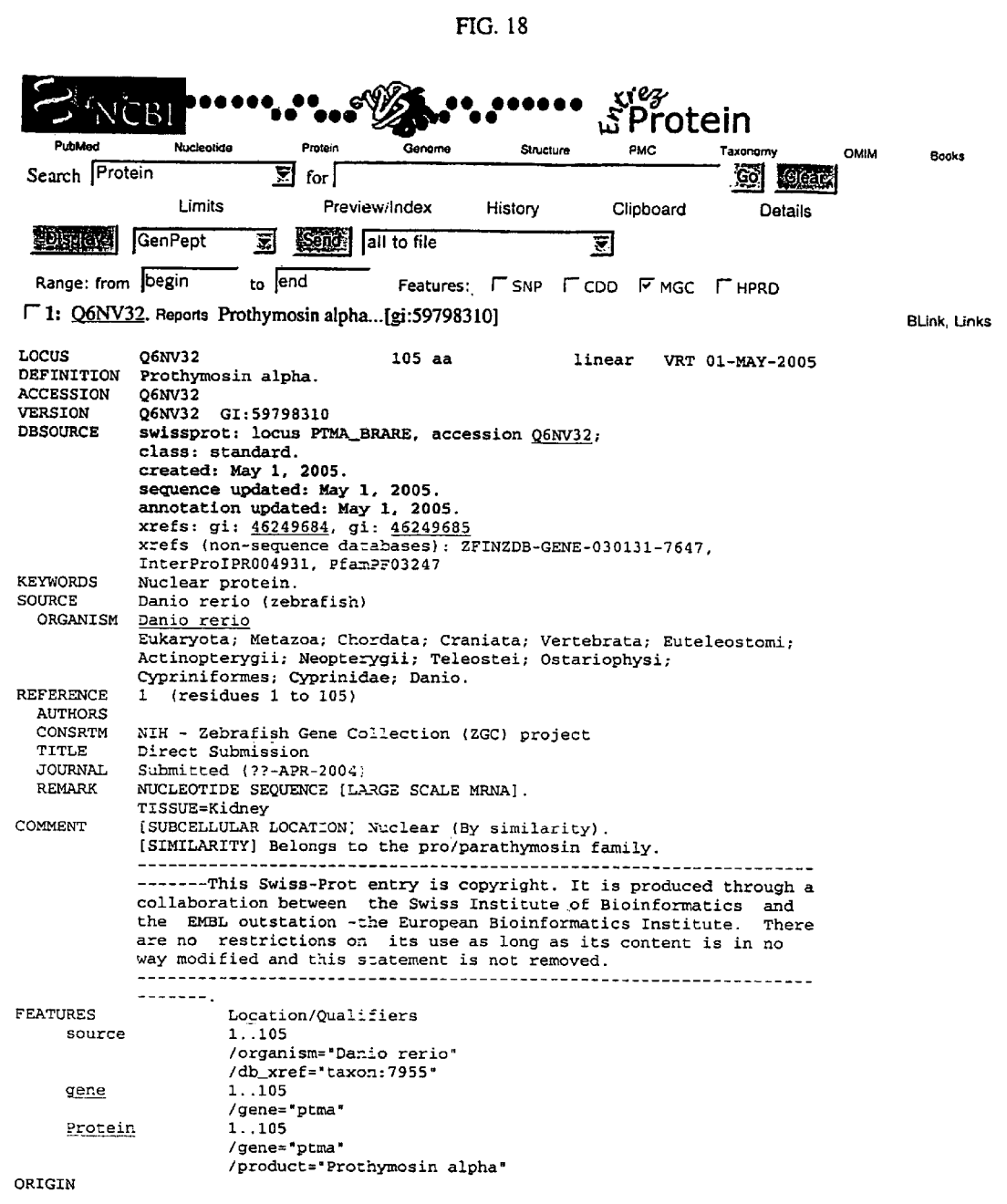

```
LOCUS       Q6NV32                  105 aa            linear   VRT 01-MAY-2005
DEFINITION  Prothymosin alpha.
ACCESSION   Q6NV32
VERSION     Q6NV32  GI:59798310
DBSOURCE    swissprot: locus PTMA_BRARE, accession Q6NV32;
            class: standard.
            created: May 1, 2005.
            sequence updated: May 1, 2005.
            annotation updated: May 1, 2005.
            xrefs: gi: 46249684, gi: 46249685
            xrefs (non-sequence databases): ZFINZDB-GENE-030131-7647,
            InterProIPR004931, PfamPF03247
KEYWORDS    Nuclear protein.
SOURCE      Danio rerio (zebrafish)
  ORGANISM  Danio rerio
            Eukaryota; Metazoa; Chordata; Craniata; Vertebrata; Euteleostomi;
            Actinopterygii; Neopterygii; Teleostei; Ostariophysi;
            Cypriniformes; Cyprinidae; Danio.
REFERENCE   1  (residues 1 to 105)
  AUTHORS
  CONSRTM   NIH - Zebrafish Gene Collection (ZGC) project
  TITLE     Direct Submission
  JOURNAL   Submitted (??-APR-2004)
  REMARK    NUCLEOTIDE SEQUENCE [LARGE SCALE MRNA].
            TISSUE=Kidney
COMMENT     [SUBCELLULAR LOCATION] Nuclear (By similarity).
            [SIMILARITY] Belongs to the pro/parathymosin family.
            -----------------------------------------------------------------
            -------This Swiss-Prot entry is copyright. It is produced through a
            collaboration between  the Swiss Institute of Bioinformatics  and
            the  EMBL outstation -the European Bioinformatics Institute.  There
            are no  restrictions on  its use as long as its content is in no
            way modified and this statement is not removed.
            -----------------------------------------------------------------
            -------.
FEATURES             Location/Qualifiers
     source          1..105
                     /organism="Danio rerio"
                     /db_xref="taxon:7955"
     gene            1..105
                     /gene="ptma"
     Protein         1..105
                     /gene="ptma"
                     /product="Prothymosin alpha"
ORIGIN
```

FIG. 18 CONT'D

```
 1 madtkvdtsk evsakdlkek kqveeaengk dapangnaen eengdqenev deedddvaee
61 deeddgegdd ddedeeaegg tgkraaeddd ddeddvdpkk qktdv
```

FIG. 19

NCBI Entrez Protein

PubMed Nucleotide Protein Genome Structure PMC Taxonomy OMIM Books

Search Protein for Go Clear

Limits Preview/Index History Clipboard Details

Display GenPept Send all to file

Range: from begin to end Features: SNP CDD MGC HPRD

1: Q90ZK2. Reports Prothymosin alpha...[gi:59798424] BLink, Links

```
LOCUS       Q90ZK2                109 aa          linear   VRT 01-MAY-2005
DEFINITION  Prothymosin alpha (Prot-alpha).
ACCESSION   Q90ZK2
VERSION     Q90ZK2  GI:59798424
DBSOURCE    swissprot: locus PTMA_RANES, accession Q90ZK2;
            class: standard.
            created: May 1, 2005.
            sequence updated: May 1, 2005.
            annotation updated: May 1, 2005.
            xrefs: gi: 14268470, gi: 14268471
            xrefs (non-sequence databases): InterProIPR004931, PfamPF03247
KEYWORDS    Nuclear protein.
SOURCE      Rana esculenta (edible frog)
  ORGANISM  Rana esculenta
            Eukaryota; Metazoa; Chordata; Craniata; Vertebrata; Euteleostomi;
            Amphibia; Batrachia; Anura; Neobatrachia; Ranoidea; Ranidae; Rana;
            Pelophylax.
REFERENCE   1  (residues 1 to 109)
  AUTHORS   Aniello,F., Branno,M., De Rienzo,G., Ferrara,D., Palmiero,C. and
            Minucci,S.
  TITLE     First evidence of prothymosin alpha in a non-mammalian vertebrate
            and its involvement in the spermatogenesis of the frog Rana
            esculenta
  JOURNAL   Mech. Dev. 110 (1-2), 213-217 (2002)
   PUBMED   11744386
  REMARK    NUCLEOTIDE SEQUENCE.
            TISSUE=Testis
COMMENT     [FUNCTION] May have role in testicular activity.
            [SUBCELLULAR LOCATION] Nuclear (By similarity).
            [TISSUE SPECIFICITY] Highly expressed in the testis.
            [DEVELOPMENTAL STAGE] Expression peaks in September/October in
            concomitance with germ cell maturation.
            [SIMILARITY] Belongs to the pro/parathymosin family.
            ------------------------------------------------------------
            -------This Swiss-Prot entry is copyright. It is produced through a
            collaboration between the Swiss Institute of Bioinformatics and
            the EMBL outstation -the European Bioinformatics Institute. There
            are no restrictions on its use as long as its content is in no
            way modified and this statement is not removed.
            ------------------------------------------------------------
            -------.
FEATURES             Location/Qualifiers
     source          1..109
                     /organism="Rana esculenta"
                     /db_xref="taxon:8401"
```

FIG. 19 CONT'D

```
     Protein          1..109
                      /product="Prothymosin alpha"
ORIGIN
        1 msdtsvdasv ekttkdlksk dkelveeten gkdkpangna eneengedga dneeeeevde
       61 edeedegegd ddegdeddea dgatgkraae dddedddvda kkqktdddd
```

METHODS OF INHIBITING VIRAL INFECTION

CROSS-REFERENCE TO RELATED APPLICATIONS

This application claims priority under 35 USC 119(e) from U.S. Provisional Application Ser. No. 60/655,924, filed Feb. 24, 2005, which application is herein specifically incorporated by reference in its entirety.

FIELD OF THE INVENTION

The present invention pertains to the fields of molecular biology and methods for inhibiting infectious disease. More specifically, the invention relates to methods of inhibiting (e.g., preventing and/or treating) viral infection using prothymosin-alpha (ProTα) molecules. In a particular application, the invention pertains to methods for preventing and/or treating human immunodeficiency virus-1 (HIV-1) infection using ProTα. Methods of making and using prothymosin alpha nucleic and amino acid sequences and compositions thereof are also encompassed by the present invention.

BACKGROUND OF THE INVENTION

Several publications and patent documents are referenced in this application in order to more fully describe the state of the art to which this invention pertains. The disclosure of each of these publications and documents is incorporated by reference herein.

The control of viral infection in HIV-1 positive individuals requires the function of the innate and adaptive arms of the immune system (1, 2). While the induction of antigen specific cytotoxic T lymphocytes (CTL) involved in direct killing of HIV infected cells is the function of the adaptive immune response, the innate immune system is part of the primary defense against pathogenic attack and allows the development of a specific adaptive response (3). CD8+ cells derived from HIV-1 positive and negative donors are thought to contribute to the innate defense as they secrete soluble molecules that inhibit HIV-1 replication in vitro (4-7).

The β chemokines, RANTES, MIP-1α and MIP-1β are active components found in CD8+ cell supernatants that inhibit entry of R5 strains of HIV-1 (8). Another chemokine, macrophage-derived cytokine (MDC), also isolated from CD8+ cell supernantants was reported to have activity against R5 and X4 strains of HIV-1, although synthetic forms have more restricted inhibitory activity (9-11) which may be due to necessary processing (11). The CXCR4 ligand, stromal-derived factor (SDF1) blocks entry of X4 viruses but is not produced by CD8+ cells (12, 13). IL-16, as well as interferon-α, β, and γ can all be found in variable amounts in CD8+ cell supernatants and exhibit anti-HIV activity, as does the amino terminal fragment of urokinase-type plasminogen activator (uPA) (14-17) and a form of antithrombin III. A number of groups, have shown that the anti-HIV-1 activity found in CD8+ cell supernatants is not fully accounted for by β chemokines, Il-16 or the interferons (4, 18, 19).

In view of the epidemic of diseases caused by HIV-1 infection, there is a need to identify novel preventative and therapeutic agents that can be used to combat HIV-1 transmission and progression of HIV-1 infection and related diseases. As indicated herein above, CD8+ cell supernatants offer a potential source for such preventative and therapeutic agents.

SUMMARY

As described herein, the present inventors have discovered that Prothymosin a (ProTα) exhibits significant HIV-1 inhibitory activity in primary macrophages and dendritic cells (DCs). Specifically, the present inventors demonstrate herein for the first time that either native or recombinant ProTα is a potent inhibitor of HIV-1 LTR driven gene transcription in infected macrophages and dendritic cells (DCs). ProTα is a small (12 KD) highly acidic protein (20-22), which has been previously characterized primarily as a factor that promotes cellular proliferation (22, 24-26). The ability of ProTα to inhibit HIV-1 infection is, therefore, a novel property of ProTα. Thus, the discovery of the present inventors presents ProTα as a valuable therapeutic and/or preventative agent with which to combat infectious diseases, particularly those caused by viral infections.

Inhibitors of the invention, such as ProTα and/or functional derivatives and fragments thereof, and compositions comprising these inhibitors can be administered for preventative and/or therapeutic treatments. In preventative applications, inhibitors or compositions thereof are administered to a patient before potential exposure to an infectious disease so as to partially or completely prevent transmission of the infectious disease. In a particular aspect of the invention, an infectious disease is caused by a virus (such as, e.g., a retrovirus or lentivirus), and inhibitors or compositions thereof are administered to a patient before potential exposure to the virus so as to partially or completely prevent viral infection. In general, prevention of viral infection involves partially or completely inhibiting essential stages of the viral life cycle (e.g., transcription of essential viral genes or viral replication).

In therapeutic applications, inhibitors or compositions thereof are administered to a patient already suffering from an infectious disease to ameliorate or eliminate symptoms associated with the disease. In a particular embodiment, an infectious disease is caused by a virus (such as, e.g., a retrovirus or lentivirus), and inhibitors or compositions thereof are administered to a patient infected with the virus in an amount sufficient to cure or at least partially arrest the symptoms of the disease and its complications.

An amount adequate to accomplish either a preventative or therapeutic goal is defined as a "therapeutically effective amount or dose." Amounts effective for achieving either of these clinical goals will depend on the severity of the disease, with respect to therapeutic applications, the mode of administration (e.g., systemic or topical), and the weight and general state of the patient.

In accordance with the present invention, the instant methods utilize ProTα molecules, including homologs and orthologs, and nucleic acid sequences encoding ProTα molecules for treating and/or preventing infectious diseases. Exemplary sequences of ProTα molecules of the invention are presented in FIGS. 11-19 and these molecules and other related molecules are known to those skilled in the art and can be identified by a review of the available literature. Also encompassed by the invention are methods that call for using functional derivatives and fragments of ProTα and nucleic acid sequences encoding same. The invention is further directed to compositions comprising ProTα molecules and/or functional derivatives and fragments thereof and pharmaceutically acceptable carriers or excipients and to methods for the use of such compositions in the prevention and/or treatment of infectious disease.

The methods of the present invention may be used to advantage for preventing and/or treating a variety of viral infections, including without limitation, any lentiviral or retroviral infection, including, but not limited to, those resulting from HIV-1, HIV-2, simian immunodeficiency virus (SIV), feline immunodeficiency virus (FIV), bovine immunodeficiency virus (BIV), visna virus and all strains and isolates thereof; and hepatitis virus and all strains and isolates thereof.

In a particular embodiment, the present invention is directed to the discovery that ProTα is an inhibitor of HIV infection, which is capable of reducing, eliminating or preventing HIV. The present invention is, therefore, directed to methods of using ProTα molecules, including homologs and orthologs, and nucleic acid sequences encoding ProTα molecules for treating and/or preventing HIV-1 infection. The present methods also encompass use of functional derivatives and fragments of ProTα and nucleic acid sequences encoding same. The invention is further directed to compositions comprising ProTα molecules and/or functional derivatives and fragments thereof and pharmaceutically acceptable carriers or excipients and to methods for the use of such compositions in the prevention and/or treatment of HIV infection. The methods of the present invention may, therefore, be used to advantage for preventing HIV-1 infection and/or treating an established HIV-1 infection, whereby such treatment inhibits HIV-1 life cycle and impairs disease progression.

Inhibitors and compositions of the invention are administered via any standard means and may be administered in a systemic and/or localized manner. Various modes of administration may be evaluated by a skilled practitioner based on a variety of clinical parameters such as the type of infectious disease, the purpose of the administration (e.g., prevention and/or treatment of an infectious disease), and the age, sex, and condition of the subject to be treated using the methods of the invention. Inhibitors and compositions of the invention may, for example, be administered topically, orally, parenterally, or as an aerosol. With respect to the prevention of sexually transmitted infectious diseases, the inhibitors and compositions of the invention may, for example, be administered topically or orally prior to a sexual encounter. Such preventative measures may also involve repeated administration of the inhibitors and compositions of the invention after the sexual encounter.

It will also be appreciated by one skilled in the art that ProTα molecules may be used to advantage as agents that act as general inhibitors of transcription. In particular embodiments, it may be used to inhibit viral transcription.

Although the present methods may be used to particular advantage with respect to infectious agents that infect macrophages and dendritic cells that are important reservoirs of virus in the brain and are leading to HIV-1 associated dementia. It will be appreciated that ProTα molecules may also be used efficaciously in the treatment of other infected cell types.

Subjects that may be treated using the methods of the invention include, without limitation, all mammals. In particular embodiments, the mammal is a primate or a human.

The invention is also directed to a larger family of highly acidic polypeptides that are structurally and functionally related to ProTα. Such molecules are also envisioned for use in the present methods as inhibitors of infectious diseases, particularly those related to viral infection.

Other features and advantages of the invention will be apparent from the following description of the preferred embodiments thereof, and from the claims.

BRIEF DESCRIPTION OF THE DRAWINGS

FIG. 1

Figure 3:
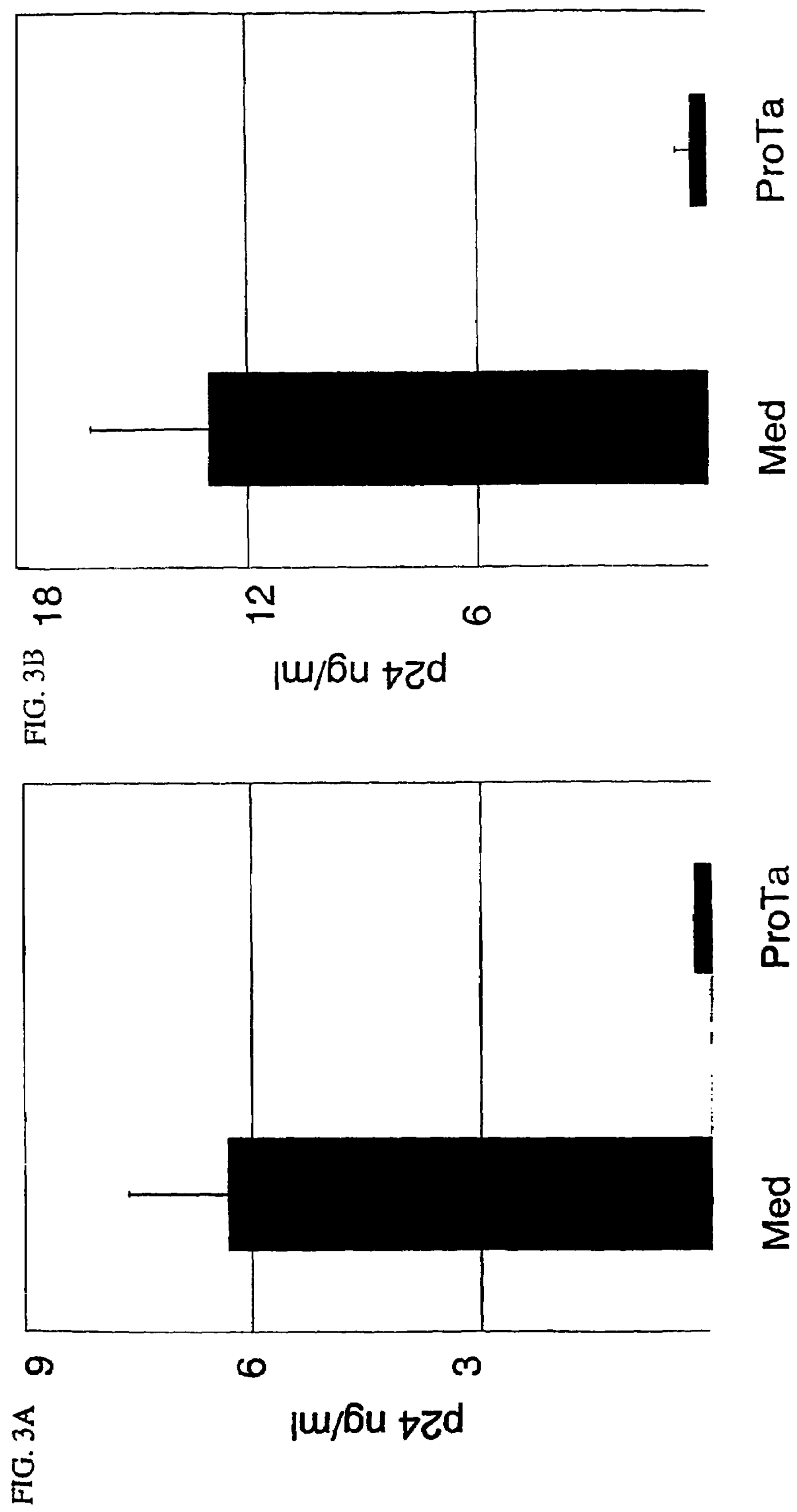

Effects of ProTα chromatography fraction on HIV-1 replication. In each panel, the indicated virus at a multiplicity of infection of 0.1 was incubated with cells for the time period shown. Unbound virus was washed out and the cells were incubated with 2 ng/mL of protein from the ProTα containing fraction. The results (mean±standard deviations) of viral Gag p24 protein determinations from triplicate determinations in a single experiment at days 7-10 post infection.

(A) Primary macrophages were infected with HIV-$1_{BaL}$ for 2 hr.

(B) PHA activated primary $CD4^+$ T-cells were infected with HIV-$1_{BaL}$ for 1 hr.

(C) PHA activated primary $CD4^+$ T cells were infected with HIV-$1_{IIIB}$ for 1 hr.

These data are representative of three individual experiments.

FIG. 2

Dose dependent inhibition, by recombinant ProTα, of HIV-$1_{BaL}$ replication and inhibition of expression of an HIV-$1_{JRFL}$-LTR-luciferase reporter gene in primary macrophages.

(A) Primary macrophages were infected with HIV-$1_{BaL}$ at a multiplicity of infection of 0.1 or 0.01 for 2 hr and treated with 200 ng/ml recombinant ProTα after residual virus was washed out (similar results were obtained in 3 independent experiments).

(B) Primary macrophages were infected with $HIV_{JRFL}$ for 2 hr, and treated with 200 ng/ml of recombinant ProTα after residual virus was washed out and luciferase activity was measured 48-72 hr post infection.

(C) HeLa $CD4^+$ cells were infected with HIV-$1_{JRFL}$ and treated with 200 ng/ml of recombinant ProTα after residual virus was washed out and luciferase activity was measured 48-72 hr post infection. Similar results were obtained in 3 independent experiments

FIG. 3

Inhibition of replication of HIV-1 primary isolates in primary macrophages by recombinant ProTα. Primary macrophages infected with dual-tropic (A) or CCR5 tropic (B) HIV-1 primary isolates for 2 hr and treated with 200 ng/ml of recombinant ProTα after residual virus was washed out. HIV-1 p24 antigen was measured on day 15 post infection.

FIG. 4

Effect of ProTα on HIV-1 replication in monocyte derived dendritic cells (DCs). Monocyte derived dendritic cells were infected with $HIV_{VSV}$ for 2 or 72 hr, residual virus was washed out, and ProTα (200 ng/ml) was added at each time point. Luciferase activity (in R.L.U) was measured 24 hr post treatment. The values of three independent experiments represent luciferase levels of cells treated with ProTα compared to the cells treated with medium alone which was defined as 100%.

FIG. 5

The effect on anti-HIV-1 activity, of depletion of ProTα from the chromatographic fraction from which it was identified (A) or from recombinant ProTα (B) using an anti-ProTα antibody affinity column. Primary macrophages were infected with HIV-$1_{BaL}$ at a multiplicity of infection of 0.1 for 2 hr and treated with a chromatographic fraction (A) or recombinant ProTα (B) depleted by affinity column (capture fraction) or non-binding fraction (flow) after residual virus had been washed out. HIV-1 p24 antigen was measured on day 7 (A) and luciferase activity was measured on 48-72 hr post infection (B)

FIG. 6

Effect of ProTα or Tα1 on HIV-1 gene expression in primary macrophages. Primary macrophages were infected with $HIV_{JRFL}$ for 2 hr. Residual virus was washed out and ProTα or Tα1 were added. Luciferase activity (in RLU) was measured 72 hr post infection. Similar results were obtained in 3 independent experiments

FIG. 7

Effect of ProTα on HIV-1 gene transcription. Primary macrophages were infected with $HIV_{VSV}$ for 2, 24 and 48 hr. Residual virus was washed out and ProTα (200 ng/ml), AZT (100 μM) (A) or integrase inhibitor L731 988 (2-5 μM) (B) were added at each time point. Luciferase activity (in RLU) was measured 72 hr post infection (C) RNA was isolated from primary macrophages 48-72 hr post infection with $HIV_{VSV}$ and treated for 24 hr with medium alone or ProTα. Real time RT-PCR was performed. The values of three independent experiments represent luciferase reporter gene RNA level of cells treated with ProTα compared to the cells treated with medium alone which was defined as 100%.

FIG. 8

Activation of STAT1 in primary macrophages and HeLa-CD4 cells was induced by $CD8^+$ cell conditioned medium but not by ProTα treatment. Primary macrophages and HeLa-CD4 cells were treated either with 10% $CD8^+$ cell conditioned medium or 1 ug/ml ProTα for 15 min then total cell lysate was prepared in a sample loading buffer. Western blotting analysis was done using anti-phospho-STAT1 antibody and then the blot was stripped and re-probed with anti-STAT1 antibody.

FIG. 9

Effect of ProTα on luciferase reporter gene expression controlled by different promoters. HIV-1 LTR (A), CMV (VVCW/LBE) (B) or PGK (VVPW/LBE) promoters (C). Macrophages were infected with $HIV\text{-}1_{VSV}$ carrying a luciferase reporter gene under the LTR, CMV or PGK promoter for 48 hr. After the virus was washed out, 200 ng/ml ProTα or medium was added to the cells. Luciferase assay was performed 24 hr post treatment. Similar results were obtained in 3 independent experiments

FIG. 10

Effect of ProTα on replication of wild type (LTR) HIV-Ba-L and mutated (LTR) C2,C3Ba-L in primary macrophages. Primary macrophages were infected with HIV-Ba-L or C2,C3Ba-L for 2 hr after the residual virus was washed out 200 ng/ml ProTα Integrase Inhibitors or medium was added to the cells. ELISA for the presence of p24 antigen was performed on days 6-10 post infection. The values of three independent experiments represent p24 antigen level of cells infected with HIV-1 with wild type LTR or mutated LTR and treated with ProTα compared to the cells treated with medium alone which was defined as 100%.

FIGS. 11A and B

Nucleic and amino acid sequences of human prothymosin alpha (GenBank Acc. Nos. BX647606 and P06454, respectively): SEQ ID NOs: 1 and 2, respectively.

FIG. 12

Nucleic acid sequence of human prothymosin alpha pseudogene 8 (GenBank Acc. No. NG_004798): SEQ ID NO: 3.

FIGS. 13A and B

Nucleic and amino acid sequences of human prothymosin alpha pseudogene 28 (GenBank Acc. Nos. NM_002823 and NP_002814): SEQ ID NOs: 4 and 5, respectively.

FIG. 14

Amino acid sequence of orangutan prothymosin alpha (GenBank Acc. No. Q5R790): SEQ ID NO: 6.

FIG. 15

Amino acid sequence of house mouse prothymosin alpha (GenBank Acc. No. P26350): SEQ ID NO: 7.

FIG. 16

Amino acid sequence of Norway rat prothymosin alpha (GenBank Acc. No. P06302): SEQ ID NO: 8.

FIG. 17

Amino acid sequence of cow prothymosin alpha (GenBank Acc. No. P01252): SEQ ID NO: 9.

FIG. 18

Amino acid sequence of zebrafish prothymosin alpha (GenBank Acc. No. Q6NV32): SEQ ID NO: 10.

FIG. 19

Amino acid sequence of edible frog prothymosin alpha (GenBank Acc. No. Q90ZK2): SEQ ID NO: 11.

DETAILED DESCRIPTION OF THE INVENTION

The present invention is directed to ProTα, which has been identified as a novel inhibitor of HIV infection in macrophages and dendritic cells. In that macrophages are known to shed HIV-1 for months after infection, this cell type is of particular significance with respect to disease progression in HIV-1 infected individuals. Targeting such cellular reservoirs of the virus may, therefore, effectively prevent or at least attenuate the systemic spread of the disease. Accordingly, the invention is directed to methods of using ProTα molecules (ProTα protein and functional derivatives and fragments thereof and ProTαhomologs/orthologs and/or nucleic acid sequences encoding ProTα protein and functional derivatives and fragments thereof and ProTα homologs/orthologs) for preventing HIV-1 infection and/or treating subjects infected with HIV-1. The invention is further directed to compositions comprising ProTα molecules and to methods for using such compositions in the prevention and/or treatment of HIV infection.

Moreover, the methods of the present invention may also be used to advantage to prevent and/or treat a variety of infectious diseases, particularly those associated with viral infection. In view of the results presented herein below, the methods of the invention may be used to particular advantage when the infectious disease to be prevented and/or treated involves infection of macrophages and/or dendritic cells. This prediction is well supported by the finding that ProTα exhibits particularly pronounced anti-viral properties with respect to HIV-1 in the context of infected macrophages and/or dendritic cells.

An inhibitor of the invention is defined as a ProTα peptide or polypeptide which is capable of reducing, eliminating or preventing infection by HIV or other virus (e.g., other retroviruses, lentiviruses, or a hepatitis virus). Specifically, the invention is directed to the novel discovery that ProTα acts an inhibitor of HIV infection. Accordingly, the invention pertains to methods directed to using ProT polypeptides and nucleic acids encoding ProTα polypeptides, and to nucleic acids which hybridize to a ProTα coding sequence at high stringency and encode a ProTα polypeptide of the invention for prevention of and/or therapy for infectious diseases. The invention further encompasses methods that utilize analogs, homologs, orthologs, derivatives and truncated fragments of ProTα which retain these defined functional properties.

As used herein, the term "peptide" refers to an oligomer of at least two contiguous amino acids, linked together by a peptide bond, and not greater than fifty amino acids. As used herein, the term "polypeptide" refers to an oligomer of at least fifty amino acids.

As used herein, "substantially corresponds" means an amino acid sequence having approximately 80% homology in amino acid sequence to an inhibitor of the invention. For example, conservative amino acid substitutions which do not alter the chemical type of amino acid residue in an inhibitor can be introduced into the inhibitor provided that its functional activity is retained. By "homolog" is meant the corresponding peptides or polypeptides which are derived from an inhibitor of the invention so long as the functional properties of the inhibitor are retained.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence. With respect to the present invention, "consisting essentially of" encompasses highly acidic polypeptides, which exhibit anti-viral properties similar to those of ProTα and comprise amino acid sequences that are 85% or greater homologous to ProTα (e.g., human ProTα) as determined using alignment programs known in the art.

The term "functional" as used herein implies that the nucleic or amino acid sequence is functional for the recited assay or purpose.

The term "functional fragment" as used herein implies that the nucleic or amino acid sequence is a portion or subdomain of a full length polypeptide and is functional for the recited assay or purpose.

By "analog" is meant substitutions, rearrangements, deletions, truncations and additions to the amino acid sequence of an inhibitor, so long as its functional properties are retained. Analogs also include inhibitors which contain additional amino acids added to either end of the peptides that do not affect biological activity, e.g., the presence of inert sequences added to a functional inhibitor which are added to prevent degradation. An algorithm can be used in the identification of homologs and analogs, such as the BLASTP program (Altschul, J. Mol. Evol. 36:290, 1993; Altschul, J. Mol. Biol. 215:403, 1990), which may be used in the methods of the present invention.

The criticality of particular amino acid residues in an inhibitor such as ProTα may be tested by altering or replacing the residue of interest. For example, the requirement for a cysteine residue, which can be involved in the formation of intramolecular or intermolecular disulfide bonds, can be tested by mutagenesis of the cysteine to another amino acid, for example, tyrosine, which cannot form such a bond.

In a particular embodiment, an inhibitor of the invention comprises a polypeptide having an amino acid sequence substantially corresponding to the amino acid sequence of ProTα. See FIGS. 11-29, wherein are shown the amino and/or nucleic acid sequences of prothymosin alpha derived from a number of different species including: human [GenBank Acc. Nos. BX647606 and P06454; pseudogene 8, GenBank Acc. No. NG_004798; and gene sequence 28, GenBank Acc. No. NM_002823 and NP_002814], orangutan (GenBank Acc. No. Q5R790), mouse (GenBank Acc. No. P26350), rat (GenBank Acc. No. P06302), cow (GenBank Acc. No. P01252), zebrafish (GenBank Acc. No. Q6NV32), and edible frog (GenBank Acc. No. Q90ZK2). See also a review article by Pineiro et al. (Peptides (2000) 21:1433-1446), wherein details pertaining literature references that disclose sequences of additional ProTα homologs/orthologs is found.

The term "ortholog" as used herein refers to polypeptides encoded by nucleic acid sequences of a different species whose polypeptide product has greater than 60% identity to, for example, a human ProT encoding sequence and/or whose gene products have similar three dimensional structure and/or biochemical activities of human ProTα. The use of such orthologs in the methods of the invention is contemplated herein.

The term "homolog" as used herein refers to polypeptides encoded by nucleic acid sequences of the same species whose polypeptide product has greater than 60% identity to, for example, a human ProTα encoding sequence and/or whose gene products have similar three dimensional structure and biochemical activities of human ProTα. The use of such homologs in the methods of the invention is contemplated herein.

Chimeric inhibitors which combine one or more of the preferred peptides or polypeptides or segments or fragments thereof are within the scope of the invention. Inhibitors of the present invention also include cyclic or derivatized peptides, and further include peptides containing D-amino acids as well as L-amino acids.

The peptide and polypeptide inhibitors of the invention can be synthesized according to Merrifield solid-phase synthesis techniques (Kotler et al., Proc. Natl. Acad. Sci. 85:4185-4189, 1985; Barany et al., in Gross et al., eds., The Peptides, Vol. 2, Academic Press, 1980) or other techniques of peptide synthesis known to those skilled in the art. After cleavage and deprotection, synthetic peptides or polypeptides can be purified by, for example, gel filtration, chromatography, and any reverse-phase column/HPLC system known to those skilled in the art. Peptide inhibitors derived from an inhibitor of the invention may also be produced by chemical or enzymatic digestion of the full-length protein using techniques that are known to those skilled in the art.

Peptides and polypeptides may also be prepared by standard recombinant DNA technology using techniques well known to those skilled in the art for nucleotide-based based peptide design (Sambrook et al., Molecular Cloning: A Laboratory Manual, 2nd edition, Cold Spring Harbor Press, Cold Spring Harbor, N.Y., 1989; Ausubel et al., Current Protocols in Molecular Biology, John Wiley and Sons, New York, 1995). Site-directed mutagenesis using recombinant DNA techniques, for example, may be used to prepare peptide analogs and homologs from parent peptides.

An inhibitor such as, e.g., ProTα, may be recovered by purification from a cell line secreting such an inhibitor, using standard techniques for protein purification which are known to those skilled in the art, including, but not limited to, size fractionation, ion-exchange chromatography, and reverse-phase chromatography.

ProTα protein may be prepared in a variety of ways, according to known methods. As indicated herein above, naturally occurring ProTα protein may be purified from appropriate sources. This is not, however, a preferred method due to the low amount of protein likely to be present in a given cell type at any time. The availability of nucleic acid molecules encoding ProTα enables production of this protein using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Biotech, Madison, Wis. or BRL, Rockville, Md.

Alternatively, according to a preferred embodiment, larger quantities of ProTα may be produced by expression in a suitable prokaryotic or eukaryotic system. For example, part or all of a DNA molecule, such as a cDNA of SEQ ID NO: 1, may be inserted into a plasmid vector adapted for expression in a bacterial cell, such as *E. coli*. Such vectors comprise regulatory elements necessary for expression of the DNA in a host cell (e.g. *E. coli*) positioned in such a manner as to permit expression of the DNA in the host cell. Such regulatory elements required for expression include promoter sequences, transcription initiation sequences and, optionally, enhancer sequences.

As used herein, the term "operably linked" refers to a regulatory sequence capable of mediating the expression of a coding sequence and which are placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

ProTα produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

"Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The amino acid sequences of the peptides and polypeptides can be confirmed and identified by amino acid composition analysis as well as manual and automated Edman degradation and determination of each amino acid, HPLC analysis, or mass spectrometry.

The inhibitors of the invention are characterized by an ability to decrease or prevent viral replication in an active HIV infection in vivo or in a cellular model system. An inhibitor may also be characterized by its effects in altering, reducing or eliminating viral morphogenesis, replication, or virion infectivity. Where an inhibitor is incubated with HIV-infected cells, the production of infectious virus progeny is determined relative to control experiments without inhibitor.

Inhibitors can be characterized in tissue culture models of viral infection using cells infected with any lentiviral or retroviral infection, including, but not limited to, those resulting from HIV-1, HIV-2, simian immunodeficiency virus (SIV), feline immunodeficiency virus (FIV), bovine immunodeficiency virus (BIV), visna virus and all strains and isolates thereof. Specific HIV strains which have tropism for certain cell types can be used, including the macrophage-tropic HIV Ba-1, and the T-tropic HIV IIIB and MN. In general, isolates can include lymphotropic and macrophage-tropic strains, primary strains derived from blood cells or tissues, and North American, European, African and Asian isolates.

Primary cells or cell lines which can be used for inhibitor studies on virus-infected cells are preferably those that are susceptible to such viral infection. Such cells include, for example, peripheral blood lymphocytes (PBL), especially CD4+ cells, and macrophages and dendritic cells.

Assay systems which employ a vector-delivered full or partial HIV genome into a eucaryotic cell can be used to simulate the production of viral proteins and virion production, and such cells can be used in the characterization of an HIV inhibitor.

To assess whether an inhibitor reduces or eliminates the generation of infectious viral progeny, the quantity and type of infectious progeny are assayed at suitable times post-infection. Evidence of microscopically observed viral spread, cytopathic effect, and increased amounts of the p24 capsid protein can provide an assessment as to whether infectious progeny are being generated. The assessment of progeny virus infectivity may be determined further by recovery of infected cells and co-cultivation with suitable cells (e.g., PBL, macrophages, or dendritic cells) or by the recovery of supernatant from the infected cells and cell-free infection of suitable cells. Another method of phenotypic determination involves the observation of progeny virus for morphological analysis, e.g., by electron microscopy.

Quantitative assessment of an HIV infection conducted in the presence of an inhibitor can also be determined using molecular markers, for example, by assaying viral p24 production by ELISA assay, reverse transcriptase activity, or viral DNA synthesis by quantitative PCR using standard techniques known to those skilled in the art.

A DNA encoding an inhibitor can be used to engineer cell lines which constitutively express the inhibitor in order to test the effect of an inhibitor on different isolates of HIV-1 or other HIV strains. Such isolates include lymphotropic and macrophage-tropic strains, primary strains derived from blood cells or tissues, and North American, European, African and Asian isolates. Such methods can allow the selection of an inhibitor which has optimal inhibitory effect on a particular viral isolate of interest. One of skill in the art will also appreciate that such cell lines can also be used to test the effect of an inhibitor on different viruses (e.g., other retroviruses, lentiviruses, and hepatitis virus) and isolates and strains thereof.

The inhibitors of the invention can be tested in animal models of HIV infection, including the SCID-Hu mouse model of HIV-1 infection (Aldrovandi et al., J. Virol. 70:1505, 1996) and SIV-infected monkeys. Such models of infection are suitable for testing the inhibitors of the invention for efficacy against challenge with HIV or other lentiviruses and other retroviruses in order to identify those inhibitors which can be used for prevention or treatment of viral infection. Animal models designed for other viruses may also be utilized in a similar manner by those of skill in the art.

The inhibitors of the invention can be assayed to determine the concentration required to achieve an antiviral effect against a target virus. A convenient variable for measurement is the concentration of an inhibitor required to inhibit 50% of viral replication ($IC_{50}$), whether assayed in cell culture or with the use of a molecular marker such as the measurement of viral p24 production by ELISA assay, presence of viral RNA, reverse transcriptase activity, or viral DNA synthesis by quantitative PCR using standard techniques known to those skilled in the art.

Inhibitors of the invention can be evaluated for cytotoxic effects using standard assays that measure cell viability. Such assays include $^{14}C$ protein hydrolysate, $^{3}H$ thymidine uptake, MTT reduction, and cell growth. Such parameters as $TD_{50}$ (toxic dose to 50% of the tested culture) can be derived from such assays. Comparison of the $TD_{50}$ so derived with the $IC_{50}$ (inhibitor concentration required to inhibit 50% of the viral marker being tested or viral replication) can indicate a therapeutic index for a particular compound (TI). Preferably, the $IC_{50}$ is at least ten times higher than the $TD_{50}$, and the $IC_{50}$ is effective at a minimum of $10^{-6}$ M in culture to be considered as a prospective inhibitor of the invention. Most preferably, an inhibitor of the invention exhibits an $IC_{50}$ of $10^{-7}$ M or $10^{-8}$ M.

The inhibitors of the invention are useful in the isolation of HIV or other lentiviral and retroviral mutants which are resistant to the inhibitor but which can be used in subsequent screens to identify other antiviral agents to which they are susceptible, thereby generate a profile of inhibition for a particular viral isolate.

In a particular embodiment of the invention, an inhibitor of a viral infection (e.g., an HIV infection) comprises a peptide or polypeptide having an amino acid sequence which substantially corresponds to SEQ. ID NOs: 2, 5, or 6-11. An inhibitor of a viral infection (e.g., an HIV infection) may also be a peptide or polypeptide having an amino acid sequence comprising any one of SEQ. ID NOs: 2, 5, or 6-11. Such sequences also include orthologs, homologs, derivatives, and functional fragments of any one of SEQ. ID NOs: 2, 5, or 6-11.

In view of the above noted properties of the inhibitors of the invention, it is further contemplated that the inhibitors of the invention may be used in compositions for the prevention or treatment of an HIV or other lentiviral and retroviral infection, and the treatment of consequent pathologic conditions such as AIDS. Another aspect of the invention, therefore, is directed to methods for preventing and treating an HIV or other lentiviral or retroviral infection by administering a composition containing one or more of the inhibitors of the invention to an individual infected with or exposed to HIV for a time and under conditions to accomplish such result.

The inhibitors, compositions and methods of the invention can be used in the treatment of HIV-positive individuals, including those exhibiting the conditions of AIDS-related complex (ARC) and AIDS, as well as those who are asymtomatic. These inhibitors, compositions and methods can also be used in the prophylaxis of HIV or other lentiviral and retroviral infections, and can also be used the treatment or prophylaxis of veterinary infections caused by lentiviruses and other retroviruses.

The inhibitors of the invention may be used alone or in combination with other known or to be discovered inhibitors of HIV replication, including, but not limited to, other antiviral compounds, immunomodulators, antibiotics, vaccines, chemokines and other therapeutic agents. Particular agents which can be used in combination with the inhibitors of the invention include, but are not limited to, azidothymidine (AZT), dideoxyinosine (DDI), dideoxycytosine (DDC), saquinavir, indinavir, ritonavir, and other antiviral compounds. The inhibitors of the invention may also be used in combination with agents which are used to treat secondary complications of HIV infection, e.g., gancyclovir used in the treatment of cytomegalovirus retinitis. Combination therapy may retard the development of drug-resistant mutants by requiring multiple mutation events for the emergence of a fully drug-resistant isolate.

The inhibitors of the present invention may be administered to a host as a composition in an amount effective to inhibit HIV infection and/or transcription/replication in target cells. The compositions contain an effective dosage of at least one of the inhibitors of the present invention, together with an acceptable carrier.

In that ProTα is a remarkably stable protein, it is well suited for pharmaceutical applications. The stable nature of this protein is due, at least in part, to N-terminal acetylation [Haritos et al. Proc Natl Acad Sci USA 81 (1984): 1008-1011], and to a remarkable cluster of so-called stabilizing amino acids at the N-terminus. Indeed, ten out of the first twelve N-terminal positions of ProTα are occupied by amino acid residues belonging to this stabilizing class [Bachmair et al. Science 234 (1986):179-186]. These features impart protection against proteolytic degradation.

The inhibitors of the invention may be systematically administered for preventing and/or treating an HIV or other lentiviral or retroviral infection. When used systemically, the inhibitor compositions may be formulated as liquids, pills, tablets, lozenges or the like, for enteral administration, or in liquid form for parenteral injection. The peptides and/or polypeptides (or inhibitor-protein conjugates) may be combined with other ingredients such as carriers and/or adjuvants. There are no limitations on the nature of such other ingredients, except that they must be physiologically acceptable, efficacious for their intended administration and cannot degrade the activity of the active ingredients of the compositions. An inhibitor can also be covalently attached to a protein carrier, such as albumin, so as to minimize diffusion of the inhibitor.

As used herein, a physiologically acceptable carrier includes any and all solvents, dispersion media, coatings, antibacterial and antifungal agents, isotonic agents and the like. The use of such media and agents are well-known in the art.

The forms of the compositions suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyol such as glycerol, propylene glycol, polyethylene glycol, suitable mixtures thereof, surfactants or vegetable oils. Sterilization can be accomplished by an art-recognized technique, including but not limited to, filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject inhibitors is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

The polypeptide compositions also may be impregnated into transdermal patches, plasters and bandages, preferably in a liquid or semi-liquid form.

When the inhibitors of the invention are administered orally, the compositions thereof containing an effective dosage of the peptide may also contain an inert diluent, an assimilable edible carrier and the like, be in hard or soft shell gelatin capsules, be compressed into tablets, or may be in an elixir, suspension, syrup or the like.

As indicated above, the inhibitors may be administered by any convenient route, for example by infusion or bolus injection, by absorption through epithelial or mucocutaneous linings (e.g., oral mucosa, rectal, vaginal, and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a particular embodiment, it may be desirable to administer the pharmaceutical compositions of the invention locally, e.g., by local infusion during surgery, topical application, e.g., by injection, by means of a catheter, or by means of an implant, said implant being of a porous, non-porous, or gelatinous material, including membranes, such as sialastic membranes, or fibers.

The subject inhibitors are thus compounded for convenient and effective administration in physiologically effective amounts with a suitable pharmaceutically acceptable carrier in a therapeutically effective dosage. Examples of suitable pharmaceutical carriers are described in "Remington's Pharmaceutical Sciences" by E. W. Martin, incorporated in its entirety by reference herein.

The precise effective amount of inhibitor to be used in the methods of this invention to prevent or treat an HIV infection cannot be stated because of the nature of the infectious process. It must be noted that the amount of inhibitor to be administered will vary with the degree of infection in an individual, as determined by such parameters as viral load and CD4 cell counts. Individual-specific variables such as age, weight, general health, gender, diet, and intake of other pharmaceuticals can factor into the choice of dosage. The design of an optimal protocol for an infected individual may further consider the identity of the viral isolate(s) isolated from an infected individual with an infection for optimal result. A further consideration in protocol design would be the presence of a viral strain which is already resistant to existing protease or reverse transcriptatse inhibitors.

The amount of an inhibitor of the invention per unit volume of composition for administration depends upon the amount of active ingredients that are afforded directly to the site of infection. However, it can generally be stated that a peptide or polypeptide inhibitor of the invention should preferably be present in an amount of at least about 1.0 nanogram per milliliter of combined composition, more preferably in an amount up to about 1.0 milligram per milliliter.

Systemic dosages depend on the age, weight and condition of the individual and on the administration route. In general, for example, a suitable dosage for the administration to adult humans ranges from about 0.01 to about 100 mg per kilogram body weight. The preferred dosage ranges from about 0.5 to about 5.0 mg per kilogram body weight.

The amount of the compound of the invention which will be effective in the prevention and/or treatment of an infectious disease (e.g., viral infection) can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Suppositories generally contain active ingredient in the range of 0.5% to 10% by weight; oral formulations preferably contain 10% to 95% active ingredient. Effective doses may be extrapolated from dose-response curves derived from in vitro or animal model test systems.

Since the inhibitory compositions of this invention are effective in reducing or eliminating the ability of HIV or other lentiviruses and other retroviruses to generate infectious progeny, periodic readministration of the compositions may be indicated and preferred.

The peptide and polypeptide inhibitors of the invention can also be delivered to an individual by administering a vector that comprises and expresses a nucleic acid encoding the inhibitor. DNAs encoding one or more of the inhibitors of the invention can be delivered to the cells of an individual in need of such an inhibitor by any method of gene transfer known to those skilled in the art, including, but not limited to, viral vectors, lipid-mediated delivery, transfection, electroporation, as well as other methods. Viral vectors which can be used to deliver such inhibitors include those derived from DNA and RNA viruses, including, but not limited to, adenovirus, herpesvirus, poxvirus, retrovirus, and adeno-associated virus.

Parameters, which are used to monitor the effect of an inhibitor of the invention administered to an individual with an established HIV infection or administered to an individual for prophylaxis, include the use of CD4 counts, plasma viral RNA concentration, viral phenotype, p24 antigen concentration, viral phenotype, level of anti-HIV antibodies as well as other markers of the clinical progression of an HIV infection known to those skilled in the art.

It will be recognized that the inhibitors and methods of the invention can be used in the treatment or prevention of any other lentiviral or retroviral infection, including, but not limited to, those resulting from HIV-1, HIV-2, simian immunodeficiency virus (SIV), feline immunodeficiency virus (FIV), bovine immunodeficiency virus (BIV), visna virus and all strains and isolates thereof.

The practice of the invention employs, unless otherwise indicated, conventional techniques of protein chemistry, molecular virology, microbiology, recombinant DNA technology, and pharmacology, which are within the skill of the art. Such techniques are explained fully in the literature. See, e.g, Current Protocols in Molecular Biology, Ausubel et al., eds., John Wiley & Sons, Inc., New York, 1995; Remington's Pharmaceutical Sciences, 17th ed., Mack Publishing Co., Easton, Pa., 1985; and Molecular Cloning: A Laboratory Manual, Sambrook et al., eds., 2nd edition, Cold Spring Harbor Press, Cold Spring Harbor, N.Y., 1989.

EXAMPLES

Introduction

In this study, the present inventors identify Prothymosin a (ProTα) as a factor derived from an HVS transformed CD8+ cell line that possesses significant HIV-1 inhibitory activity in primary macrophages and dendritic cells (DCs). It appears to act following viral entry reverse transcription and integration. ProTα is a small (12 KD) highly acidic protein (20-22) without a secretion signal (23), which is known primarily for its association with cell proliferation (22, 24-26). Although no secretory pathway has been described for this protein, it has been detected in human serum and supernatants of lymphocytes (27, 28). The present inventors show herein, using native and recombinant ProTα, that ProTα is a potent inhibitor of HIV-1 LTR driven gene transcription in infected macrophages and DCs.

Evidence presented herein, which attests to the potent anti-HIV-1 activity exhibited by ProTα, also supports the contention that ProTα acts as a potent anti-viral agent in general. Other viral infections for which the methods of the present invention may be used to advantage include, without limitation, those caused by other retroviruses, lentiviruses, and hepatitis viruses. Moreover, a skilled practitioner would be able to predict and evaluate the efficacy of the methods of the present invention for the treatment of a variety of infectious diseases, particularly those caused by viruses

Methods and Materials

Reagents

Recombinant human ProTα and antibody to ProTα were purchased from Alexis Biochemicals (San Diego, Calif.). Antibodies against STAT1 and P-STAT1 were purchased from Santa Cruz Biotechnology (Santa Cruz, Calif.) Integrase inhibitors L-731 988 from Merck.

Cells.

HeLa-CD4 cells were obtained from National Institute of Health AIDS Research and Reference Reagents Program. Primary macrophages were isolated by adhesion from Ficoll-Hypaque (Sigma) purified PBMCs after 10-14 days in culture with DMEM containing 20% FBS. Primary CD4+ cells were purified by positive or negative selection using magnetic beads from Miltenyi Biotech (Auburn, Calif.) and cultured in RPMI containing 10% FBS and 50 U IL-2.

Human monocyte derived dendritic cells (MDDC) were prepared from the CD14+ monocytes. Briefly, PBMCs were isolated from buffy coat using Ficoll-hypague density gradient centrifugation followed by positive selection of CD14+ cells. Magnetic cell separation system from Milteneyi Biotec was used for monocyte isolation according to manufacturer's recommendation. The purity of the isolated CD14+ cells was >95%. Immature MDDC were cultured in the presence of IL-4 (500 U/ml, R&D Systems) and GM-CSF (700 U/ml, R&D systems) for 6-7 cells and then used for HIV-1 infection assays.

Viruses

HIV-Ba-L and HIV-IIIB were purchased from ABI (Columbia, Md.). HIV-1 primary isolates were obtained from the National Institute of Health AIDS Research and Reference Reagents Program 92BR028 and 92BR030-R5 and 92RW009-R5/X4 isolate.

Mutated mC2,C3-Ba-L clone that has point mutations in two high affinity C/EBP binding sites of CCMT-box of LTR were kindly provided by Dr. A Henderson (35). Infectious virus stock was produced by Lipofectamine 2000 transfection of 293T cells with mC2,C3-Ba-L clone as previously described. Virus production was standardized by p24 antigen production measured by Elisa.

HIV-1 and VSV Env-Pseudotyped Virus Production and Infection Assay.

HIV-JRFL or Vesicular stomatitis virus (VSV) Envelope pseudotyped HIV-1, with luciferase reporter gene were generated as described previously (61). Briefly, 293T cells were cotransfected using lipofectAMINE 2000 (Life Technologies, Gaithersburg, Md.) with envelope-deficient pNL4-3-LucR$^-$E$^-$ (NIH AIDS Research and Reference Reagent Program) for expression of luciferase reporter gene, PCMVΔR 8.2 for expression of viral protein vpr, pSV plasmid for expressing VSV-G envelope glycoprotein or pJRFL (a gift from D. Littman New York University Medical Center, NY) for HIV-1 envelope. The supernatant containing the virus was collected 48 hr after transfection, filtered, analyzed for HIV-1 p24 antigen and stored at −80 C.

Macrophages were seeded at concentration 0.2-0.3×10$^5$ per well in 96 well plate and infected with JRFL or VSV envelope pseudotyped HIV-1. At 3-7 days post infection the luciferase assay was performed using (Promega, Madison, Wis.) 50 ul of lysis buffer. Luciferase activity was measured (in relative light units RLU) with Berthold MiniLumat luminometer.

Western Immunoblotting Analyses.

Whole cell extract from macrophages and Hela cells treated with 10% cell conditioned medium from CD8+ cells, ProTα or medium was prepared by adding 1×SDS Sample buffer (100 ul per 6 well plate). For western blot analyses, protein samples were treated with 2.5 M DTT or 2.5% 2-mercaptoethanol and separated by SDS-Page 4-20% Tris-Glycine gradient gels (Novex-Invitrogen Calif.). Following separation by SDS-Page, the gel was blotted onto PVDF membrane (Novex-Invitrogen San-Diego, Carlsbad, Calif.). After blocking with 5% nonfat milk the membrane was incubated with 1/1000 dilution of anti P-STAT-1 (Tyr701) (Cell Signaling Technology) for 24 hr at 4° C. in PBS. The membrane was washed in PBS with 0.05% Tween 20 and treated with 1/2000 diluted anti-rabbit antibodies labeled with horseradish peroxide (Amersham pharmacia UK). The membrane was washed in PBS with 0.05% tween 20 and Western blot chemiluminescence reagent was added.

Inhibition of HIV-1 Replication by ProTα

To screen for inhibitors that worked after viral entry, the purified macrophages were first incubated with the R5 isolate of HIV-1 BaL for 2 h at a multiplicity of infection (MOI) of either 0.1 or 0.01, then washed and subsequently cultured in the presence of $CD8^+$ cell conditioned medium (10% by volume) or different fractions derived from serum free conditioned medium. The medium was changed every 3-4 days and fresh medium with 10% conditioned medium or fractions thereof were added. HIV-1 replication was monitored by measuring HIV-1 p24 antigen using an enzyme-linked immunosorbent assay (ELISA) (SAIC-Frederick, Inc NCI MD). Both 10-15 day old primary macrophages and primary CD4+ cells separated by magnetic beads using a Miltenyi Biotech CD4+ T cell isolation kit were plated in 96 well plates. Macrophages were plated at a concentration of $0.2\text{-}0.3\times10^5$ cells per well and PHA activated CD4+ lymphocytes were plated at $1.5\text{-}2\times10^5$ cells per well. To determine the antiviral activity of ProTα Laboratory-adapted strains HIV-1 Bal and IIIB at an MOI of 0.01 or 0.1 were used to infect cells and washed off at two hours followed by the addition of ProTα at the concentrations indicated. One-half of the medium was replaced every 3-4 days and new ProTα was added. HIV p24 antigen production was measured by ELISA as using SAIK Frederick kit (NCI MD).

Real Time RT-PCR

RNA was isolated from macrophages infected with $HIV_{VSV}$ for 72 hr and treated with medium alone or ProTα 24 hr post treatment using Absolutely RNA kit (Stratagene). Real time PCR was done at Mount Sinai Medical Center Core Facility using following primers:

for Luciferase reporter gene: sense-AACACCCCAACATCTTCGAC antisense-CGGTACTTCGTCCACAAACA.

for IkB sense-GCCAGCGTCTGACGTTATGA anisense-GAGGGCTGATCCTACCACAA.

Each assay was performed in triplicate. Quantification of each PCR product was expressed relative to -actin.

Results

Prothymosin Alpha (ProTα) is Identified as the HIV-1 Inhibitory Molecule Present in a Chromatographic Fraction with Potent HIV-1 Inhibitory Activity. A 1.3 L volume of cell-free, serum-free, phenol red-free RPMI 1640 medium conditioned for 48 hours by cells of the HVS/$CD8^+$ T-cell line K#150 K (4) was accumulated. All the HIV suppressing activity from this medium was captured and separated, as completely as possible, by a multi-step chromatographic separation strategy developed for this purpose. Fast concentration of all HIV-1 suppressing activity by ion exchange capture was achieved using an expanded bed format. The flow-through, unretained fraction had no HIV-1-suppressing activity based on the described assay for suppression. Active peaks were further fractionated on phenyl sepharose and samples of the fractions assayed. To further fractionate under biologically mild conditions, the present inventors used gel filtration to separate the components of active fractions of the phenyl sepharose fractionation. The location of the separated active species was determined by the ability of a 3 ng/mL aliquot of each fraction to inhibit HIV-$1_{BaL}$ replication in primary macrophages previously incubated with virus containing medium which was washed out after 2 hr. The cells were maintained in the presence of 3 ng/mL of HIV-1 inhibitory chromatographic fraction during the assay period. ELISA assays for the presence of HIV-1 p24 antigen as a measure of viral replication were performed seven days after infection. A protease digest mass spectral fingerprint of an aliquot of this fraction matched the database theoretical digest fingerprint of ProTα and a 15 residue de novo sequence (AVDTSSEITTKDLKE) of an N-terminal peptide derived from another aliquot of the same material was an exact match to residues 3 to 18 of ProTα. An aliquot of HIV-1 inhibitory fraction diluted to 2 ng/mL produced an approximately 95% reduction of viral p24 protein compared with untreated control cells (FIG. 1A). A similar aliquot from the same fraction had substantially less protective activity for PHA-stimulated $CD4^+$ cells infected with HIV-$1_{BaL}$ and HIV-$1_{IIIB}$ (FIGS. 1B and C).

ProTα from a Recombinant Source (rProTα) Suppresses HIV-1 in Macrophages and Dendritic Cells but not in CD4+ Cells. To confirm the identity of the database match, the present inventors undertook the same set of assays with rProTα. Results obtained with rProTα (FIG. 2A) reveal a dosage dependent suppression of HIV-$1_{BaL}$ replication in primary macrophages as measured by HIV-1 p24 antigen. Furthermore, as little as 2 ng/mL of the rProTα produced greater than 80% reduction of viral p24 antigen in this assay. To limit the assay to one round of the viral life cycle by eliminating the possibility of infection of cells by newly synthesized viral particles during the assay, the present inventors repeated the assays by infecting the primary macrophages with a replication-defective JRFL envelope pseudotyped HIV-1 (HIV-$1_{JRFL}$) containing a luciferase gene under the control of the HIV-1 LTR. As expected, dose dependent inhibition of the luciferase reporter gene of HIV-$1_{JRFL}$ by ProTα was observed (FIG. 2B). ProTα did not, however, exhibit anti-HIV-$1_{JRFL}$ activity in HeLa $CD4^+$/$CCR5^+$ cells (FIG. 2C) or Hos $CD4^+$/$CCR5^+$ cells (data not presented). ProTα displayed inconsistent anti-HIV-1 activity, varying from 30-40% suppression to no suppression of replication of either HIV-1 lab isolates (HIV-$1_{BaL}$ and HIV-$1_{IIIB}$) or HIV-1 primary isolates, in primary $CD4^+$ cells (data not presented). To determine whether the anti-HIV-1 activity of ProTα is of potential clinical relevance, the effect of recombinant ProTα in primary macrophages infected with HIV-1 primary isolates was tested. ProTα inhibited replication of CCR5 (FIG. 3A), as well as a dual tropic HIV-1 primary isolate (FIG. 3B) in primary macrophages. No cytotoxicity was observed in macrophages or CD4 T cells treated with up to 1 ug/ml of rProTα, as measured by standard CellTiter Non-Radioactive Cell Proliferation Assay (Promega) (data not presented).

Figure 4:
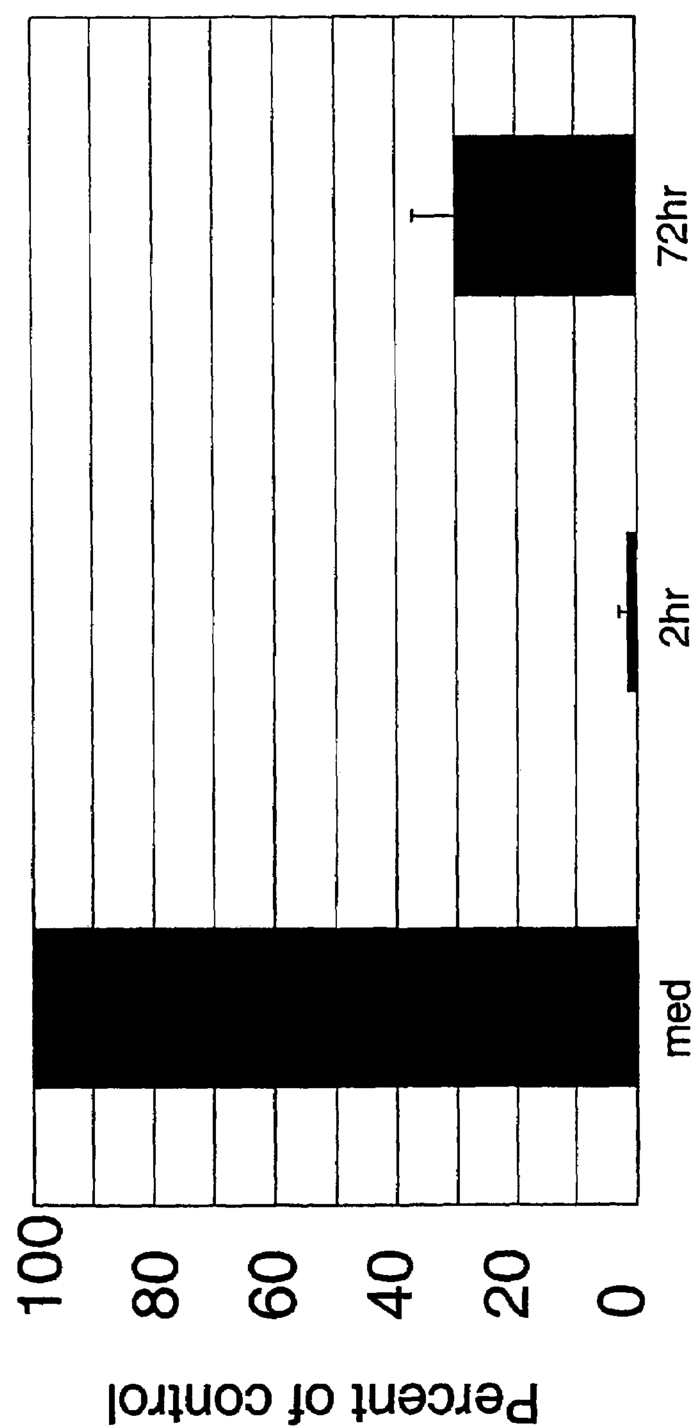

Since the anti-HIV effect of rProTα was observed in primary macrophages, the effect of rProTα on dendritic cells derived from the same myeloid progenitors was also examined. Expression of the reporter gene luciferase was reduced by 90% following treatment of DCs (2 hr post infection) with rProTα. rProTα was shown to inhibit integrated proviral HIV-1 by 65-75% (72 hr post infection) in dendritic cells (DCs) (FIG. 4).

In sum, these results demonstrate that ProTα is a potent inhibitor of HIV-1 replication in primary macrophages and dendritic cells.

Depletion of ProTα from the Chromatographic Fraction Leads to Partial Removal of Anti-HIV-1 Activity. The results presented above reveal that ProTα contributes to the anti-HIV-1 activity of the chromatographic fraction from which it was identified. To further investigate this hypothesis, a sample of the ProTα-containing chromatographic fraction was applied to an anti-ProTα-antibody affinity column. The captured eluate exhibited anti-HIV-1 activity similar to that of the parent fraction, while the non-binding flow through lost 50 to 80% of the activity (FIG. 5A). Moreover, the present inventors showed using the same affinity column that recombinant ProTα could be depleted from the preparation (FIG. 4B).

Thymosin Alpha 1 (Tα1), a Naturally Occurring Peptide Homologous to the First 28 Amino Acids of ProTα, has no Anti-HIV-1 Activity.

Figure 6:
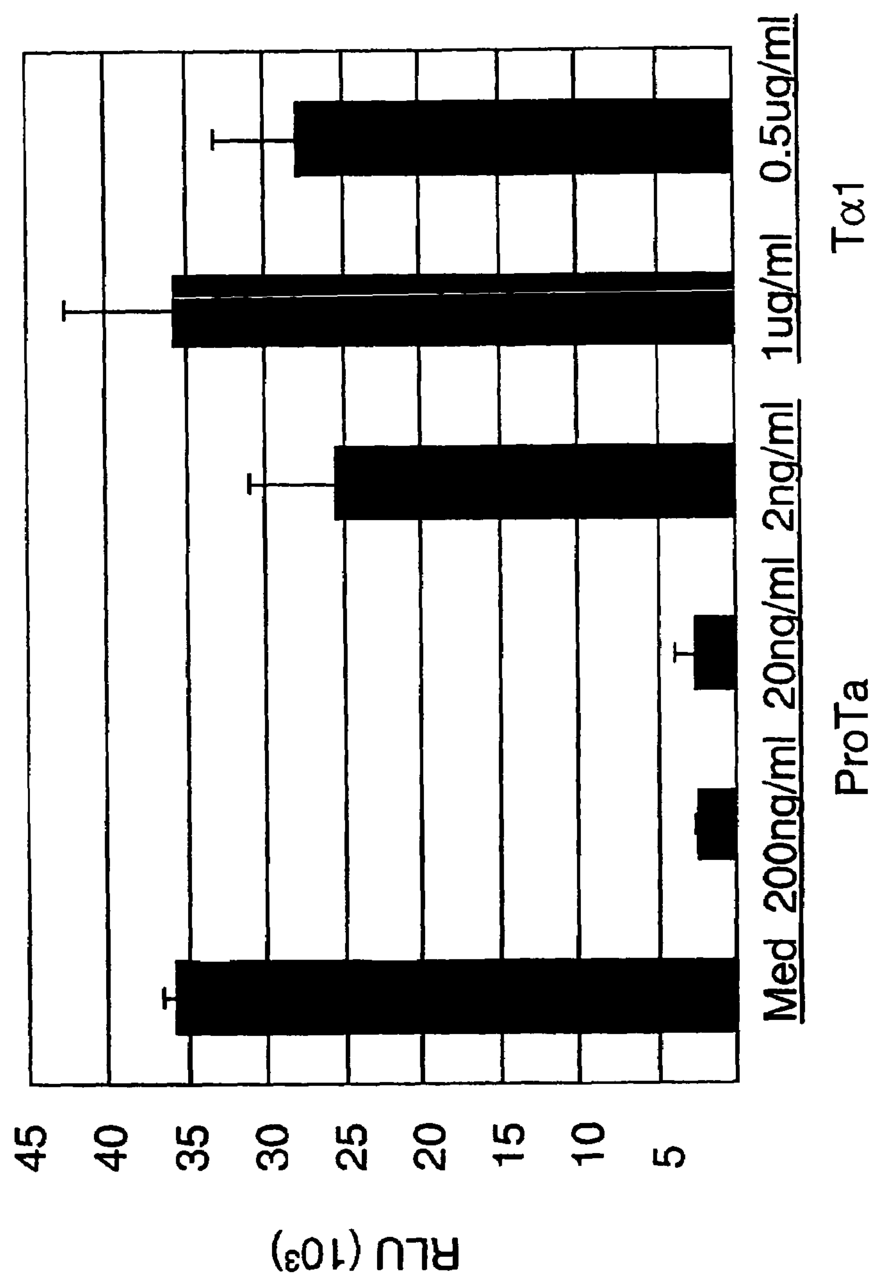

T 1 has been found in human serum and is generated by protease-mediated cleavage of ProTα (29). T 1 has been used for treatment in Hepatitis B viral infection and in HIV-1 infection as an immunomodulator (30). In addition, the plasma concentration of T 1 in HIV-1 positive individuals has been observed to be elevated (31). It has also been shown that T 1 activates DCs through toll-like receptor signaling (32) and binding of ProTα to lymphoblasts occurred through a non-thymosin alpha sequence (33). To determine whether this peptide is responsible for the anti-HIV-1 activity of ProTα, a chemically synthesized Tα1 was used to assay for activity against the $HIV_{JRFL}$ expressing luciferase reporter gene. The results showed that Tα1 (up to 1 μg/mL) exhibited no activity in this assay, whereas ProTα exhibited anti-HIV-1 activity at a concentration as low as 20 ng/mL (FIG. 6).

ProTα Inhibits HIV-1 Gene Transcription. To determine which step of the viral life cycle in macrophages is affected by treatment with ProTα, AZT (HIV-1 reverse transcription inhibitor, used here to control for early viral reverse transcription life-cycle events) or integrase inhibitors L-731 988 (to control the time of integration of HIV-1 in to the genomic DNA) were also used. Macrophages were infected with a VSV envelope pseudotyped HIV-1 (HIV-$1_{VSV}$) for 2, 24, 48 and 168 hrs (7 days). At the end of each incubation period the virus was washed out of the wells and the cells were treated with ProTα, AZT, or integrase inhibitors. ProTα was demonstrated to inhibit HIV-1 gene expression when added 24 and 48 hr post infection, while AZT had no effect when added at these time points (FIG. 7A). These findings suggest that ProTα inhibits HIV-1 gene expression after reverse transcription, which in macrophages is completed by 24 hr. Moreover, ProTα inhibited HIV-1 gene expression 48 hr post infection, by which time integration of HIV-1 in macrophages is completed since integrase inhibitors had no effect after this time (FIG. 7B). Suppression of HIV-1 gene transcription in primary macrophages by ProTα was confirmed by real time PCR. Total RNA was extracted from primary macrophages infected with HIV-$1_{VSV}$ (72 hr post infection) and treated with rProTα (200 ng/ml) or medium for 24 hr. An 80% suppression of LTR controlled luciferase reporter gene mRNA levels was revealed in rProTα treated samples, as compared to those incubated in control medium. These results confirmed that ProTα is inhibiting HIV-1 transcription (FIG. 7C). The data strongly suggest that ProTα inhibits HIV-1 gene expression post viral integration in cells of myeloid origin (primary macrophages and monocyte-derived dendritic cells). Surprisingly, treatment with ProTα even at 7 days post infection with a replication incompetent HIV-1 virus reduced HIV-1 gene expression by 80% (data not presented).

ProTα does not Induce Phosphorylation of STAT1 in Primary Macrophages and HeLa-CD4 Cells. The present inventors and their associates (16) have previously shown that activation of the signal transducer and activator of transcription-1 protein (STAT1) is necessary for inhibition of LTR activation and HIV-1 gene expression by unfractionated media conditioned by the HSV/CD8+T-cell line K#1 50K. The present results have established that ProTα inhibits replication of HIV-1 post viral integration.

Figure 8:
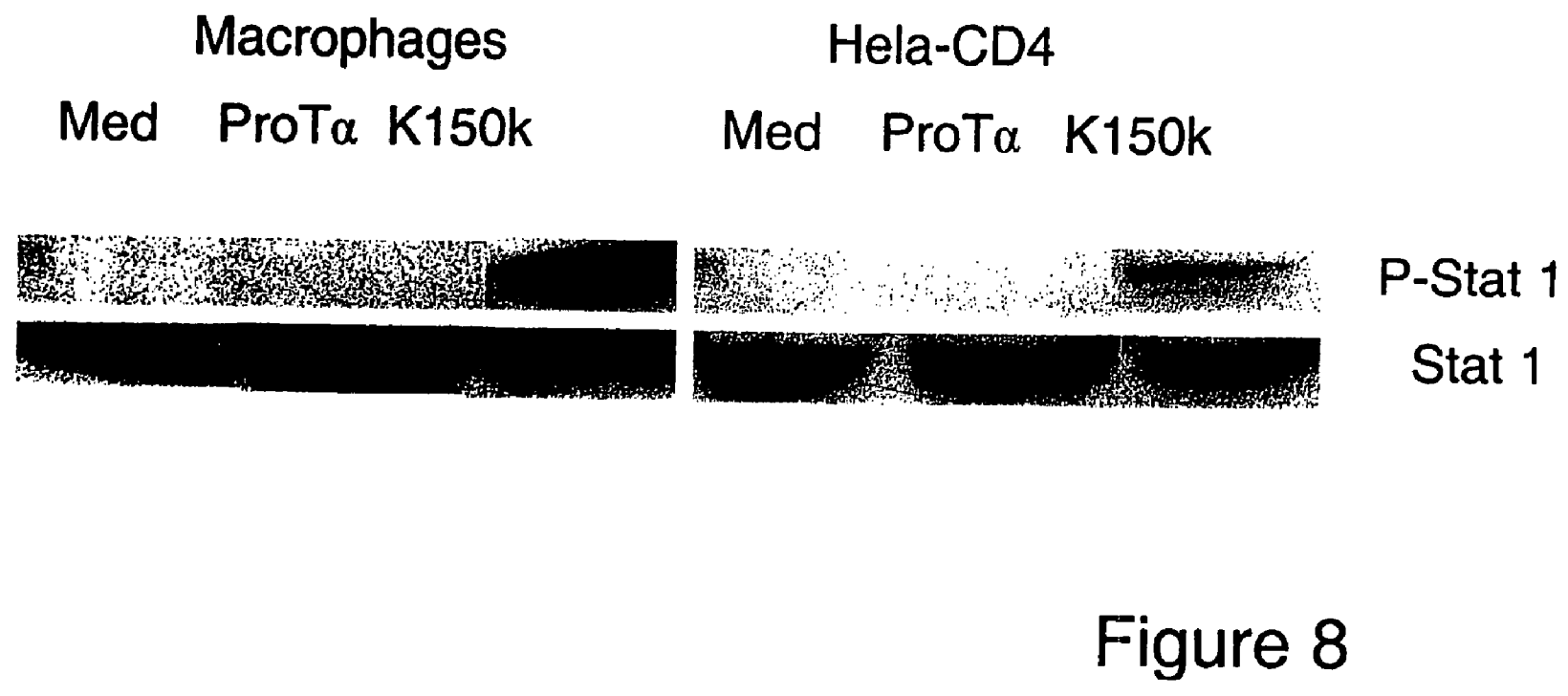

To establish whether ProTα also induces STAT1 activation in primary macrophages and HeLa-CD4 cells, such cells were briefly (15 min) incubated with ProTα protein at 1 μg/mL or 10% cell conditioned medium after incubation for 2 hr in serum free medium to reduce baseline phosphorylation. A western blot of the electrophoresed total lysate of treated and untreated cells was probed with an antibody specific for STAT1 phosphorylated at tyrosine 701 (FIG. 8). The results confirm that cell-conditioned medium diluted to 10% in fresh growth medium induces STAT1 phosphorylation in both primary macrophages and HeLa-CD4 cells, but showed that ProTα had no effect on the phosphorylation state of STAT1 in either of these cell types. These results indicate that ProTα-mediated suppression of LTR driven HIV-1 transcription does not involve STAT1 phosphorylation in primary macrophages.

Inhibition of HIV-1 Gene Transcription by ProTα is not Selective for the HIV-1 LTR Promoter. To determine whether the effect of ProTα on HIV-1 gene transcription is specific for the LTR promoter, the present inventors used two other HIV derived lentiviral vectors carrying luciferase reporter genes under control of PGK (phosphoglycerate kinase-VVPW/LBE) or CMV (cytomegalovirus-VVCW/LBE) promoters (kindly provided by Dr. L. Gusella). Macrophages were infected with HIV-$1_{VSV}$ carrying the luciferase gene, under the control of LTR, PGK or CMV promoters. At 48-72 hr post infection when viral integration is completed, ProTα at 200 ng/ml was introduced. The effects on expression of the luciferase reporter gene 24 hr post treatment indicated that ProTα inhibited expression from all three of these promoters (FIGS. 9, A, B and C), hence ProTα is not selective for the HIV-1 LTR.

Figure 10:
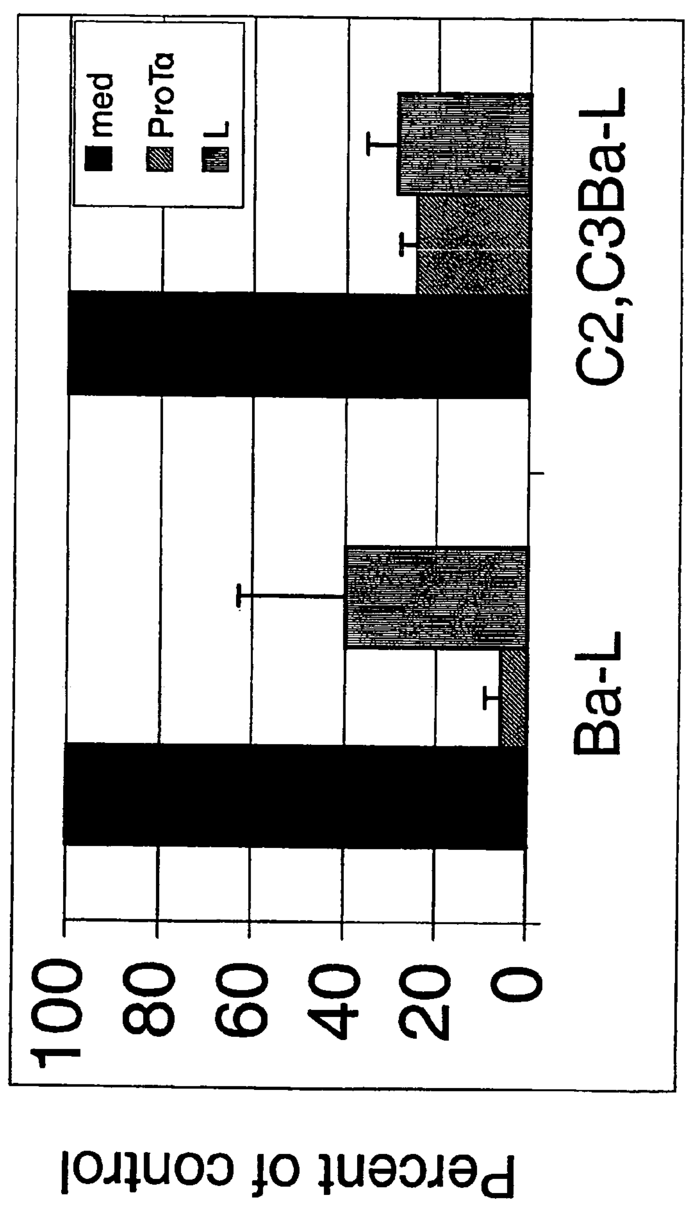

CCAAT-Box Binding Factors are Partially Responsible for Suppression of HIV-LTR Transcription by ProTα. Since ProTα inhibits HIV-LTR transcription in primary macrophages but not in primary CD4+ cells, even though CD4 cells express a receptor for ProTα (34), the present inventors hypothesized that a) cell type specific transcriptional factors are involved in suppression of HIV-LTR or b) common binding sites for these factors exist on the three promoters (PGK, CMV, HIV-LTR) used. A binding site common to all three is the CCAAT binding box which binds the C/EBP binding protein that is essential for regulation of HIV-LTR transcription in macrophages but not in CD4+ cells (35). Accordingly, the present inventors used wild type HIV-Ba-L and mutated mC2,C3-Ba-L that has point mutations in two high affinity C/EBP binding sites of CCAAT-box of LTR (kindly provided by Dr. A Henderson) to test if the CCAAT box was involved in ProTα mediated inhibition of HIV-LTR transcription in macrophages. Primary macrophages were infected with M-tropic HIV Ba-L containing either wild type 3' LTR or 3' LTR containing mutations in the high affinity C/EBP sites. The NF-B binding site was not affected by this mutation. rProTα inhibited wild type virus by 90-95%, however mutated virus replication was suppressed to a lesser degree (60-80%) (FIG. 10). Results were obtained in 3 experiments from 3 different donors of macrophages. Integrase inhibitors were used to control viral integration since replication competent viruses were used. Addition of integrase inhibitor, even at 2 hr post infection, did not completely suppress virus replication indicating that some integration has taken place. These results suggest that the CCAAT-box transcriptional factor binding site may be involved in ProTα mediated suppression of HIV-LTR promoter in primary macrophages.

Discussion

Figure 5:
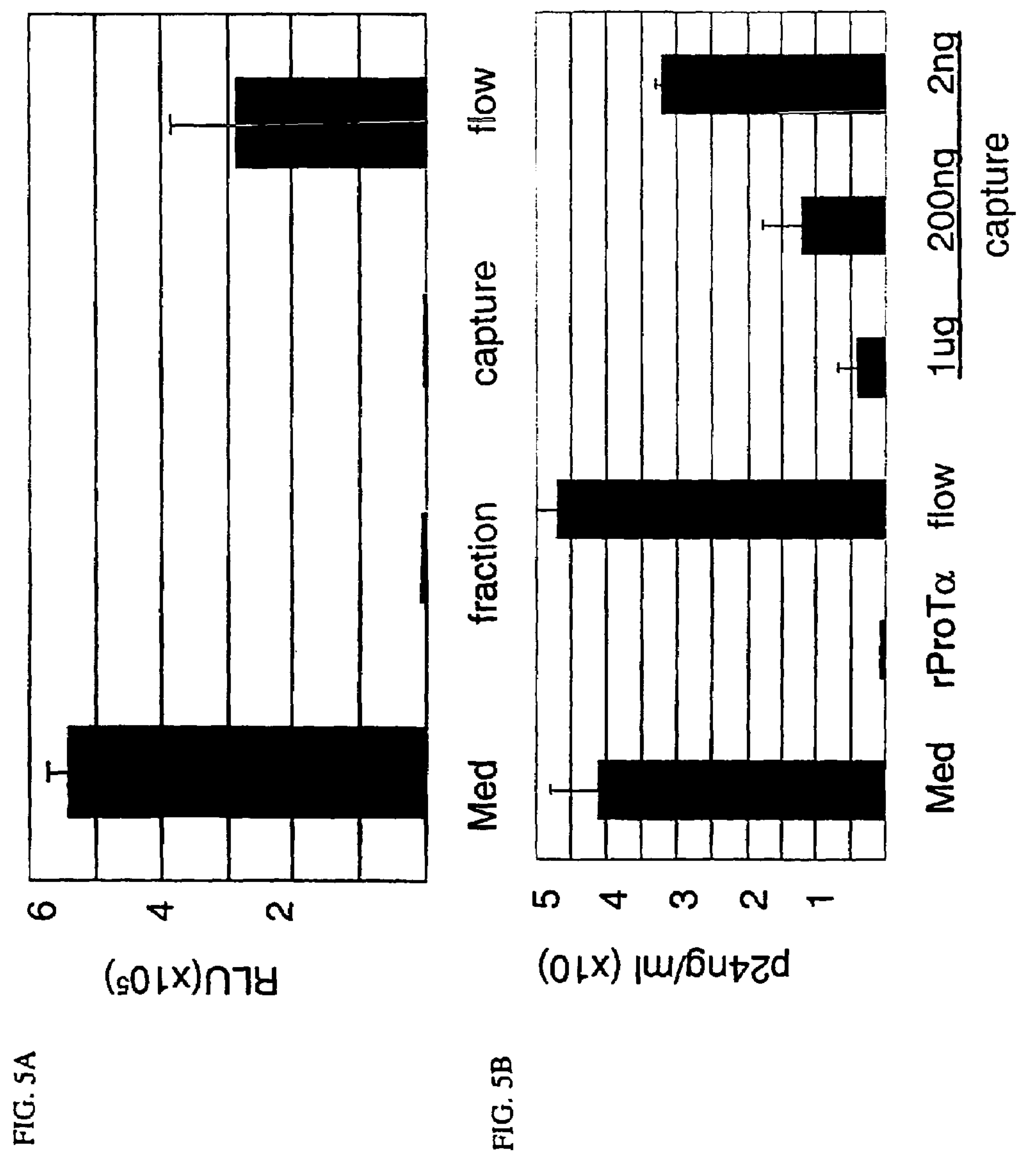

ProTα has a number of different biological activities. Intriguingly, HIV-1 infection has been shown to down regulate ProTα RNA in human T cells (36). As shown herein for the first time, the present inventors have demonstrated a novel function for this molecule, namely that ProTα is an HIV-1 suppressive factor secreted by CD8+ cells. Initially, the protein was identified by a database match of sequenced tryptic peptide from an active chromatographic fraction (FIG. 1) derived from medium conditioned by HSV-transformed CD8+ cells. The identity was confirmed by replicating the HIV-1 suppressive activity with recombinant ProTα (rProTα)—in a dose-dependant manner (FIG. 2), and then by depleting the activity from the active chromatographic fraction and from an aliquot of rProTα (FIG. 5). ProTα suppresses replication of HIV-BaL in macrophages and DCs, but has only a negligible or modest effect on replication of HIV-Ba-L or HIV-IIIB in primary CD4 lymphocytes (FIGS. 1 and 4). This was a surprising finding since CD4 lymphocytes have been shown to express receptors for ProTα (37). These results likely reflect the initial goal of the project, which was to select for macrophage protecting molecules that were identified utilizing a screening assay wherein primary macrophages were used. This experimental goal was established because of the essential role of primary macrophages in the immune system and particularly in HIV-1 infection. In addition to their very complex role in immune system defense mechanisms, macrophages also act as a reservoir of the virus. Unlike HIV-1 infected lymphocytes, which die within two to three days of infection, HIV-1 infected macrophages can continue to shed virus for two to three months after infection. In addition, since HIV-1 macrophage tropic strains are frequently present at the time of viral transmission, the pursuit of macrophage-protecting molecules becomes essential. The discovery of the HIV-1 suppressive activity of ProTα reveals this molecule to be a therapeutic and/or preventative modulator of HIV-1 infection. The potential of its efficacy is fully supported by the findings of the present inventors which show that ProTα-mediated suppression of HIV-1 infection is apparent not only with respect to laboratory strains of the virus, but also with respect to primary HIV-1 isolates (FIG. 3). Moreover, deciphering the molecular mechanisms of ProTα-mediated suppression of HIV-1 replication in primary macrophages can lead to the development of new therapeutic compounds.

The twenty-eight N-terminal amino acids of ProTα have been reported to be enzymatically cleaved in vivo to produce the immunomodulatory active peptide known as thymosin alpha 1 (Tα1) (29). It is demonstrated herein that Tα1 alone is not responsible for the HIV-1 suppressive activity of ProTα (FIG. 6). To investigate the mechanism of suppression, a replication incompetent JRFL or VSV envelope pseudotyped virus was used. The data presented herein strongly suggest that ProTα is suppressing HIV-1 gene transcription in primary macrophages and DCs (FIGS. 7, 4) and this activity is not selective for the HIV-LTR promoter (FIG. 9).

Antiviral activity isolated from supernatants of normal and transformed CD8 cells was shown to inhibit HIV-1 at the level of transcription. There are several reports indicating that CAF can inhibit HIV-1 gene transcription mediated by LTR activation (16, 38, 39). Studying the molecular mechanisms by which CAF inhibits HIV-1 replication is, however, complicated due to the lack of pure active compound. Furthermore, none of these reports confirmed the specificity of CAF mediated LTR driven transcriptional suppression.

The present inventors and their colleagues have previously described one of the mechanisms of suppression of HIV-1 gene transcription as being mediated by STAT-1 activation (16). As shown herein, the present inventors investigated whether STAT-1 activation is responsible for the suppression of HIV-1 transcription in macrophages treated with ProTα. This approach benefits from the advantage of using a single compound that appears to have anti-HIV-1 transcriptional activity. Treatment of macrophages and Hela CD4+ cells with ProTα did not induce activation of STAT-1, while treatment with 10% supernatant derived from K150K resulted in phosphorylated STAT-1 in both cell types (FIG. 8). Even though ProTα does not induce STAT-1 activation, it suppresses HIV-1 transcription in macrophages but not in Hela cells. This implies that a STAT1-independent pathway(s) is also involved in HIV-1 LTR driven transcriptional repression.

The transcriptional inhibitory effect of interferons is widely discussed in the literature (40, 41). The possibility of paracrine secretion of type one and/or two IFNs in primary macrophages in response to ProTα was investigated, but no induction of a corresponding mRNA was observed at 24 hr post treatment (data not presented). Since it was also reported that ProTα binds to the type I interferon receptor (42), it was further hypothesized that it may suppress HIV gene transcription by phosphorylation of STAT2 in a STAT1 independent manner. This mechanism of activation of STAT2 by IFN-α that inhibits NF-κB-mediated HIV-1 LTR transcription in the TNF-α signaling pathway by competing directly for p300 binding was reported (43). Moreover, ProTα was shown to bind to p300 (44). In the present experiments, however, ProTα did not induce STAT 2 phosphorylation in treated macrophages, while total supernatant (10% by volume) from K150K CD8+ cell line did (data not presented).

The present results support a cell-type dependent response to HIV-1 LTR mediated gene transcription. The present inventors show that ProTα suppresses HIV-Bal replication in macrophages via inhibition of LTR gene transcription. Using the same virus or replication incompetent virus in different cellular systems (either primary CD4 cells or Hela-CD4 cells), the present inventors showed that ProTα has modest or no effect. There is also evidence of cell type specific transcriptional modulators of HIV-1 in cells of monocytic origin versus lymphocytic origin (35). The present results are supportive of the findings of the Copeland group which suggest that factors present in CD8+ supernatants may act through several sites of the LTR to modulate transcription in a cell type-dependent manner (45). Even in cells of the same origin, but at different stages of differentiation, *Mycobacterium* tuberculosis infection of monocytes or macrophages is known to lead to induction of different transcriptional factors. In infected monocytes, for example, induction of transcription factors can suppress HIV replication, whereas induction of transcription factors in infected macrophages can induce HIV replication (46).

In addition, ProTα treatment of macrophages carrying integrated HIV leads to a 10 fold induction of IkBα mRNA, as measured by real time PCR (data not presented). Furthermore, the level of IkBα protein is increased substantially in the nucleus of macrophages after 1 hr post treatment with ProTα (data not presented). Upon stimulation IkBα is phosphorylated and degraded, and NF-κB is subsequently released and translocates into the nucleus where it activates expression of several genes including IkBα. Newly synthesized IkBα protein moves to the nucleus, removes NF-κB from its target genes and brings it back to the cytoplasm (47, 48). Recently, a novel function of IkBα has been identified, namely binding of IkB to histone deacetylase (HDAC) 1 and 3 that can lead to NF-B-independent transcriptional regulation as well. Histone deacetylase activity was also found to be associated with IkB. (49, 50) While NF B is generally considered to be a positive regulator of transcription and IkB as a repressor, there are some examples of NF B independent positive regulation of transcription by IkB (49)

In HIV-1 infected cells, the integrated proviral genome is tightly packaged by chromatin and is almost silent in the absence of stimulation. Acetylation of chromatin itself can stimulate HIV-1 gene transcription. Moreover, association of ProTα with novel histone deacetylases (HDAC) (51, 52) and interaction with histone acetyltransferase p300/CBP (HAT) (53) has lead the present inventors to hypothesize that ProTα binding to p300 can suppress its HAT activity which in turn leads to inhibition of HIV gene transcription (44, 53). But at present, a direct effect of ProTα on the enzymatic activity of p300 has not been shown in an in vitro assay system (HAT assay from Upstate, N.Y.) (44).

Treatment of macrophages carrying integrated HIV-1 with sodium butyrate (known HDAC inhibitor) leads to a 70-80% reduction in ProTα activity, suggesting the involvement of HDAC in transcriptional suppression (data not presented). Moreover, both IkBα and ProTα can bind to HDAC and form intracellular complexes with DNA (51, 52). Therefore investigating the functions of these transcriptional factors and studying the competitive binding of HDAC to IkB and/or ProTα and chromatin immunoprecipitation studies may help to further reveal how ProTα inhibits HIV-1 transcription in primary macrophages.

It has been shown that ProTα binds to HIV-1 Rev, which is known to be a post-transcriptional transactivator. Rev binds to the unspliced or partially spliced mRNA and promotes the expression of HIV-1 structural proteins in the cytoplasm (54). The present results directed to suppression of the reporter gene luciferase under control of different promoters (PGK and CMV) (FIG. 9) in different constructs that do not contain Rev genes suggest, however, that Rev protein is not involved in ProTα-mediated inhibition of HIV-1.

As shown herein, suppression of luciferase reporter gene expression under the control of HIV-LTR, PGK or CMV promoters was observed in primary macrophages treated with ProTα. (FIG. 9). All three promoters contain CCAAT/enhancer protein (C/EBP) binding sites that bind C/EBP (35, 55, 56). Furthermore, intact C/EBP beta sites were reported to be important for replication of HIV-1 in macrophages but not in lymphocytes (35). These findings conform well with the present observations that reveal that the inhibitory anti-HIV-1 activity of ProTα is evident only in cells of myeloid origin, namely macrophages and DCs (FIGS. 7, 4).

HIV-LTR contains 3 CCAAT boxes located 5' to a tandem NF-B site (57). Thus, it is possible that ProTα induces negative regulatory factors of transcription that bind to the CCAAT box and point mutation of CCAAT box of HIV-LTR promoter therefore abolished the suppressive activity of ProTα. To test this hypothesis, the present inventors used mC2,3 HIV-Bal (HIV-LTR that has a point mutation in each of the two CCAAT boxes) (35) kindly provided by Dr. A. J. Henderson. The present results suggest that CCAAT-box binding factors may be involved in the suppression of HIV-1 LTR transcription in primary macrophages. Transcription of the luciferase reporter gene mediated by wild type LTR was suppressed by 90-95%, whereas transcription from mutated mC2,3LTR was repressed to a lesser degree (60-80%). In short, point mutations in two CCAAT boxes of HIV-LTR did not absolutely abolish the activity of ProTα but rather reduced it. Since NF-B binding site on mC2,3 HIV Ba-L was intact and ProTα induces (10-fold) IkB on the mRNA level and protein level, the mechanism of suppression is likely more complex. Further experiments using a mutated NF-B binding site of HIV-LTR and using CCMT-box and NF-B binding site mutated plasmids for PGK and CMV promoters will advance the mechanistic details of the inhibitory pathway(s).

There are other transcriptional factors that bind to CCAAT boxes called B-box binding factor (Bbf). Bbf is a nuclear factor Y (NF-Y) composed of three subunits NF-YA, NF-YB, NF-YC which are all necessary for DNA binding, the coactivator molecule p300 and histone acetylase p300/CBP associated factor (PCAF; CBP stands for cAMP-response element (CRE)-binding protein (CREB)-binding protein (58, 59). In primary monocytes, there is no binding activity of NF-Y because of the lack of NF-YA subunit. This means that NF-YA is a limiting factor in the transcriptional activation of the genes (60). Unlike other CCAAT-binding proteins, NF-Y has an absolute requirement for the CCAAT nucleotide site as well as a strong preference for specific flanking sequences. Further studies are necessary to determine whether ProTα is inducing NF-Y protein synthesis and association with other transcriptional factors (HAT, HDAC) and its binding to the CCAAT promoter region and function in suppression of HIV-1 transcription.

The full HIV-1 transcriptional inhibitory activity of CAF is not attributed to only ProTα because this molecule did not have any effect on HIV-1 LTR driven transcription in Hela cells, whereas CAF does. Furthermore CAF induces STAT-1 phosphorylation, while ProTα does not (FIG. 7). This implies that a STAT1-independent pathway is also involved in HIV-1 transcriptional suppression. Treatment of macrophages with ProTα, therefore, induces other intracellular pathways that potently suppress HIV-1 replication.

REFERENCES

1. Levy, J. A. 2003. The search for the CD8+ cell anti-HIV factor (CAF). *Trends Immunol* 24:628-632.
2. DeVico, A. L., and Gallo, R. C. 2004. Control of HIV-1 infection by soluble factors of the immune response. *Nat Rev Microbiol* 2:401-413.
3. Levy, J. A., Scott, I., and Mackewicz, C. 2003. Protection from HIV/AIDS: the importance of innate immunity. *Clin Immunol* 108:167-174.
4. Mosoian, A., Teixeira, A., Caron, E., Piwoz, J., and Klotman, M. E. 2000. CD8+ cell lines isolated from HIV-1-infected children have potent soluble HIV-1 inhibitory activity that differs from beta-chemokines. *Viral Immunol* 13:481-495.
5. Walker, C. M., Moody, D. J., Stites, D. P., and Levy, J. A. 1989. CD8+ T lymphocyte control of HIV replication in cultured CD4+ cells varies among infected individuals. *Cell Immunol* 119:470-475.

6. Butera, S. T., Pisell, T. L., Limpakarnjanarat, K., Young, N. L., Hodge, T. W., Mastro, T. D., and Folks, T. M. 2001. Production of a novel viral suppressive activity associated with resistance to infection among female sex workers exposed to HIV type 1. *AIDS Res Hum Retroviruses* 17:735-744.

7. Greenberg, M. L., Lacey, S. F., Chen, C. H., Bolognesi, D. P., and Weinhold, K. J. 1997. Noncytolytic CD8 T cell-mediated suppression of HIV replication. *Springer Semin Immunopathol* 18:355-369.

8. Cocchi, F., DeVico, A. L., Garzino-Demo, A., Arya, S. K., Gallo, R. C., and Lusso, P. 1995. Identification of RANTES, MIP-1 alpha, and MIP-1 beta as the major HIV-suppressive factors produced by CD8+ T cells. *Science* 270:1811-1815.

9. Pal, R., Garzino-Demo, A., Markham, P. D., Burns, J., Brown, M., Gallo, R. C., and DeVico, A. L. 1997. Inhibition of HIV-1 infection by the beta-chemokine MDC. *Science* 278:695-698.

10. Cota, M., Mengozzi, M., Vicenzi, E., Panina-Bordignon, P., Sinigaglia, F., Transidico, P., Sozzani, S., Mantovani, A., and Poli, G. 2000. Selective inhibition of HIV replication in primary macrophages but not T lymphocytes by macrophage-derived chemokine. *Proc Natl Acad Sci USA* 97:9162-9167.

11. Proost, P., De Meester, I., Schols, D., Struyf, S., Lambeir, A. M., Wuyts, A., Opdenakker, G., De Clercq, E., Scharpe, S., and Van Damme, J. 1998. Amino-terminal truncation of chemokines by CD26/dipeptidyl-peptidase IV. Conversion of RANTES into a potent inhibitor of monocyte chemotaxis and HIV-1-infection. *J Biol Chem* 273:7222-7227.

12. Lacey, S. F., McDanal, C. B., Horuk, R., and Greenberg, M. L. 1997. The CXC chemokine stromal cell-derived factor 1 is not responsible for CD8+ T cell suppression of syncytia-inducing strains of HIV-1. *Proc Natl Acad Sci USA* 94:9842-9847.

13. Oberlin, E., Amara, A., Bachelerie, F., Bessia, C., Virelizier, J. L., Arenzana-Seisdedos, F., Schwartz, O., Heard, J. M., Clark-Lewis, I., Legler, D. F., et al. 1996. The CXC chemokine SDF-1 is the ligand for LESTR/fusin and prevents infection by T-cell-line-adapted HIV-1. *Nature* 382:833-835.

14. Baier, M., Werner, A., Bannert, N., Metzner, K., and Kurth, R. 1995. HIV suppression by interleukin-16. *Nature* 378:563.

15. Pinto, L. A., Blazevic, V., Patterson, B. K., Mac Trubey, C., Dolan, M. J., and Shearer, G. M. 2000. Inhibition of human immunodeficiency virus type 1 replication prior to reverse transcription by influenza virus stimulation. *J Virol* 74:4505-4511.

16. Chang, T. L., Mosoian, A., Pine, R., Klotman, M. E., and Moore, J. P. 2002. A soluble factor(s) secreted from CD8 (+) T lymphocytes inhibits human immunodeficiency virus type 1 replication through STAT1 activation. *J Virol* 76:569-581.

17. Wada, M., Wada, N. A., Shirono, H., Taniguchi, K., Tsuchie, H., and Koga, J. 2001. Amino-terminal fragment of urokinase-type plasminogen activator inhibits HIV-1 replication. *Biochem Biophys Res Commun* 284:346-351.

18. Geiben-Lynn, R., Kursar, M., Brown, N. V., Kerr, E. L., Luster, A. D., and Walker, B. D. 2001. Noncytolytic inhibition of X4 virus by bulk CD8(+) cells from human immunodeficiency virus type 1 (HIV-1)-infected persons and HIV-1-specific cytotoxic T lymphocytes is not mediated by beta-chemokines. *J Virol* 75:8306-8316.

19. Moriuchi, H., Moriuchi, M., Combadiere, C., Murphy, P. M., and Fauci, A. S. 1996. CD8+ T-cell-derived soluble factor(s), but not beta-chemokines RANTES, MIP-1 alpha, and MIP-1 beta, suppress HIV-1 replication in monocyte/macrophages. *Proc Natl Acad Sci USA* 93:15341-15345.

20. Haritos, A. A., Blacher, R., Stein, S., Caldarella, J., and Horecker, B. L. 1985. Primary structure of rat thymus prothymosin alpha. *Proc Natl Acad Sci USA* 82:343-346.

21. Sukhacheva, E. A., Evstafieva, A. G., Fateeva, T. V., Shakulov, V. R., Efimova, N. A., Karapetian, R. N., Rubtsov, Y. P., and Vartapetian, A. B. 2002. Sensing prothymosin alpha origin, mutations and conformation with monoclonal antibodies. *J Immunol Methods* 266:185-196.

22. Boan, F., Vinas, A., Buceta, M., Dominguez, F., Sanchez, L., and Gomez-Marquez, J. 2001. Prothymosin alpha, a mammalian c-myc-regulated acidic nuclear protein, provokes the decondensation of human chromosomes in vitro. *Cytogenet Cell Genet* 93:171-174.

23. Goodall, G. J., Dominguez, F., and Horecker, B. L. 1986. Molecular cloning of cDNA for human prothymosin alpha. *Proc Natl Acad Sci USA* 83:8926-8928.

24. Evstafieva, A. G., Belov, G. A., Rubtsov, Y. P., Kalkum, M., Joseph, B., Chichkova, N. V., Sukhacheva, E. A., Bogdanov, A. A., Pettersson, R. F., Agol, V. I., et al. 2003. Apoptosis-related fragmentation, translocation, and properties of human prothymosin alpha. *Exp Cell Res* 284:211-223.

25. Vartapetian, A. B. 1992. [Myc proteins, prothymosin alpha, and cell division]. *Biokhimiia* 57:477-478.

26. Tao, L., Wang, R. H., Enkemann, S. A., Trumbore, M. W., and Berger, S. L. 1999. Metabolic regulation of protein-bound glutamyl phosphates: insights into the function of prothymosin alpha. *J Cell Physiol* 178:154-163.

27. Panneerselvam, C., Haritos, A. A., Caldarella, J., and Horecker, B. L. 1987. Prothymosin alpha in human blood. *Proc Natl Acad Sci USA* 84:4465-4469.

28. Franco, F. J., Diaz, C., Barcia, M., Arias, P., Gomez-Marquez, J., Soriano, F., Mendez, E., and Freire, M. 1989. Synthesis and apparent secretion of prothymosin alpha by different subpopulations of calf and rat thymocytes. *Immunology* 67:263-268.

29. Sarandeses, C. S., Covelo, G., Diaz-Jullien, C., and Freire, M. 2003. Prothymosin alpha is processed to thymosin alpha 1 and thymosin alpha 11 by a lysosomal asparaginyl endopeptidase. *J Biol Chem* 278:13286-13293.

30. Garaci, E., Pica, F., Rasi, G., Palamara, A. T., and Favalli, C. 1997. Combination therapy with BRMs in cancer and infectious diseases. *Mech Ageing Dev* 96:103-116.

31. Rubinstein, A., Novick, B. E., Sicklick, M. J., Bernstein, L. J., Incefy, G. S., Naylor, P. H., and Goldstein, A. L. 1986. Circulating thymulin and thymosin-alpha 1 activity in pediatric acquired immune deficiency syndrome: in vivo and in vitro studies. *J Pediatr* 109:422-427.

32. Romani, L., Bistoni, F., Gaziano, R., Bozza, S., Montagnoli, C., Perruccio, K., Pitzurra, L., Bellocchio, S., Velardi, A., Rasi, G., et al. 2004. Thymosin alpha 1 activates dendritic cells for antifungal Th1 resistance through toll-like receptor signaling. *Blood* 103:4232-4239.

33. Cordero, O. J., Sarandeses, C. S., and Nogueira, M. 1996. Binding of 125I-prothymosin alpha to lymphoblasts through the non-thymosin alpha 1 sequence. *Life Sci* 58:1757-1770.

34. Pineiro, A., Begona Bugia, M., Pilar Arias, M., Cordero, O. J., and Nogueira, M. 2001. Identification of receptors for prothymosin alpha on human lymphocytes. *Biol Chem* 382:1473-1482.

35. Henderson, A. J., and Calame, K. L. 1997. CCAAT/enhancer binding protein (C/EBP) sites are required for HIV-1 replication in primary macrophages but not CD4(+) T cells. *Proc Natl Acad Sci USA* 94:8714-8719.

36. Ryo, A., Suzuki, Y., Arai, M., Kondoh, N., Wakatsuki, T., Hada, A., Shuda, M., Tanaka, K., Sato, C., Yamamoto, M., et al. 2000. Identification and characterization of differentially expressed mRNAs in HIV type 1-infected human T cells. *AIDS Res Hum Retroviruses* 16:995-1005.

37. Cordero, O. J., Sarandeses, C., and Nogueira, M. 1995. Prothymosin alpha receptors on lymphocytes. *J Interferon Cytokine Res* 15:731-737.

38. Mackewicz, C. E., Blackbourn, D. J., and Levy, J. A. 1995. CD8+ T cells suppress human immunodeficiency virus replication by inhibiting viral transcription. *Proc Natl Acad Sci USA* 92:2308-2312.

39. Copeland, K. F. 2001. CD8+ T cell suppressor factors and the control of infection, replication and transcription of human immunodeficiency virus. *Arch Immunol Ther Exp* (*Warsz*) 49:13-18.

40. Kornbluth, R. S., Oh, P. S., Munis, J. R., Cleveland, P. H., and Richman, D. D. 1990. The role of interferons in the control of HIV replication in macrophages. *Clin Immunol Immunopathol* 54:200-219.

41. Gendelman, H. E., Baca, L. M., Turpin, J., Kalter, D. C., Hansen, B., Orenstein, J. M., Dieffenbach, C. W., Friedman, R. M., and Meltzer, M. S. 1990. Regulation of HIV replication in infected monocytes by IFN-alpha. Mechanisms for viral restriction. *J Immunol* 145:2669-2676.

42. Zav'Yalov, V. P., Navolotskaya, E. V., Vasilenko, R. N., Abramov, V. M., Volodina, E. Y., Roslovtseva, O. A., Prusakov, A. N., and Kaurov, O. A. 1995. The sequence 130-137 of human interferon-alpha 2 is involved in the competition of interferon, prothymosin alpha and cholera toxin B subunit for common receptors on human fibroblasts. *Mol Immunol* 32:425-431.

43. Hottiger, M. O., Felzien, L. K., and Nabel, G. J. 1998. Modulation of cytokine-induced HIV gene expression by competitive binding of transcription factors to the coactivator p300. *Embo J* 17:3124-3134.

44. Karetsou, Z., Kretsovali, A., Murphy, C., Tsolas, O., and Papamarcaki, T. 2002. Prothymosin alpha interacts with the CREB-binding protein and potentiates transcription. *EMBO Rep* 3:361-366.

45. Maslove, D. M., Ni, L. W., Hawley-Foss, N. C., Badley, A. D., and Copeland, K. F. 2001. Modulation of HIV transcription by CD8(+) cells is mediated via multiple elements of the long terminal repeat. *Clin Exp Immunol* 125: 102-109.

46. Weiden, M., Tanaka, N., Qiao, Y., Zhao, B. Y., Honda, Y., Nakata, K., Canova, A., Levy, D. E., Rom, W. N., and Pine, R. 2000. Differentiation of monocytes to macrophages switches the *Mycobacterium* tuberculosis effect on HIV-1 replication from stimulation to inhibition: modulation of interferon response and CCAAT/enhancer binding protein beta expression. *J Immunol* 165:2028-2039.

47. Johnson, C., Van Antwerp, D., and Hope, T. J. 1999. An N-terminal nuclear export signal is required for the nucleocytoplasmic shuttling of IkappaBalpha. *Embo J* 18:6682-6693.

48. Huang, T. T., and Miyamoto, S. 2001. Postrepression activation of NF-kappaB requires the amino-terminal nuclear export signal specific to IkappaBalpha. *Mol Cell Biol* 21:4737-4747.

49. Viatour, P., Legrand-Poels, S., van Lint, C., Warnier, M., Merville, M. P., Gielen, J., Piette, J., Bours, V., and Chariot, A. 2003. Cytoplasmic IkappaBalpha increases NF-kappaB-independent transcription through binding to histone deacetylase (HDAC) 1 and HDAC3. *J Biol Chem* 278: 46541-46548.

50. Aguilera, C., Hoya-Arias, R., Haegeman, G., Espinosa, L., and Bigas, A. 2004. Recruitment of IkappaBalpha to the hes1 promoter is associated with transcriptional repression. *Proc Natl Acad Sci USA* 101:16537-16542.

51. Knight, J. S., Lan, K., Subramanian, C., and Robertson, E. S. 2003. Epstein-Barr virus nuclear antigen 3C recruits histone deacetylase activity and associates with the corepressors mSin3A and NCoR in human B-cell lines. *J Virol* 77:4261-4272.

52. Gomez-Marquez, J., and Rodriguez, P. 1998. Prothymosin alpha is a chromatin-remodelling protein in mammalian cells. *Biochem J* 333 (Pt 1): 1-3.

53. Subramanian, C., Hasan, S., Rowe, M., Hottiger, M., Orre, R., and Robertson, E. S. 2002. Epstein-Barr virus nuclear antigen 3C and prothymosin alpha interact with the p300 transcriptional coactivator at the CHI and CH3/HAT domains and cooperate in regulation of transcription and histone acetylation. *J Virol* 76:4699-4708.

54. Kubota, S., Adachi, Y., Copeland, T. D., and Oroszlan, S. 1995. Binding of human prothymosin alpha to the leucine-motif/activation domains of HTLV-I Rex and HIV-1 Rev. *Eur J Biochem* 233:48-54.

55. Burns, L. J., Waring, J. F., Reuter, J. J., Stinski, M. F., and Ginder, G. D. 1993. Only the HLA class I gene minimal promoter elements are required for transactivation by human cytomegalovirus immediate early genes. *Blood* 81:1558-1566.

56. Pfeifer, G. P., Tanguay, R. L., Steigerwald, S. D., and Riggs, A. D. 1990. In vivo footprint and methylation analysis by PCR-aided genomic sequencing: comparison of active and inactive X chromosomal DNA at the CpG island and promoter of human PGK-1. *Genes Dev* 4:1277-1287.

57. Tesmer, V. M., Rajadhyaksha, A., Babin, J., and Bina, M. 1993. NF-IL6-mediated transcriptional activation of the long terminal repeat of the human immunodeficiency virus type 1. *Proc Natl Acad Sci USA* 90:7298-7302.

58. Faniello, M. C., Chirico, G., Quaresima, B., Cuda, G., Allevato, G., Bevilacqua, M. A., Baudi, F., Colantuoni, V., Cimino, F., Venuta, S., et al. 2002. An alternative model of H ferritin promoter transactivation by c-Jun. *Biochem J* 363:53-58.

59. Faniello, M. C., Bevilacqua, M. A., Condorelli, G., de Crombrugghe, B., Maity, S. N., Avvedimento, V. E., Cimino, F., and Costanzo, F. 1999. The B subunit of the CAAT-binding factor NFY binds the central segment of the Co-activator p300. *J Biol Chem* 274:7623-7626.

60. Marziali, G., Perrotti, E., Ilari, R., Coccia, E. M., Mantovani, R., Testa, U., and Battistini, A. 1999. The activity of the CCAAT-box binding factor NF-Y is modulated through the regulated expression of its A subunit during monocyte to macrophage differentiation: regulation of tissue-specific genes through a ubiquitous transcription factor. *Blood* 93:519-526.

61. Naldini, L. 1998. Lentiviruses as gene transfer agents for delivery to non-dividing cells. *Curr Opin Biotechnol* 9:457-463.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating a patient with an infectious disease, wherein said infectious disease is caused by infection with human immunodeficiency virus-1, said method comprising:

(a) administering an isolated Prothymosin alpha molecule, wherein said Prothymosin alpha molecule is a polypeptide comprising the amino acid sequence of SEQ ID NO: 2 to the patient in a therapeutically effective amount, wherein said therapeutically effective amount reduces the symptoms associated with said infectious disease.

2. The method of claim 1, wherein said isolated Prothymosin alpha molecule is a purified naturally occurring polypeptide.

3. The method of claim 1, wherein said isolated Prothymosin alpha molecule is a purified recombinant polypeptide.

4. The method of claim 1, wherein said isolated Prothymosin alpha molecule is a purified synthetic polypeptide.

5. The method of claim 1, wherein said isolated Prothymosin alpha molecule is a non phosphorylated polypeptide.

6. The method of claim 1, wherein said isolated Prothymosin alpha molecule is administered topically, orally, parenterally, or as an aerosol.

7. The method of claim 1, wherein said isolated Prothymosin alpha molecule is administered as a composition, wherein said composition comprises the isolated Prothymosin alpha molecule and a pharmaceutically acceptable carrier.

8. The method of claim 7, wherein said composition is administered topically, orally, parenterally, or as an aerosol.

9. The method of claim 1, wherein said infectious disease is associated with infection of macrophages and/or dendritic cells.

10. The method of claim 1, wherein said isolated Prothymosin alpha molecule is a polypeptide consisting of an amino acid sequence of SEQ ID NO: 2.

* * * * *

SEQUENCE LISTING

<160> NUMBER OF SEQ ID NOS: 15

<210> SEQ ID NO 1
<211> LENGTH: 2770
<212> TYPE: DNA
<213> ORGANISM: Homo sapiens

<400> SEQUENCE: 1

```
atttattttt ggaacataac ctgccgcctt tctagacggc tcgaggggcg ggctctttgc     60
acttggaagc aggctgatgg gcgtgagtgt ccggggctcg tccacccggc cggacgggct    120
gggggctgtg gcgccacatg gctccttttt cctgggaagc gccagggggc agtgggaacc    180
gccaccgggg ccgctgtagc gggccttaaa ggatgggaaa ccttgatcac agatgccccc    240
cgccggcctt ccttccacca gaccagtggg agagggaccg caggggcatc aggcctttct    300
caacatgcga ctcttaattt gggacggaca gaacagccgt acagaccagt agttctcagc    360
gcctttgctt accctgggtt gctcagaaga cttactggtt actggttcct tcttcccttt    420
tgaaggactt aaaggagaag aaggaagttg tggaagaggc agaaaatgga agagacgccc    480
ctgctaacgg gaatgctgtg agtgtctgct ttgctcctga gccctggcag ctaccgcccc    540
acaaaatttt tcctgttcta ctttaaacat acctatatat gtgtgtgtat gtgtatatgt    600
atagctttcc acagtggcag tatcgtagcc aatgagcttt acccgaggcg cgattattgc    660
tagttaaata tttataaaaa cctttcgagc agcgcctgaa caagaatagg ttcagaggag    720
actccggtag tctgagtttg ggcttggccc agggtgggga aaagcccttg tcctggggca    780
gttaatgtgc aggtttcacg atggagcctg gagggtgttg actggagaag ggtctctggg    840
gtgggcttgg cttggctggg ctgtagatgc agccgccagc ctctggtggg aggccgggca    900
tcaggagcaa cgctctgtcc agcctggggc caactggtaa tgacatggcc tgttttctgt    960
cgaggagaat gaggaaaatg gggagcagga ggctgacaat gaggtagacg aagaagagga   1020
agaaggtggg gaggaagagg aggaggaaga agaaggtgat ggtgagtagc cttgtctatc   1080
ttcccctttt caggtacttt ttcctggcct tgtctggcag aaggggaagg aaggaattgg   1140
ggctcctggg agtgggacaa tggtacttgg ggccagtgga ccacatggcc ctgggcaccc   1200
acctgtagag tcagggaagg tctccctgac atggagttgt gcccatgccc actcacactc   1260
actcgcacac ctgaaagttt ctttcgtgca gctctgaaag ccactgatct attgggctgg   1320
ccttttgggg tgcagctgct tgggcctctc tcctctggag agtcccacct gtgtagtggg   1380
cgtgggtgcc ctgattgggc ccagttgcag gcagtagagg cagggcaggg accttgcagt   1440
ccactacatg ttcctcggga tttccccagg agccacagta ggagggaagt gtggtttacc   1500
tggcctttga ttctctccag gtgaggaaga ggatggagat gaagatgagg aagctgagtc   1560
agctacgggc aagcgggcag ctgaagatga tgaggtgggt tctggcttga gaagaagggg   1620
ggtttggcat ctgggtctcc ccacctgcct ttagctgagg tgctcaagct gcggagggac   1680
tgtttctgac tttgtaggtg gccactgtgt ggtcctgaat cttaagaaca ggaaggaaac   1740
agggctgggc tcaacttccc agaggccttg ggctgtggag ctgggggtcc ctggttcttg   1800
ctctgccagc aggagctgag gcagtgggct ggatagggct cctggggttg gaggggcctt   1860
tgacagtctt tctctgctta ggatgacgat gtcgatacca agaagcagaa gaccgacgag   1920
gatgactaga cagcaaaaaa ggaaaagtta aactaaaaaa aaaaaggccg ccgtgaccca   1980
ttcaccctcc acttcccgtc tcagaatcta aacgtggtca ccttcgagta gagaggcccg   2040
```

```
cccgcccacc gtgggcagtg ccacccgcag atgacacgcg ctctccacca cccaacccaa   2100

accatgagaa tttgcaacag gggaggaaaa aagaaccaaa acttccaagg ccctgctttt   2160

tttcttaaaa gtactttaaa aaggaaattt gtttgtattt tttatttaca ttttatattt   2220

ttgtacatat tgttagggtc agccattttt aatgatctcg gatgaccaaa ccagccttcg   2280

gagcgttctc tgtcctactt ctgactttac ttgtggtgtg accatgttca ttataatctc   2340

aaaggagaaa aaaaaccttg taaaaaaagc aaaaatgaca acagaaaaac aatcttattc   2400

cgagcattcc agtaactttt ttgtgtatgt acttagctgt actataagta gttggtttgt   2460

atgagatggt taaaaaggcc aaagataaaa ggtttctttt tttttccttt tttgtctatg   2520

aagttgctgt ttattttttt tggcctgttt gatgtatgtg tgaaacaatg ttgtccaaca   2580

ataaacagga attttatttt gctgagttgt tctacaaaaa aaaaaaaaaa aaaaaaaaaa   2640

aaaaaaaaaa aaaaaaaaaa aaaaaaaaaa aaaaaaaaaa aaaaaaaaaa aaaaaaaaaa   2700

aaaaaaaaaa aaaaaaaaaa aaaaaaaaaa aaaaaaaaaa aaaaaaaaaa agaaaaaaaa   2760

aaaaaaaaaa                                                          2770
```

<210> SEQ ID NO 2
<211> LENGTH: 111
<212> TYPE: PRT
<213> ORGANISM: Homo sapiens

<400> SEQUENCE: 2

```
Met Ser Asp Ala Ala Val Asp Thr Ser Ser Glu Ile Thr Thr Lys Asp
 1               5                  10                  15

Leu Lys Glu Lys Lys Glu Val Val Glu Glu Ala Glu Asn Gly Arg Asp
            20                  25                  30

Ala Pro Ala Asn Gly Asn Ala Glu Asn Glu Glu Asn Gly Glu Gln Glu
        35                  40                  45

Ala Asp Asn Glu Val Asp Glu Glu Glu Glu Glu Gly Gly Glu Glu Glu
    50                  55                  60

Glu Glu Glu Glu Glu Gly Asp Gly Glu Glu Glu Asp Gly Asp Glu Asp
65                  70                  75                  80

Glu Glu Ala Glu Ser Ala Thr Gly Lys Arg Ala Ala Glu Asp Asp Glu
                85                  90                  95

Asp Asp Asp Val Asp Thr Lys Lys Gln Lys Thr Asp Glu Asp Asp
            100                 105                 110
```

<210> SEQ ID NO 3
<211> LENGTH: 1397
<212> TYPE: DNA
<213> ORGANISM: Homo sapiens

<400> SEQUENCE: 3

```
tcattaattt tgggaaaaat gcttcaataa tggcttttgg agaaaatgaa aagatgccac     60

attaattgta gacaaccatt ttaagatata tttcattccg ccccactggc tgctctgaaa    120

agccatcttt gcattgttcc tccttgctcg ccgcagccgc ctccgccgcg cgcctcctcc    180

gccgccgcgg actgcggcag ctttatcgcc agagtccctg aactctcgct ttctttttaa    240

tcccctgcat cggatcaccg gcgtgcccca ccatgtcaga cgcagccgta gacgccagct    300

ccgaaatcac catcaaggac ttaaaggaga agaaggaagt tgtggaagag gcagaaaatg    360

gaagagacgc ccctgctaac gggaatgcta atgaggaaaa tggggagcag gaagctgaca    420

gtgaagtaga tgaagaagag gaagaaggtg gggaggaaga ggaggaggaa gaagaaggtg    480
```

```
atggtgagga agaggatgga gatgaagatg aggaagctga gtcacctacg ggcaagcggg    540

cagctgaaga tgatgaggat gacgatgtcg ataccaagaa gcagaagacc gacgaggatg    600

actagacagc aaaaaaggaa aagttaaact aaaaaaaaag gccgccgtga cctattcacc    660

ctccacttcc cgtctcagaa tctaaacgtg gtcaccttca agtagagagg cccgcctgcc    720

caccgtgggc agtgccaccc acagatgata cgcgctctcc accacccaac ccaaaccatg    780

agaatttgca acaggggagg aaaaaagaac caaaacttcc aaggccatgc tttttttctt    840

aaaagtactt taaaaaggaa atttgtttgt atttttattt tacattttat atttttatac    900

atattgttag ggtcagccat ttttaatgat ctcggatgac caaaccagcc ttgggagcgt    960

tctgtcctac ttctgacttt acttgtggtg tgaccatgtt cattataatc tcaaaggaga   1020

aaaaaacctt gtaaaaaaag caaaaatgac aacagaaaaa caatcttatt ctgagcattc   1080

cagtaacttt tttgtgtatg tacttagctg tactataagg agttggtttg tatgagatgg   1140

ttaaaaaggc caaagataaa aggtttattt tttttccttt tttgtctatg aagttgctgt   1200

ttattttttt tggcctgttt gatgtatgtg tgaaacaatg ttgtccaaca ataaacagga   1260

attttatttt gctgagttgt tctaaaaaaa aaaaaaagat gtatttcatt ccaactacaa   1320

agacattaca agtgtttgag atggtaaaca aactgattat cataatttga tcaatatgca   1380

atgtacacat gtactga                                                  1397

<210> SEQ ID NO 4
<211> LENGTH: 1233
<212> TYPE: DNA
<213> ORGANISM: Homo sapiens

<400> SEQUENCE: 4

ccccactggc tgctctgaaa agccatcttt gcattgttcc tcatccgcct ccttgctcgc     60

cgcagccgcc tccgccgcgc gcctcctccg ccgccgcgga ctccggcagc tttatcgcca    120

gagtccctga actctcgctt tctttttaat cccctgcatc ggatcaccgg cgtgccccac    180

catgtcagac gcagccgtag acaccagctc cgaaatcacc accaaggact taaaggagaa    240

gaaggaagtt gtggaagagg cagaaaatgg aagagacgcc cctgctaacg ggaatgctaa    300

tgaggaaaat ggggagcagg aggctgacaa tgaggtagac gaagaagagg aagaaggtgg    360

ggaggaagag gaggaggaag aagaaggtga tggtgaggag gagggtggag atgaagatga    420

ggaagctgag tcagctacgg gcaagcgggc agctgaagat gatgaggatg acgatgtcga    480

taccaagaag cagaagaccg acgaggatga ctagacagca aaaaaggaaa agttaaacta    540

aaaaaaaaaa ggccgccgtg acctattcac cctccacttc ccgtctcaga atctaaacgt    600

ggtcaccttc gagtagagag gcccgcccgc ccaccgtggg cagtgccacc cgcagatgac    660

acgcgctctc caccacccaa cccaaaccat gagaatttgc aacaggggag gaaaaaagaa    720

ccaaaacttc caaggccctg ctttttttct taaaagtact ttaaaaagga aatttgtttg    780

tatttttat ttacatttta tatttttgta catattgtta gggtcagcca tttttaatga     840

tctcggatga ccaaaccagc cttcggagcg ttctctgtcc tacttctgac tttacttgtg    900

gtgtgaccat gttcattata atctcaaagg agaaaaaaaa ccttgtaaaa aaagcaaaaa    960

tgacaacaga aaaacaatct tattccgagc attccagtaa cttttttgtg tatgtactta   1020

gctgtactat aagtagttgg tttgtatgag atggttaaaa aggccaaaga taaaaggttt   1080

cttttttttt ccttttttgt ctatgaagtt gctgtttatt ttttttggcc tgtttgatgt   1140
```

```
atgtgtgaaa caatgttgtc caacaataaa caggaatttt attttgctga gttgttctaa   1200

cagaaaaaaa aaaaaaaaaa aaaaaaaaaa aaa                                1233


<210> SEQ ID NO 5
<211> LENGTH: 110
<212> TYPE: PRT
<213> ORGANISM: Homo sapiens

<400> SEQUENCE: 5

Met Ser Asp Ala Ala Val Asp Thr Ser Ser Glu Ile Thr Thr Lys Asp
 1               5                  10                  15

Leu Lys Glu Lys Lys Glu Val Val Glu Glu Ala Glu Asn Gly Arg Asp
            20                  25                  30

Ala Pro Ala Asn Gly Asn Ala Asn Glu Glu Asn Gly Glu Gln Glu Ala
        35                  40                  45

Asp Asn Glu Val Asp Glu Glu Glu Glu Glu Gly Gly Glu Glu Glu Glu
    50                  55                  60

Glu Glu Glu Glu Gly Asp Gly Glu Glu Glu Gly Gly Asp Glu Asp Glu
65                  70                  75                  80

Glu Ala Glu Ser Ala Thr Gly Lys Arg Ala Ala Glu Asp Asp Glu Asp
                85                  90                  95

Asp Asp Val Asp Thr Lys Lys Gln Lys Thr Asp Glu Asp Asp
            100                 105                 110


<210> SEQ ID NO 6
<211> LENGTH: 110
<212> TYPE: PRT
<213> ORGANISM: Pongo pygmaeus

<400> SEQUENCE: 6

Met Ser Asp Ala Ala Val Asp Thr Ser Ser Glu Ile Thr Thr Lys Asp
 1               5                  10                  15

Leu Lys Glu Lys Lys Glu Val Val Glu Glu Ala Glu Asn Gly Arg Asp
            20                  25                  30

Val Pro Ala Asn Gly Asn Ala Asn Glu Glu Asn Gly Glu Gln Glu Ala
        35                  40                  45

Asp Asn Glu Val Asp Glu Glu Glu Glu Glu Gly Gly Glu Glu Glu Glu
    50                  55                  60

Glu Glu Glu Glu Gly Asp Gly Glu Glu Glu Asp Gly Asp Glu Asp Glu
65                  70                  75                  80

Glu Ala Glu Ser Ala Thr Gly Lys Arg Ala Ala Glu Asp Asp Glu Asp
                85                  90                  95

Asp Asp Val Asp Thr Lys Lys Gln Lys Thr Asp Glu Asp Asp
            100                 105                 110


<210> SEQ ID NO 7
<211> LENGTH: 111
<212> TYPE: PRT
<213> ORGANISM: Mus musculus

<400> SEQUENCE: 7

Met Ser Asp Ala Ala Val Asp Thr Ser Ser Glu Ile Thr Thr Lys Asp
 1               5                  10                  15

Leu Lys Glu Lys Lys Glu Val Val Glu Glu Ala Glu Asn Gly Arg Asp
            20                  25                  30

Ala Pro Ala Asn Gly Asn Ala Gln Asn Glu Glu Asn Gly Glu Gln Glu
        35                  40                  45
```

-continued

```
Ala Asp Asn Glu Val Asp Glu Glu Glu Glu Glu Gly Gly Glu Glu Glu
    50                  55                  60

Glu Glu Glu Glu Glu Gly Asp Gly Glu Glu Glu Asp Gly Asp Glu Asp
65                  70                  75                  80

Glu Glu Ala Glu Ala Pro Thr Gly Lys Arg Val Ala Glu Asp Asp Glu
                85                  90                  95

Asp Asp Asp Val Asp Thr Lys Lys Gln Lys Thr Glu Glu Asp Asp
            100                 105                 110


<210> SEQ ID NO 8
<211> LENGTH: 112
<212> TYPE: PRT
<213> ORGANISM: Rattus norvegicus

<400> SEQUENCE: 8

Met Ser Asp Ala Ala Val Asp Thr Ser Ser Glu Ile Thr Thr Lys Asp
 1               5                  10                  15

Leu Lys Glu Lys Lys Glu Val Val Glu Glu Ala Glu Asn Gly Arg Asp
            20                  25                  30

Ala Pro Ala Asn Gly Asn Ala Gln Asn Glu Glu Asn Gly Glu Gln Glu
        35                  40                  45

Ala Asp Asn Glu Val Asp Glu Glu Glu Glu Glu Gly Gly Glu Glu Glu
    50                  55                  60

Glu Glu Glu Glu Glu Gly Asp Gly Glu Glu Glu Asp Gly Asp Glu Asp
65                  70                  75                  80

Glu Glu Ala Glu Ala Pro Thr Gly Lys Arg Val Ala Glu Asp Asp Glu
                85                  90                  95

Asp Asp Asp Val Glu Thr Lys Lys Gln Lys Lys Thr Asp Glu Asp Asp
            100                 105                 110


<210> SEQ ID NO 9
<211> LENGTH: 109
<212> TYPE: PRT
<213> ORGANISM: Bos taurus

<400> SEQUENCE: 9

Ser Asp Ala Ala Val Asp Thr Ser Ser Glu Ile Thr Thr Lys Asp Leu
 1               5                  10                  15

Lys Glu Lys Lys Glu Val Val Glu Glu Ala Glu Asn Gly Arg Glu Ala
            20                  25                  30

Pro Ala Asn Gly Asn Ala Asn Glu Glu Asn Gly Glu Gln Glu Ala Asp
        35                  40                  45

Asn Glu Val Asp Glu Glu Glu Glu Glu Gly Gly Glu Glu Glu Glu Glu
    50                  55                  60

Glu Glu Glu Gly Asp Gly Glu Glu Glu Asp Gly Asp Glu Asp Glu Glu
65                  70                  75                  80

Ala Glu Ala Ala Thr Gly Lys Arg Ala Ala Glu Asp Asp Glu Asp Asp
                85                  90                  95

Asp Val Asp Thr Lys Lys Gln Lys Thr Asp Glu Asp Asp
            100                 105


<210> SEQ ID NO 10
<211> LENGTH: 105
<212> TYPE: PRT
<213> ORGANISM: Danio rerio

<400> SEQUENCE: 10

Met Ala Asp Thr Lys Val Asp Thr Ser Lys Glu Val Ser Ala Lys Asp
```

-continued

```
 1               5                  10                  15

Leu Lys Glu Lys Lys Gln Val Glu Glu Ala Glu Asn Gly Lys Asp Ala
            20                  25                  30

Pro Ala Asn Gly Asn Ala Glu Asn Glu Glu Asn Gly Asp Gln Glu Asn
        35                  40                  45

Glu Val Asp Glu Glu Asp Asp Asp Val Ala Glu Glu Asp Glu Glu Asp
    50                  55                  60

Asp Gly Glu Gly Asp Asp Asp Asp Glu Asp Glu Glu Ala Glu Gly Gly
65                  70                  75                  80

Thr Gly Lys Arg Ala Ala Glu Asp Asp Asp Asp Asp Glu Asp Asp Val
                85                  90                  95

Asp Pro Lys Lys Gln Lys Thr Asp Val
            100                 105


<210> SEQ ID NO 11
<211> LENGTH: 109
<212> TYPE: PRT
<213> ORGANISM: Rana esculenta

<400> SEQUENCE: 11

Met Ser Asp Thr Ser Val Asp Ala Ser Val Glu Lys Thr Thr Lys Asp
 1               5                  10                  15

Leu Lys Ser Lys Asp Lys Glu Leu Val Glu Glu Thr Glu Asn Gly Lys
            20                  25                  30

Asp Lys Pro Ala Asn Gly Asn Ala Glu Asn Glu Glu Asn Gly Glu Asp
        35                  40                  45

Gly Ala Asp Asn Glu Glu Glu Glu Glu Val Asp Glu Glu Asp Glu Glu
    50                  55                  60

Asp Glu Gly Glu Gly Asp Asp Asp Glu Gly Asp Glu Asp Asp Glu Ala
65                  70                  75                  80

Asp Gly Ala Thr Gly Lys Arg Ala Ala Glu Asp Asp Asp Glu Asp Asp
                85                  90                  95

Asp Val Asp Ala Lys Lys Gln Lys Thr Asp Asp Asp Asp
            100                 105


<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12

aacaccccaa catcttcgac                                                 20


<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13

cggtacttcg tccacaaaca                                                 20


<210> SEQ ID NO 14
<211> LENGTH: 20
<212> TYPE: DNA
<213> ORGANISM: Artificial Sequence
<220> FEATURE:
```

-continued

```
<223> OTHER INFORMATION: Synthetic Primer

<400> SEQUENCE: 14

gccagcgtct gacgttatga                                              20


<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15

gagggctgat cctaccacaa                                              20
```